(12) United States Patent
Ruf et al.

(10) Patent No.: US 9,150,526 B2
(45) Date of Patent: Oct. 6, 2015

(54) BIARYL-PROPIONIC ACID DERIVATIVES AND THEIR USE AS PHARMACEUTICALS

(71) Applicant: SANOFI, Paris (FR)

(72) Inventors: Sven Ruf, Frankfurt am Main (DE); Thorsten Sadowski, Frankfurt am Main (DE); Klaus Wirth, Frankfurt am Main (DE); Herman Schreuder, Frankfurt am Main (DE); Christian Buning, Frankfurt am Main (DE); Christopher Kallus, Frankfurt am Main (DE); Hartmut Strobel, Frankfurt am Main (DE); Hermut Wehlan, Frankfurt am Main (DE)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 14/227,679

(22) Filed: Mar. 27, 2014

(65) Prior Publication Data

US 2014/0296296 A1  Oct. 2, 2014

(30) Foreign Application Priority Data

Mar. 28, 2013  (EP) .................................... 13305401

(51) Int. Cl.
| C07D 271/10 | (2006.01) |
| C07D 413/06 | (2006.01) |
| C07D 413/04 | (2006.01) |
| C07D 413/10 | (2006.01) |
| C07D 263/32 | (2006.01) |
| C07D 277/30 | (2006.01) |
| C07D 413/14 | (2006.01) |

(52) U.S. Cl.
CPC ............ C07D 271/10 (2013.01); C07D 263/32 (2013.01); C07D 277/30 (2013.01); C07D 413/06 (2013.01); C07D 413/10 (2013.01); C07D 413/14 (2013.01)

(58) Field of Classification Search
CPC .. C07D 271/10; C07D 413/06; C07D 413/14; C07D 413/10; C07D 263/32; C07D 277/30
See application file for complete search history.

(56) References Cited

U.S. PATENT DOCUMENTS

| 5,051,518 A | * | 9/1991 | Murray et al. ............. 548/375.1 |
| 2004/0072802 A1 | | 4/2004 | Duan et al. |

FOREIGN PATENT DOCUMENTS

| JP | 2005145839 | 6/2005 |
| WO | 2004056815 | 7/2004 |
| WO | 2006076202 | 7/2006 |
| WO | 2009080226 | 7/2009 |
| WO | 2009080227 | 7/2009 |
| WO | 2011/092187 | 8/2011 |
| WO | 2012/101199 | 8/2012 |
| WO | 2012101197 | 8/2012 |
| WO | 2013014204 | 1/2013 |
| WO | 2013014205 | 1/2013 |
| WO | 2013072327 | 5/2013 |
| WO | 2013072328 | 5/2013 |

OTHER PUBLICATIONS

Chao, Julie, et al., "The Tissue kallikrein-kinin system protects against cardiovascular and renal disease and ischemic stroke independently of blood pressure reduction"; Bioi. Chern. vol. 387, pp. 665-675 (Jun. 2006).

d'Azzo, A. et al., The Metabolic and Molecular Bases of Inherited Disease, vol. 2 (1995), 2835-2837 (1995).

Galjart, Neils, J., et al., "Human Lysosomal Protective Protein Has Cathepsin A-like Activity Distinct from Its Protective Function", The Journal of Biological Chemistry, vol. 266, No. 22, pp. 14754-14762 (Aug. 5, 1991).

Hanna, William L., et al., "The Dominant Chymotrypsin-Like Esterase Activity in Human Lymphocyte Granules is Mediated by the Serine Carboxypeptidase Called Cathepsin A-Like Protective Protein", The Journal of Immunology, 1994,153: pp. 4663-4672 (Nov. 15, 1994).

(Continued)

Primary Examiner — Matthew Coughlin
(74) Attorney, Agent, or Firm — McDonnell Boehnen Hulbert & Berghoff

(57) ABSTRACT

The present invention relates to compounds of the formula I,

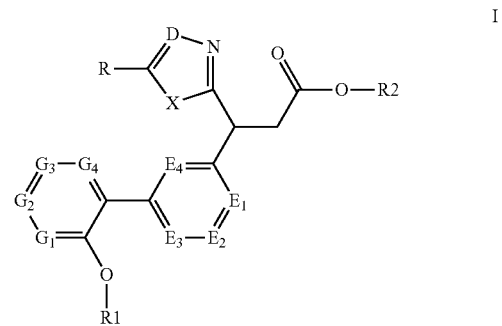

wherein X, R, R1, R2, D, E1, E2, E3, E4, G1, G2, G3 and G4 have the meanings indicated in the claims, which are valuable pharmaceutical active compounds. They are inhibitors of the protease cathepsin A, and are useful for the treatment of diseases such as atherosclerosis, heart failure, renal diseases, liver diseases or inflammatory diseases, for example. The invention furthermore relates to processes for the preparation of the compounds of the formula I, their use and pharmaceutical compositions comprising them.

17 Claims, No Drawings

(56) References Cited

OTHER PUBLICATIONS

Hayashi, I., et al., "In Vivo Transfer of Antisense Oligonucleotide Against Urinary Kininase Blunts Deoxycorticosterone Acetate-Salt Hypertension in Rats", British Journal of Pharmacology, vol. 131, No. 4, pp. 820-826 (Oct. 1, 2000).

Hinek, A.; "Biological roles of the non-integrin elastin/lam in in receptor"; Biol. Chem. 377 (1996), 471-480 (Jul.-Aug. 1996).

Hiraiwa M., "Cathepsin A/Protective Protein: an Unusual Lysosomal Multifunctional Protein", Cellular and Molecular Life Sciences, vol. 56, No. 11-12, pp. 894-907 (Dec. 31, 1999).

Ito H. et al., "Effect of Prolonged Administration of a Urinary Kininase Inhibitor, Ebelactone B on the Development of Deoxycorticosterone Acetate-Salt Hypertension in Rats", British Journal of Pharmaceology, vol. 126, No. 3, pp. 613-620 (Feb. 1, 1999).

Linz, Wolfgang, et al., "Vasopeplidase Inhibition Prevents Target Organ Damage and Improves Survival in Spontaneously Hypertensive Rats", Journal of the Renin-Angiotensin-Aldosterone System, vol. 7, No. 3 (Sep. 2006).

Madeddu, Paolo, et al., "Mechanisms of Disease: the tissue kallidrein-kinin system in hypertension and vascular remodeling", www.nature.com/clinicalpractice/neph (Oct. 25, 2006).

Marceau, Francois, et al., "Bradykinin Receptor Ligands: Therapeutic Perspectives", Nature Reviews, Drug Discovery, vol. 3, 845-851 (Oct. 2004).

M. Mora et. al, "Recent Advances in the Heterogeneous Palladium-Catalysed Suzuki Cross-Coupling Reaction"; Current Organic Chemistry 2012, 1128-1150 (May 1, 2012).

Ostrowska, Halina, Cathepsin A-Like Activity in Thrombin-Activated Human Platelets, Substrate Specificity, pH Dependence, and Inhibitory Profile, Thrombosis Research, vol. 86, No. 5, p. 393-404, 1997 (Jun. 1, 1997).

Ostrowska H. et al., "Ebelactone B, an Inhibitor of Extracellular Cathepsin A-Type Enzyme, Suppresses Platelet Aggregation Ex Vivo in Renovascular Hypertensive Rats", Journal of Cardiovascular Pharmacology, vol. 45, No. 4, pp. 348-353 (Jan. 1, 2005).

Planes, C., et al., "Regulation of the Epithelial Na+ Channel by Peptidases"; Curr. Top. Dev. Biol. 78 (2007), 23-46 (Mar. 3, 2007).

Reich, Michael, et al., "Specific cathepsin B inhibitor is cell-permeable and activates presentation of TTC in primary human dendritic cells", Immunology Letters 123 (2009) 155-159 (Mar. 24, 2009).

Rottier, Robbert J., et al., "Lack of PPCA expression only partially coincides with lysosomal storage in galactosialidosis mice: indirect evidence for spatial requirement of the catalytic rather than the protective function of PPCA", Human Molecular Genetics, 1998, vol. 7, No. 11, pp. 1787-1794 (Oct. 1998).

Rudenko, Gabby, et al., "The atomic model of the human protective protein/cathepsin A suggests a structural basis for balactosialidosis", Proc. Nail. Acad. Sci. USA, vol. 95, pp. 621-625 (Jan. 1998).

Ruf, S., et al., "Novel β-Amino Acid Derivatives as Inhibitors of Cathepsin A"; J. Med. Chem. 2012, 55, No. 17, 7636-7649 (Aug. 3, 2012).

Saito, M., et al., "Degradation of Bradykinin in Human Urine by Carboxypeptidase Y-Like Exopeptidase and Neutral.Endopeptidase and Their Inhibition by Ebelactone Band Phosphoramidon", International Journal of Tissue Reactions, vol. 17, No. 5-6, pp. 181-190 (1995).

Seyrantepe, Volkan, et al., "Enzymatic Activity of Lysosomal Carbosypeptidase (Cathepsin) A is Required for Proper.Elastic Fiber Formation and Inactivation of Endothelin-1 ", Circulation American Heart Association, Circulation 2008, 117; 1973-1981 (Apr. 2008).

Sohma, Osamu, et al., "Expression of Protective Protein in Human Tissue", Pediatric Neurology, vol. 20, No. 5, 1999, pp. 210-214 (May 1999).

Stamatos, Nicholas M., et al., "Differential expression of endogenous sialidases of human monocytes during cellular differentiation into macrophages", FEBS Journal 272 (2005) 2545-2556 (Apr. 22, 2005).

European Search Report for European Patent Application No. EP 13 30 5401 dated Oct. 21, 2013 (mailed Oct. 25, 2013).

\* cited by examiner

BIARYL-PROPIONIC ACID DERIVATIVES AND THEIR USE AS PHARMACEUTICALS

This application claims the benefit of European Application No. EP13305401.5, filed Mar. 28, 2013, the disclosure of which is herein incorporated by reference in its entirety.

The present invention relates to compounds of the formula I,

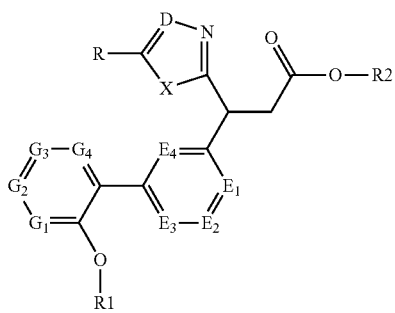

wherein X, R, R1, R2, D, $E_1$, $E_2$, $E_3$, $E_4$, $G_1$, $G_2$, $G_3$ and $G_4$ have the meanings indicated below, which are valuable pharmaceutical active compounds. They are inhibitors of the protease cathepsin A, and are useful for the treatment of diseases such as atherosclerosis, heart failure, renal diseases, liver diseases or inflammatory diseases, for example. The invention furthermore relates to processes for the preparation of the compounds of the formula I, their use and pharmaceutical compositions comprising them.

Cathepsin A (EC=3.4.16.5; gene symbol CTSA) is a protease also known as lysosomal carboxypeptidase A or protective protein. It belongs to a family of serine carboxypeptidases which contains only two other mammalian representatives, retinoid-inducible serine carboxypeptidase and vitellogenic carboxypeptidase-like protein. Within the cell cathepsin A resides in lysosomes where it forms a high molecular weight complex with beta-galactosidase and neuraminidase. The interaction of cathepsin A with these glycosidases is essential for their correct routing to the lysosome and protects them from intralysosomal proteolysis. A deficiency of cathepsin A resulting from various mutations in the ctsa gene leads to a secondary deficiency of beta-galactosidase and neuraminidase that is manifest as the autosomal recessive lysosomal storage disorder galactosialidosis (cf. A. d'Azzo et al., in "The Metabolic and Molecular Bases of Inherited Disease", vol. 2 (1995), 2835-2837). The majority of identified mutations in ctsa are missense mutations affecting the folding or the stability of the protein. None of them was shown to occur in the active site of the enzyme (G. Rudenko et al., Proc. Natl. Acad. Sci. USA 95 (1998), 621-625). Accordingly, the lysosomal storage disorder can be corrected with catalytically inactive cathepsin A mutants (N. J. Galjart et al., J. Biol. Chem. 266 (1991), 14754-14762). The structural function of cathepsin A is therefore separable from its catalytic activity. This is also underscored by the observation that in contrast to mice deficient in the ctsa gene, mice carrying a catalytically inactivating mutation in the ctsa gene do not develop signs of the human disease galactosialidosis (R. J. Rottier et al., Hum. Mol. Genet. 7 (1998), 1787-1794; V. Seyrantepe et al., Circulation 117 (2008), 1973-1981).

Cathepsin A displays carboxypeptidase activity at acidic pH and deamidase and esterase activities at neutral pH against various naturally occurring bioactive peptides. In vitro studies have indicated that cathepsin A converts angiotensin I to angiotensin 1-9 and bradykinin to bradykinin 1-8, which is the ligand for the bradykinin B1 receptor. It hydrolyzes endothelin-1, neurokinin and oxytocin, and deamidates substance P (cf. M. Hiraiwa, Cell. Mol. Life Sci. 56 (1999), 894-907). High cathepsin A activity has been detected in urine, suggesting that it is responsible for tubular bradykinin degradation (M. Saito et al., Int. J. Tiss. Reac. 17 (1995), 181-190). However, the enzyme can also be released from platelets and lymphocytes and is expressed in antigen-presenting cells where it might be involved in antigen processing (W. L. Hanna et al., J. Immunol. 153 (1994), 4663-4672; H. Ostrowska, Thromb. Res. 86 (1997), 393-404; M. Reich et al., Immunol. Lett. (online Nov. 30, 2009)). Immunohistochemistry of human organs revealed prominent expression in renal tubular cells, bronchial epithelial cells, Leydig's cells of the testis and large neurons of the brain (O. Sohma et al., Pediatr. Neurol. 20 (1999), 210-214). It is upregulated during differentiation of monocytes to macrophages (N. M. Stamatos et al., FEBS J. 272 (2005), 2545-2556). Apart from structural and enzymatic functions, cathepsin A has been shown to associate with neuraminidase and an alternatively spliced beta-galactosidase to form the cell-surface laminin and elastin receptor complex expressed on fibroblasts, smooth muscle cells, chondroblasts, leukocytes and certain cancer cell types (A. Hinek, Biol. Chem. 377 (1996), 471-480).

The importance of cathepsin A for the regulation of local bradykinin levels has been demonstrated in animal models of hypertension. Pharmacological inhibition of cathepsin A activity increased renal bradykinin levels and prevented the development of salt-induced hypertension (H. Ito et al., Br. J. Pharmacol. 126 (1999), 613-620). This could also be achieved by antisense oligonucleotides suppressing the expression of cathepsin A (I. Hajashi et al., Br. J. Pharmacol. 131 (2000), 820-826). Besides in hypertension, beneficial effects of bradykinin have been demonstrated in various further cardiovascular diseases and other diseases (cf. J. Chao et al., Biol. Chem. 387 (2006), 665-75; P. Madeddu et al., Nat. Clin. Pract. Nephrol. 3 (2007), 208-221). Key indications of cathepsin A inhibitors therefore include atherosclerosis, heart failure, cardiac infarction, cardiac hypertrophy, vascular hypertrophy, left ventricular dysfunction, in particular left ventricular dysfunction after myocardial infarction, renal diseases such as renal fibrosis, renal failure and kidney insufficiency; liver diseases such as liver fibrosis and liver cirrhosis, diabetes complications such as nephropathy, as well as organ protection of organs such as the heart and the kidney.

As indicated above, cathepsin A inhibitors can prevent the generation of the bradykinin B1 receptor ligand bradykinin 1-8 (M. Saito et al., Int. J. Tiss. Reac. 17 (1995), 181-190). This offers the opportunity to use cathepsin A inhibitors for the treatment of pain, in particular neuropathic pain, and inflammation, as has been shown for bradykinin B1 receptor antagonists (cf. F. Marceau et al., Nat. Rev. Drug Discov. 3 (2004), 845-852). Cathepsin A inhibitors can further be used as anti-platelet agents as has been demonstrated for the cathepsin A inhibitor ebelactone B, a propiolactone derivative, which suppresses platelet aggregation in hypertensive animals (H. Ostrowska et al., J. Cardiovasc. Pharmacol. 45 (2005), 348-353).

Further, like other serine proteases such as prostasin, elastase or matriptase, cathepsin A can stimulate the amiloride-sensitive epithelial sodium channel (ENaC) and is thereby involved in the regulation of fluid volumes across epithelial membranes (cf. C. Planes et al., Curr. Top. Dev. Biol. 78 (2007), 23-46). Thus, respiratory diseases can be ameliorated by the use of cathepsin A inhibitors, such as cystic fibrosis, chronic bronchitis, chronic obstructive pulmonary disease, asthma, respiratory tract infections and lung carcinoma. Cathepsin A modulation in the kidney could be used to promote diuresis and thereby induce a hypotensive effect. Also beneficial effects of Cathepsin A inhibitors on atrial fibrillation are reported in J. Med. Chem. 2012, 55, no. 17, 7636-7649.

Besides for the above-mentioned compound ebelactone B, an inhibitory effect on cathepsin A has been found for certain dipeptidic phenylalanine derivatives which are described in JP 2005/145839. Also in WO2011/092187, WO2012/101197, WO2012/101199, PCT/EP2012/064628, PCT/EP2012/064629, PCT/EP2012/072538, PCT/EP2012/072539 compounds with inhibitory activity on Cathepsin A are disclosed. There is a need for further compounds which inhibit cathepsin A and offer an opportunity for the treatment of the mentioned diseases and further diseases in which cathepsin A plays a role. The present invention satisfies this need by providing the oxygen-substituted 3-heteroaroylamino-propionic acid derivatives of the formula I defined below.

Certain compounds in which a 3-heteroaroylamino-propionic acid moiety can be present, have already been described. For example, in WO 2006/076202 amine derivatives, which modulate the activity of steroid nuclear receptors, are described which carry on the nitrogen atom of the amine function a heteroaroyl group and a further group which is defined very broadly. In US 2004/0072802 broadly-defined beta-amino acid derivatives are described which carry an acyl group on the beta-amino group and are inhibitors of matrix metalloproteases and/or tumor necrosis factor. In WO 2009/080226 and WO 2009/080227, which relate to antagonists of the platelet ADP receptor P2Y12 and inhibit platelet aggregation, pyrazoloylamino-substituted carboxylic acid derivatives are described which, however, additionally carry a carboxylic acid derivative group on the carbon atom carrying the pyrazoloylamino group. Other pyrazoloylamino-substituted compounds, in which the nitrogen atom of the amino group is connected to a ring system and which are inhibitors of the blood clotting enzymes factor Xa and/or factor VIIa, are described in WO 2004/056815.

A subject of the present invention is a compound of the formula I, in any of its stereoisomeric forms or a mixture of stereoisomeric forms in any ratio, or a physiologically acceptable salt thereof, or a physiologically acceptable solvate of any of them,

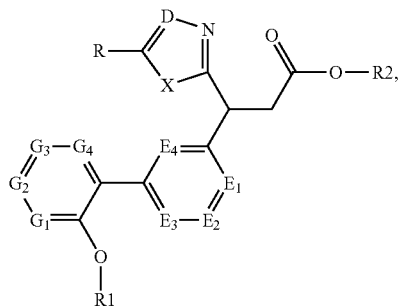

I wherein the meanings are:
X is S or O;
D is N or —C(R3)=;

R is H, $(C_1-C_6)$-alkyl, $(C_3-C_8)$-cycloalkyl;

R1 is H, $(C_1-C_6)$-alkyl, $(C_3-C_8)$-cycloalkyl, $(C_1-C_6)$-alkylen-$(C_3-C_8)$-cycloalkyl; wherein alkyl is optionally substituted by one ore more F-atoms;

R3 is H, methyl or ethyl;

R2 is Hydrogen or $(C_1-C_6-)$-alkyl;

$E_1$ is N or —C(R4)=;

$E_2$ is N or —C(R5)=;

$E_3$ is N or —C(R6)=;

$E_4$ is N or —C(R7)=; wherein none or one of $E_1$, $E_2$, $E_3$ or $E_4$ is N;

R4 is H or O—$(C_1-C_6)$-alkyl;

R5 is H F, Cl, $CF_3$, $(C_1-C_6)$-alkyl, $(C_1-C_6)$-cycloalkyl;

R6 is H;

R7 is H;

$G_1$ is N or —C(R8)=;

$G_2$ is N or —C(R9)=;

$G_3$ is N or —C(R10)=;

$G_4$ is N or —C(R11)=; wherein none or one of $G_1$, $G_2$, $G_3$ or $G_4$ is N;

or $G_3$ and $G_4$ are —C(R10)= and —C(R11)=, wherein R10 and R11 form a 4 to 7 membered saturated carbocycle- or heterocycle with one or two oxygen atoms; which is optionally mono- or disubstituted by $(C_1-C_3)$-alkyl;

R8 is H, F, Cl, $(C_1-C_6)$-alkyl, O—$(C_1-C_6)$-alkyl, $CF_3$ or $OCF_3$;

R9 is H, F, Cl, OH, O—$(C_1-C_6)$-alkyl, $CH_2OH$, CO—$NH_2$, $(C_1-C_6)$-alkyl, O—$(C_1-C_6)$-alkyl, $CF_3$ or $OCF_3$;

R10 is H, F, Cl, OH, $(C_1-C_6)$-alkyl, $CH_2OH$, CO—O—$(C_1-C_6)$-alkyl, $SO_2$—$(C_1-C_6)$-alkyl, CN, O—$(C_1-C_6)$-alkyl, $CF_3$ or $OCF_3$;

R11 is H, F, Cl, OH, O—$(C_1-C_6)$-alkyl, $CH_2OH$, CO—$(C_1-C_6)$-methyl, CO—N(R20R21), CO—O—$(C_1-C_6)$-alkyl, CN, $(C_1-C_6)$-alkyl, O—$(C_1-C_6)$-alkyl or $OCF_3$; wherein R20 and R21 are independently from each other H or $(C_1-C_3)$-alkyl or form together with the nitrogen to which they are attached a 5 or 6 membered saturated ring.

In terms of formulae resulting from formula I by incorporation of meanings of D, X, $E_1$, $E_2$, $E_3$, and $E_4$, or $G_1$, $G_2$, $G_3$ and G, in one embodiment of the invention a compound of the formula I is a compound of any one or more of formulae I-1 to I-20, for example a compound of formula I-1, or a compound of formula I-2, or a compound of formula I-3, or a compound of formula I-4, or a compound of formula I-5, or a compound of formula I-6, or a compound of formula I-7, or a compound of formula I-8, or a compound of formula I-9 or formula I-10, or a compound of formula I-11 or formula I-12, or a compound of formula I-13 or formula I-14 or formula I-15, or formula I-16, or formula I-17, or formula I-18, or formula I-19, or formula I-20, in any of its stereoisomeric forms or a mixture of stereoisomeric forms in any ratio, or a physiologically acceptable salt thereof, or a physiologically acceptable solvate of any of them, wherein in the compounds of formulae I-1 to I-20 the groups D, R, R1, R2, R4, R5, R6, R7, R8, R9, R10, R11, $E_1$, $E_2$, $E_3$, $E_4$, $G_1$, $G_2$, $G_3$ and $G_4$, are defined as in the compounds of formula I in general or in any embodiment specified above or below.

I-1 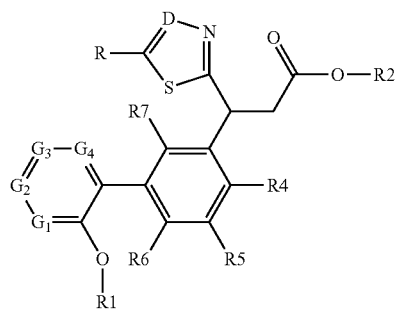
I-6 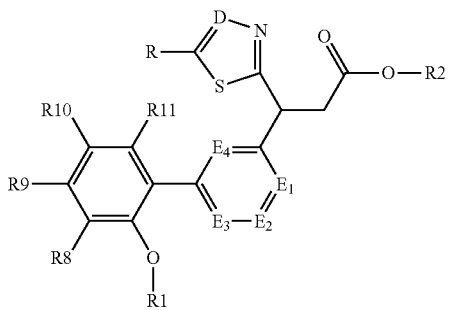
I-2 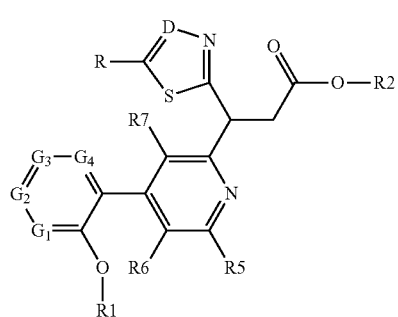
I-7 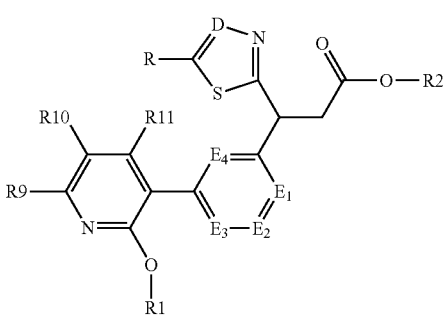
I-3 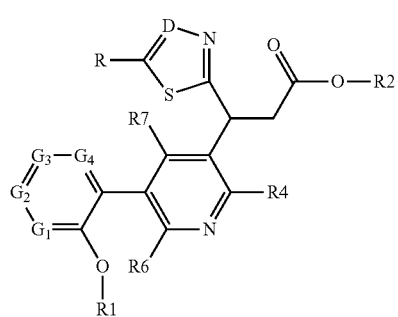
I-8 
I-4 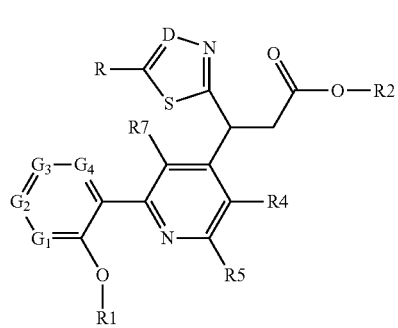
I-9 
I-5 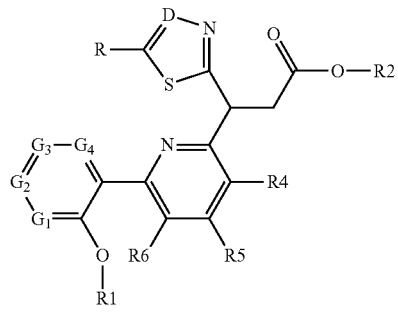
I-10 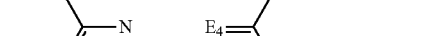

I-11
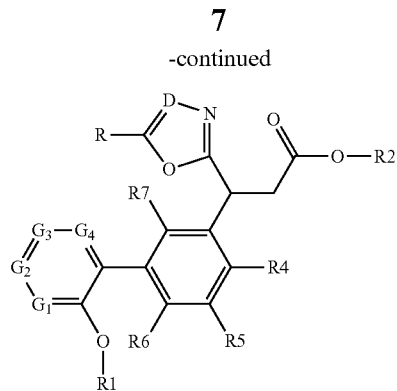
I-12
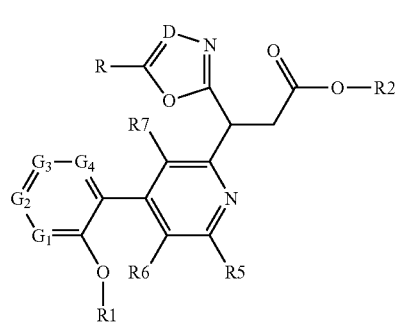
I-13
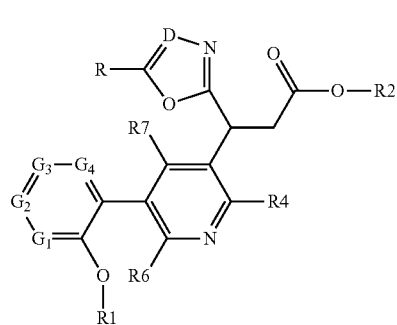
I-14
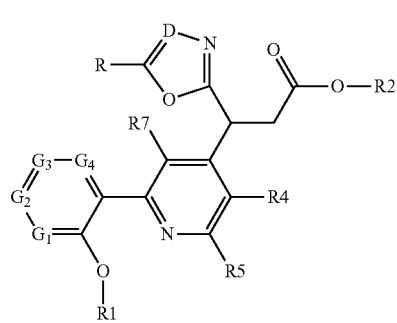
I-15
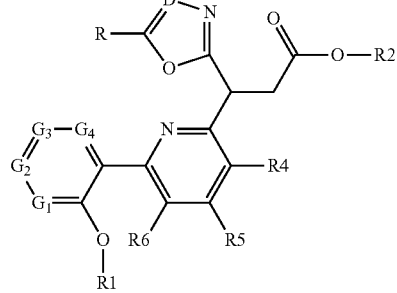
I-16
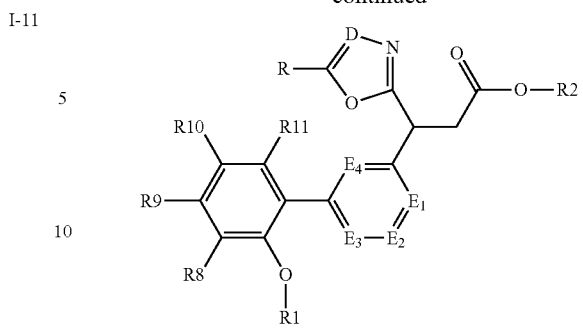
I-17
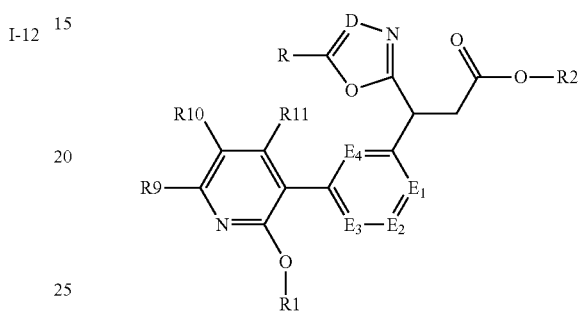
I-18
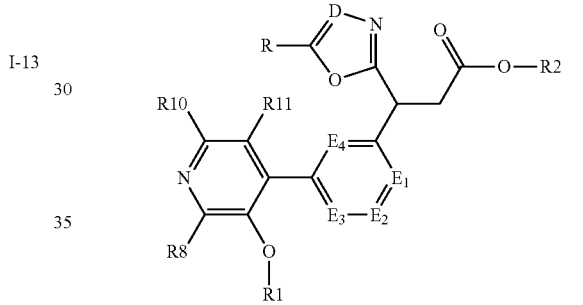
I-19
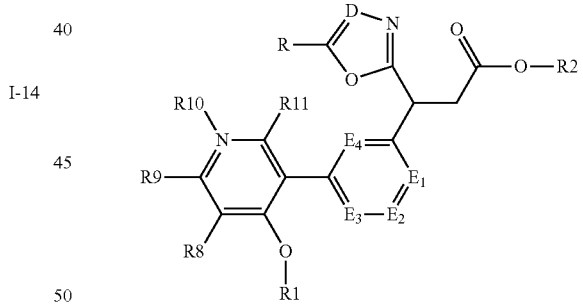
I-20
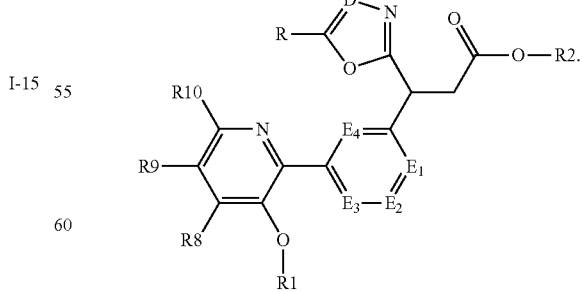
Another embodiment of the invention are compounds of formula I-1, I-2, I-3, I-4, I-5, I-11, I-12, I-13, I-14 or I-15, the groups D, R, R1, R2, R4, R5, R6, R7, R8, R9, R10, R11, $E_1$, $E_2$, $E_3$, $E_4$, defined as in the compounds of formula I in general or in any embodiment specified above or below,
wherein
$G_1$ is —C(R8)=;
$G_2$ is —C(R9)=;
$G_3$ is —C(R10)=;
$G_4$ is —C(R11)=.

Another embodiment of the invention are compounds of formula I-1, I-2, I-3, I-4, I-5, I-11, I-12, I-13, I-14 or I-15, the groups D, R, R1, R2, R4, R5, R6, R7, R8, R9, R10, R11, $E_1$, $E_2$, $E_3$, $E_4$, defined as in the compounds of formula I in general or in any embodiment specified above or below, wherein
$G_1$ is N;
$G_2$ is —C(R9)=;
$G_3$ is —C(R10)=;
$G_4$ is —C(R11)=.

Another embodiment of the invention are compounds of formula I-1, I-2, I-3, I-4, I-5, I-11, I-12, I-13, I-14 or I-15, the groups D, R, R1, R2, R4, R5, R6, R7, R8, R9, R10, R11, $E_1$, $E_2$, $E_3$, $E_4$, defined as in the compounds of formula I in general or in any embodiment specified above or below, wherein
$G_1$ is —C(R8)=;
$G_2$ is N;
$G_3$ is —C(R10)=;
$G_4$ is —C(R11)=.

Another embodiment of the invention are compounds of formula I-1, I-2, I-3, I-4, I-5, I-11, I-12, I-13, I-14 or I-15, the groups D, R, R1, R2, R4, R5, R6, R7, R8, R9, R10, R11, $E_1$, $E_2$, $E_3$, $E_4$, defined as in the compounds of formula I in general or in any embodiment specified above or below, wherein
$G_1$ is —C(R8)=;
$G_2$ is —C(R9)=;
$G_3$ is N;
$G_4$ is —C(R11)=.

Another embodiment of the invention are compounds of formula I-1, I-2, I-3, I-4, I-5, I-11, I-12, I-13, I-14 or I-15, the groups D, R, R1, R2, R4, R5, R6, R7, R8, R9, R10, R11, $E_1$, $E_2$, $E_3$, $E_4$, defined as in the compounds of formula I in general or in any embodiment specified above or below, wherein
$G_1$ is —C(R8)=;
$G_2$ is —C(R9)=;
$G_3$ is —C(R10)=;
$G_4$ is N.

Another embodiment of the invention are compounds of formula I-6, I-7, I-8, I-9, I-10, I-16, I-17, I-18, I-19 or I-20, the groups D, R, R1, R2, R4, R5, R6, R7, R8, R9, R10, R11, $G_1$, $G_2$, $G_3$ and $G_4$, defined as in the compounds of formula I in general or in any embodiment specified above or below, wherein
$E_1$ is —C(R4)=;
$E_2$ is —C(R5)=;
$E_3$ is —C(R6)=;
$E_4$ is —C(R7)=.

Another embodiment of the invention are compounds of formula I-6, I-7, I-8, I-9, I-10, I-16, I-17, I-18, I-19 or I-20, the groups D, R, R1, R2, R4, R5, R6, R7, R8, R9, R10, R11, $G_1$, $G_2$, $G_3$ and $G_4$, defined as in the compounds of formula I in general or in any embodiment specified above or below, wherein
$E_1$ is N;
$E_2$ is —C(R5)=;
$E_3$ is —C(R6)=;
$E_4$ is —C(R7)=.

Another embodiment of the invention are compounds of formula I-6, I-7, I-8, I-9, I-10, I-16, I-17, I-18, I-19 or I-20, the groups D, R, R1, R2, R4, R5, R6, R7, R8, R9, R10, R11, $G_1$, $G_2$, $G_3$ and $G_4$, defined as in the compounds of formula I in general or in any embodiment specified above or below, wherein
$E_1$ is —C(R4)=;
$E_2$ is N;
$E_3$ is —C(R6)=;
$E_4$ is —C(R7)=.

Another embodiment of the invention are compounds of formula I-6, I-7, I-8, I-9, I-10, I-16, I-17, I-18, I-19 or I-20, the groups D, R, R1, R2, R4, R5, R6, R7, R8, R9, R10, R11, $G_1$, $G_2$, $G_3$ and $G_4$, defined as in the compounds of formula I in general or in any embodiment specified above or below, wherein
$E_1$ or —C(R4)=;
$E_2$ is —C(R5)=;
$E_3$ is N;
$E_4$ is —C(R7)=.

Another embodiment of the invention are compounds of formula I-6, I-7, I-8, I-9, I-10, I-16, I-17, I-18, I-19 or I-20, the groups D, R, R1, R2, R4, R5, R6, R7, R8, R9, R10, R11, $G_1$, $G_2$, $G_3$ and $G_4$, defined as in the compounds of formula I in general or in any embodiment specified above or below, wherein
$E_1$ is —C(R4)=;
$E_2$ is —C(R5)=;
$E_3$ is —C(R6)=;
$E_4$ is N.

Another embodiment of the invention are compounds of formula I-1 or I-11

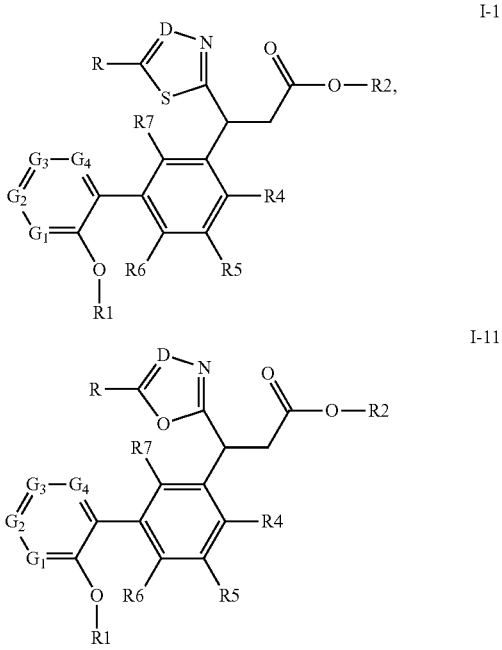

wherein the groups D, R, R1, R2, R4, R5, R6, R7, R8, R9, R10, R11 are defined as in the compounds of formula I in general or in any embodiment specified above or below, wherein
$G_1$ is —C(R8)=;
$G_2$ is —C(R9)=;
$G_3$ is —C(R10)=;
$G_4$ is —C(R11)=.

One embodiment of the invention are compounds of formula I wherein
R is Hydrogen, methyl or ethyl.

One embodiment of the invention are compounds of formula I wherein
R1 is H, methyl, ethyl, CF$_3$, —CH$_2$-cyclopropyl or —CH$_2$—C(CH$_3$)$_3$.

One embodiment of the invention are compounds of formula I wherein
R1 is H, methyl, ethyl, —CH$_2$-cyclopropyl or —CH$_2$—C(CH$_3$)$_3$.

One embodiment of the invention are compounds of formula I wherein
R1 is methyl or ethyl.

One embodiment of the invention are compounds of formula I wherein
R2 is Hydrogen or (C$_1$-C$_6$-)-alkyl.

One embodiment of the invention are compounds of formula I wherein
R2 is Hydrogen.

One embodiment of the invention are compounds of formula I wherein
R4 is H or O-methyl.

One embodiment of the invention are compounds of formula I wherein
R5 is H F, Cl, CF$_3$, (C$_1$-C$_6$)-alkyl, cyclopropyl.

One embodiment of the invention are compounds of formula I wherein
R8 is H, F, Cl, methyl, O-methyl, CF$_3$ or OCF$_3$.

One embodiment of the invention are compounds of formula I wherein
R8 is H, F, Cl, methyl or O-methyl.

One embodiment of the invention are compounds of formula I wherein
R9 is H, F, Cl, OH, O-propyl, CH$_2$OH, CO—NH$_2$, methyl, O-methyl, CF$_3$ or OCF$_3$;

One embodiment of the invention are compounds of formula I wherein
R9 is H, F, Cl, OH, O-propyl, CH$_2$OH, CO—NH$_2$, methyl, O-methyl.

One embodiment of the invention are compounds of formula I wherein
R10 is H, F, Cl, OH, i-propyl, t-butyl, CH$_2$OH, CO—O-methyl, SO$_2$-methyl, CN, methyl, O-methyl, CF$_3$ or OCF$_3$.

One embodiment of the invention are compounds of formula I wherein
R10 is H, F, Cl, OH, methyl, i-propyl, t-butyl, CH$_2$OH, CO—O-methyl, O-methyl.

One embodiment of the invention are compounds of formula I wherein
R11 is H, F, Cl, OH, O-methyl, O-i-propyl, CH$_2$OH, CO-methyl, CO—N(methyl)$_2$, CO-pyrrolidin, CO—O-methyl, CN, methyl or OCF$_3$;

One embodiment of the invention are compounds of formula I wherein
R11 is H, F, Cl, OH, methyl, O-i-propyl, CH$_2$OH, CO-methyl, CO—N(methyl)$_2$, CO—O-methyl, O-methyl.

One embodiment of the invention are compounds of formula I wherein
G$_3$ and G$_4$ are —C(R10)= and —C(R11)=, wherein R10 and R11 form a 5 or 6 membered saturated carbocycle or heterocycle with one or two oxygen atoms; which is optionally mono- or disubstituted by halogen and or (C$_1$-C$_3$)-alkyl.

One embodiment of the invention are compounds of formula I wherein
G$_1$ is —C(R8)=;
G$_2$ is —C(R9)=;
G$_3$ is —C(R10)=;
G$_4$ is —C(R11)=;
wherein R10 and R11 form a 5 or 6 membered saturated carbocycle or heterocycle with one or two oxygen atoms; which is optionally mono- or disubstituted by (C$_1$-C$_3$)-alkyl forming a bycyclic ringstructure selected from

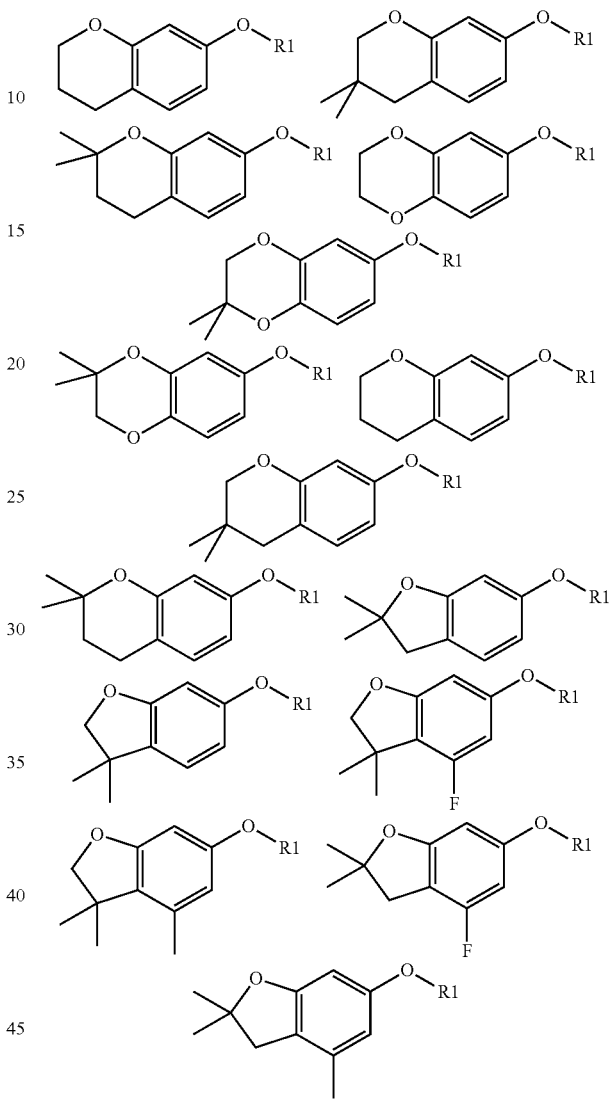

One embodiment of the invention are compounds of formula I wherein
G$_1$ is —C(R8)=;
G$_2$ is —C(R9)=;
G$_3$ is —C(R10)=;
G$_4$ is —C(R11)=;
wherein R10 and R11 form a 5 membered saturated carbo- or heterocycle with one or two oxygen atoms which is optionally mono- or disubstituted by (C$_1$-C$_3$)-alkyl forming a bycyclic ringstructure selected from

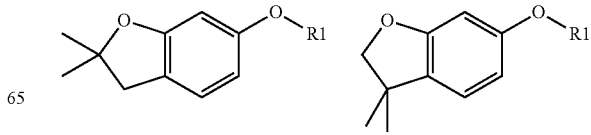

-continued

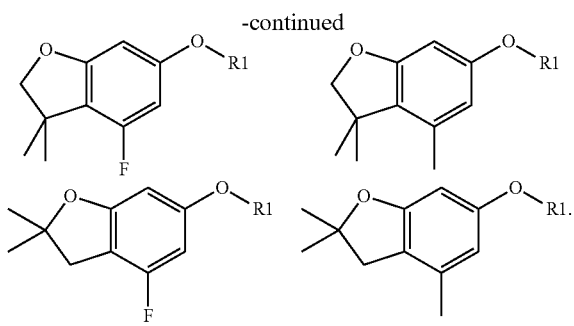

One embodiment of the invention are compounds of formula I wherein
$G_1$ is —C(R8)=;
$G_2$ is —C(R9)=;
$G_3$ is —C(R10)=;
$G_4$ is —C(R11)=;
wherein R10 and R11 form a 6 membered saturated carbo- or heterocycle with one or two oxygen atoms which is optionally mono- or disubstituted by $(C_1-C_3)$-alkyl forming a bycyclic ringstructure selected from

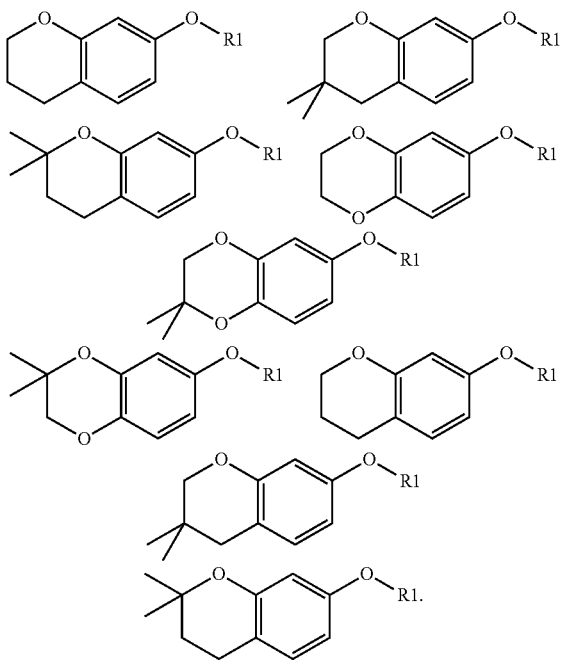

Another embodiment of the invention are compounds of formula I wherein
$G_1$ is —C(R8)=;
$G_2$ is —C(R9)=;
$G_3$ and $G_4$ are —C((methyl)$_2$)—CH$_2$—O—;
R8 is H;
R9 is H.

Another embodiment of the invention are compounds of formula I wherein
X is S;
D is —C(R3)=;
R is Hydrogen or methyl or ethyl;
R3 is H, methyl or ethyl.

Another embodiment of the invention are compounds of formula I wherein

X is O;
D is —C(R3)=;
R is Hydrogen or methyl or ethyl;
R3 is H, methyl or ethyl.

Another embodiment of the invention are compounds of formula I wherein
X is O;
D is N;
R is Hydrogen or methyl or ethyl;
R3 is H, methyl or ethyl.

Alkyl groups, i.e. saturated hydrocarbon residues, can be linear (straight-chain) or branched. This also applies if these groups are substituted or are part of another group, for example an alkyl-O— group (alkyloxy group, alkoxy group) or an HO-substituted alkyl group (hydroxyalkyl group). Depending on the respective definition, the number of carbon atoms in an alkyl group can be 1, 2, 3, 4, 5, 6, 7, 8, 9 or 10, or 1, 2, 3, 4, 5, 6, 7 or 8, or 1, 2, 3, 4, 5 or 6, or 1, 2, 3 or 4, or 1, 2 or 3, or 1 or 2, or 1, for example. In one embodiment of the invention, a $(C_1-C_{10})$-alkyl group present in the compounds of the formula I is a $(C_1-C_8)$-alkyl group, in another embodiment a $(C_1-C_6)$-alkyl group, in another embodiment a $(C_1-C_4)$-alkyl group, in another embodiment a $(C_1-C_3)$-alkyl group, in another embodiment a $(C_1-C_2)$-alkyl group, in another embodiment a $(C_2-C_3)$-alkyl group, in another embodiment a methyl group. In one embodiment of the invention, a $(C_1-C_8)$-alkyl group present in any position of the compounds of the formula I is a $(C_1-C_6)$-alkyl group, in another embodiment a $(C_1-C_4)$-alkyl group, in another embodiment a $(C_1-C_3)$-alkyl group, in another embodiment a $(C_1-C_2)$-alkyl group, in another embodiment a $(C_2-C_3)$-alkyl group, in another embodiment a methyl group, where any $(C_1-C_8)$-alkyl group present in the compounds of the formula I can independently of each other $(C_1-C_8)$-alkyl group be a group of any of these embodiments. In one embodiment of the invention, a $(C_1-C_6)$-alkyl group present in any position of the compounds of the formula I is a $(C_1-C_4)$-alkyl group, in another embodiment a $(C_1-C_3)$-alkyl group, in another embodiment a $(C_1-C_2)$-alkyl group, in another embodiment a $(C_2-C_3)$-alkyl group, in another embodiment a methyl group, where any $(C_1-C_6)$-alkyl group present in the compounds of the formula I can independently of each other $(C_1-C_6)$-alkyl group be a group of any of these embodiments. In one embodiment of the invention, a $(C_1-C_4)$-alkyl group present in any position of the compounds of the formula I is a $(C_1-C_3)$-alkyl group, in another embodiment a $(C_1-C_2)$-alkyl group, in another embodiment a $(C_2-C_3)$-alkyl group, in another embodiment a methyl group, where any $(C_1-C_4)$-alkyl group present in the compounds of the formula I can independently of each other $(C_1-C_4)$-alkyl group be a group of any of these embodiments. Examples of alkyl groups are methyl, ethyl, propyl groups including propyl (i.e. n-propyl) and isopropyl, butyl groups including butyl (i.e. n-butyl), sec-butyl, isobutyl and tert-butyl, pentyl groups including pentyl (i.e. n-pentyl), 1-methylbutyl, isopentyl, neopentyl and tert-pentyl, hexyl groups including hexyl (i.e. n-hexyl), 3,3-dimethylbutyl and isohexyl, heptyl groups including heptyl (i.e. n-heptyl), octyl groups including octyl (i.e. n-octyl), nonyl groups including nonyl (i.e. n-nonyl), and decyl groups including decyl (i.e. n-decyl). Examples of alkyl-O— groups are methoxy, ethoxy, propoxy (i.e. n-propoxy), isopropoxy, butoxy (i.e. n-butoxy), isobutoxy, tert-butoxy, pentoxy (i.e. n-pentoxy). Examples of alkyl-S(O)$_m$— are methylsulfanyl-(CH$_3$—S—), methanesulfinyl-(CH$_3$—S(O)—), methanesulfonyl (CH$_3$—S(O)$_2$—), ethylsulfanyl-(CH$_3$—CH$_2$—S—), ethanesulfinyl-(CH$_3$—CH$_2$—S(O)—), ethanesulfonyl (CH$_3$—CH$_2$—S(O)$_2$—), 1-methylethylsulfanyl-((CH$_3$)$_2$ CH—S—), 1-methylethanesulfinyl-((CH$_3$)$_2$CH—S(O)—), 1-methylethanesulfonyl ((CH$_3$)$_2$CH—S(O)$_2$—). In one embodiment of the invention the number m is chosen from 0 and 2, wherein all numbers m are independent of each other and can be identical or different. In another embodiment the number m in any of its occurrences is, independently of its meaning in other occurrences, 0. In another embodiment the number m in any of its occurrences is, independently of its meaning in other occurrences, 2.

A substituted alkyl group can be substituted in any positions, provided that the respective compound is sufficiently stable and is suitable as a pharmaceutical active compound. The prerequisite that a specific group and a compound of the formula I are sufficiently stable and suitable as a pharmaceutical active compound, applies in general with respect to the definitions of all groups in the compounds of the formula I. In one embodiment of the invention, an individual carbon atom in any alkyl group in the compounds of the formula I, as well as in other groups such as cycloalkyl groups and heterocyclic groups, for example, independently of any other carbon atom does not carry more than one substituent which is bonded via an oxygen atom, nitrogen atom or sulfur atom, such as HO—, (C$_1$-C$_4$)-alkyl-O— or (C$_1$-C$_4$)-alkyl-S(O)$_m$— substituents, for example. An alkyl group which is optionally substituted by one or more fluorine substituents can be unsubstituted, i.e. not carry fluorine substituents, or substituted, for example by one, two, three, four, five, six, seven, eight, nine, ten or eleven fluorine substituents, or by one, two, three, four, five, six or seven fluorine substituents, or by one, two, three, four or five fluorine substituents, or by one, two or three fluorine substituents, which can be located in any positions. For example, in a fluoro-substituted alkyl group one or more methyl groups can carry three fluorine substituents each and be present as trifluoromethyl groups, and/or one or more methylene groups (CH$_2$) can carry two fluorine substituents each and be present as difluoromethylene groups. The explanations with respect to the substitution of a group by fluorine also apply if the group additionally carries other substituents and/or is part of another group, for example of an alkyl-O— group. Examples of fluoro-substituted alkyl groups are trifluoromethyl, 2-fluoroethyl, 1-fluoroethyl, 1,1-difluoroethyl, 2,2,2-trifluoroethyl, pentafluoroethyl, 3,3,3-trifluoropropyl, 2,2,3,3,3-pentafluoropropyl, 4,4,4-trifluorobutyl and heptafluoroisopropyl. Examples of fluoro-substituted alkyl-O— groups are trifluoromethoxy, 2,2,2-trifluoroethoxy, pentafluoroethoxy and 3,3,3-trifluoropropoxy. Examples of fluoro-substituted alkyl-S(O)$_m$— groups are trifluoromethylsulfanyl-(CF$_3$—S—), trifluoromethanesulfinyl-(CF$_3$—S(O)—) and trifluoromethanesulfonyl (CF$_3$—S(O)$_2$—).

The number of ring carbon atoms in a (C$_3$-C$_7$)-cycloalkyl group can be 3, 4, 5, 6 or 7. Examples of cycloalkyl are cyclopropyl, cyclobutyl, cyclopentyl, cyclohexyl and cycloheptyl. As regards the optional substitution of cycloalkyl groups by one or more (C$_1$-C$_4$)-alkyl substituents, they be unsubstituted, i.e. not carry alkyl substituents, or substituted, for example by one, two, three or four, or by one or two, identical or different (C$_1$-C$_4$)-alkyl substituents, for example by methyl groups, which substituents can be located in any positions. Examples of such alkyl-substituted cycloalkyl groups are 1-methylcyclopropyl, 2,2-dimethylcyclopropyl, 1-methylcyclopentyl, 2,3-dimethylcyclopentyl, 1-methylcyclohexyl, 4-methylcyclohexyl, 4-isopropylcyclohexyl, 4-tert-butylcyclohexyl and 3,3,5,5-tetramethylcyclohexyl. As regards the optional substitution of cycloalkyl groups by one or more fluorine substituents, they can be unsubstituted, i.e. not carry fluorine substituents, or substituted, for example by one, two, three, four, five, six, seven, eight, nine, ten or eleven fluorine substituents, or by one, two, three, four, five or six fluorine substituents, or by one, two, three or four fluorine substituents, or by one or two fluorine substituents. The fluorine substituents can be located in any positions of the cycloalkyl group and can also be located in an alkyl substituent on the cycloalkyl group. Examples of fluoro-substituted cycloalkyl groups are 1-fluorocyclopropyl, 2,2-difluorocyclopropyl, 3,3-difluorocyclobutyl, 1-fluorocyclohexyl, 4,4-difluorocyclohexyl and 3,3,4,4,5,5-hexafluorocyclohexyl. Cycloalkyl groups can also be substituted simultaneously by fluorine and alkyl. Halogen is fluorine, chlorine, bromine or iodine. In one embodiment of the invention, halogen in any occurrence in the compounds of the formula I, independently of all other occurrences, is fluorine, chlorine or bromine, in another embodiment fluorine or chlorine, in another embodiment fluorine.

An oxo substituent, i.e. an oxygen atom which is bonded via a double bond, when bonded to a carbon atom, replaces two hydrogen atoms on the carbon atom of the parent system to which it is bonded. Thus, if a CH$_2$ group is substituted by oxo, it becomes a carbonyl group (C(O), C=O). An oxo substituent cannot be present on a carbon atom in an aromatic ring.

The present invention comprises all stereoisomeric forms of the compounds of the formula I, for example all enantiomers and diastereomers including cis/trans isomers. The invention likewise comprises mixtures of two or more stereoisomeric forms, for example mixtures of enantiomers and/or diastereomers including cis/trans isomers, in all ratios. Asymmetric centers contained in the compounds of the formula I, for example in unsubstituted or substituted alkyl groups, can all independently of each other have the S configuration or the R configuration. The invention relates to enantiomers, both the levorotatory and the dextrorotatory antipode, in enantiomerically pure form and essentially enantiomerically pure form, for example with a molar ratio of the two enantiomers of 99:1 or greater, and in the form of racemates and in the form of mixtures of the two enantiomers in all ratios. The invention likewise relates to diastereomers in the form of pure and essentially pure diastereomers and in the form of mixtures of two or more diastereomers in all ratios. The invention also comprises all cis/trans isomers of the compounds of the formula I in pure form and essentially pure form, for example with a molar ratio of the cis/trans isomers of 99:1 or greater, and in the form of mixtures of the cis isomer and the trans isomer in all ratios. Cis/trans isomerism can occur in substituted rings. The preparation of individual stereoisomers, if desired, can be carried out by resolution of a mixture according to customary methods, for example, by chromatography or crystallization, or by use of stereochemically uniform starting compounds in the synthesis or by stereoselective reactions. Optionally, before a separation of stereoisomers a derivatization can be carried out. The separation of a mixture of stereoisomers can be carried out at the stage of the compound of the formula I or at the stage of an intermediate in the course of the synthesis. The invention also comprises all tautomeric forms of the compounds of the formula I.

Physiologically acceptable salts, including pharmaceutically utilizable salts, of the compounds of the formula I generally comprise a nontoxic salt component. They can contain inorganic or organic salt components. Such salts can be formed, for example, from compounds of the formula I which contain an acidic group, for example a carboxylic acid group (hydroxycarbonyl group, HO—C(O)—), and nontoxic inorganic or organic bases. Suitable bases are, for example, alkali metal compounds or alkaline earth metal compounds, such as sodium hydroxide, potassium hydroxide, sodium carbonate or sodium hydrogencarbonate, or ammonia, organic amino compounds and quaternary ammonium hydroxides. Reactions of compounds of the formula I with bases for the preparation of the salts are in general carried out according to customary procedures in a solvent or diluent. Examples of salts of acidic groups thus are sodium, potassium, magnesium or calcium salts or ammonium salts which can also carry one or more organic groups on the nitrogen atom. Compounds of the formula I which contain a basic, i.e. protonatable, group, for example an amino group or a basic heterocycle, can be present in the form of their acid addition salts with physiologically acceptable acids, for example as salt with hydrogen chloride, hydrogen bromide, phosphoric acid, sulfuric acid, acetic acid, benzoic acid, methanesulfonic acid, p-toluenesulfonic acid, which in general can be prepared from the compounds of the formula I by reaction with an acid in a solvent or diluent according to customary procedures. If the compounds of the formula I simultaneously contain an acidic and a basic group in the molecule, the invention also includes internal salts (betaines, zwitterions) in addition to the salt forms mentioned. The present invention also comprises all salts of the compounds of the formula I which, because of low physiological tolerability, are not directly suitable for use as a pharmaceutical, but are suitable as intermediates for chemical reactions or for the preparation of physiologically acceptable salts, for example by means of anion exchange or cation exchange. The present invention also comprises all solvates of the compounds of the formula I and their salts, including physiologically acceptable solvates, such as hydrates, i.e. adducts with water, and adducts with alcohols like $(C_1-C_4)$-alkanols, as well as active metabolites of compounds of the formula I and prodrugs of the compounds of the formula I, i.e. compounds which in vitro may not necessarily exhibit pharmacological activity but which in vivo are converted into pharmacologically active compounds of the formula I, for example compounds which are converted by metabolic hydrolysis into a compound of the formula I, such as compounds in which a carboxylic acid group is present in esterified form or in the form of an amide.

A subject of the invention are all compounds of the formula I wherein any one or more structural elements such as groups, substituents and numbers are defined as in any of the specified embodiments or definitions of the elements or have one or more of the specific meanings which are mentioned herein as examples of elements, wherein all combinations of one or more specified embodiments and/or definitions and/or specific meanings of the elements are a subject of the present invention. Also with respect to all such compounds of the formula I, all their stereoisomeric forms and mixtures of stereoisomeric forms in any ratios, and their physiologically acceptable salts, and the physiologically acceptable solvates of any of them, are a subject of the present invention.

A subject of the invention also is a compound of the formula I which is chosen from any of the specific compounds of the formula I which are disclosed herein, or is any one of the specific compounds of the formula I which are disclosed herein, irrespective thereof whether they are disclosed as a free compound and/or as a specific salt, or a physiologically acceptable salt thereof, or a physiologically acceptable solvate of any of them, wherein the compound of the formula I is a subject of the invention in any of its stereoisomeric forms or a mixture of stereoisomeric forms in any ratio.

Another subject of the present invention are the novel starting compounds and intermediates occurring in the synthesis of the compounds of the formula I, in any of their stereoisomeric forms or a mixture of stereoisomeric forms in any ratio, and their salts, and solvates of any of them, and their use as synthetic intermediates or starting compounds. All general explanations, specifications of embodiments and definitions of numbers and groups given above with respect to the compounds of the formula I apply correspondingly to the said intermediates and starting compounds. A subject of the invention are in particular the novel specific starting compounds and intermediates described herein. Independently thereof whether they are described as a free compound and/or as a specific salt, they are a subject of the invention both in the form of the free compounds and in the form of their salts, and if a specific salt is described, additionally in the form of this specific salt.

The compounds of the formula I inhibit the protease cathepsin A as can be demonstrated in the pharmacological test described below and in other tests which are known to a person skilled in the art. The compounds of the formula I and their physiologically acceptable salts and solvates therefore are valuable pharmaceutical active compounds. The compounds of the formula I and their physiologically acceptable salts and solvates can be used for the treatment of cardiovascular diseases such as heart failure including systolic heart failure, diastolic heart failure, diabetic heart failure and heart failure with preserved ejection fraction, cardiomyopathy, myocardial infarction, left ventricular dysfunction including left ventricular dysfunction after myocardial infarction, cardiac hypertrophy, myocardial remodeling including myocardial remodeling after infarction or after cardiac surgery, valvular heart diseases, vascular hypertrophy, vascular remodeling including vascular stiffness, hypertension including pulmonary hypertension, portal hypertension and systolic hypertension, atherosclerosis, peripheral arterial occlusive disease (PAOD), restenosis, thrombosis and vascular permeability disorders, ischemia and/or reperfusion damage including ischemia and/or reperfusion damage of the heart and ischemia and/or reperfusion damage of the retina, inflammation and inflammatory diseases such as rheumatoid arthritis and osteoarthritis, renal diseases such as renal papillary necrosis and renal failure including renal failure after ischemia/reperfusion, pulmonary diseases such as cystic fibrosis, chronic bronchitis, chronic obstructive pulmonary disease (COPD), asthma, acute respiratory dystress syndrome (ARDS), respiratory tract infections and lung carcinoma, immunological diseases, diabetic complications including diabetic nephropathy and diabetic cardiomyopathy, fibrotic diseases such as pulmonary fibrosis including idiopathic lung fibrosis, cardiac fibrosis, vascular fibrosis, perivascular fibrosis, renal fibrosis including renal tubulointerstitial fibrosis, fibrosing skin conditions including keloid formation, collagenosis and scleroderma, and liver fibrosis, liver diseases such as liver cirrhosis, pain such as neuropathic pain, diabetic pain and inflammatory pain, macular degeneration, neurodegenerative diseases or psychiatric disorders, or for cardioprotection including cardioprotection after myocardial infarction and after cardiac surgery, or for renoprotection, for example. The compounds of the formula I and their physiologically acceptable salts and solvates can be used as a diuretic (stand-alone treatment or in combination with established diuretics). The compounds of the formula I and their physiologically acceptable salts and solvates can also be used for treatment and/or prevention of atrial fibrillation. The treatment of diseases is to be understood as meaning both the therapy of existing pathological changes or malfunctions of the organism or of existing symptoms with the aim of relief, alleviation or cure, and the prophylaxis or prevention of pathological changes or malfunctions of the organism or of symptoms in humans or animals which are susceptible thereto and are in need of such a prophylaxis or prevention, with the aim of a prevention or suppression of their occurrence or of an attenuation in the case of their occurrence. For example, in patients who on account of their disease history are susceptible to myocardial infarction, by means of the prophylactic or preventive medicinal treatment the occurrence or re-occurrence of a myocardial infarction can be prevented or its extent and sequelae decreased, or in patients who are susceptible to attacks of asthma, by means of the prophylactic or preventive medicinal treatment such attacks can be prevented or their severity decreased. The treatment of diseases can occur both in acute cases and in chronic cases. The efficacy of the compounds of the formula I can be demonstrated in the pharmacological test described below and in other tests which are known to a person skilled in the art.

The compounds of the formula I and their physiologically acceptable salts and solvates can therefore be used in animals, in particular in mammals and specifically in humans, as a pharmaceutical or medicament on their own, in mixtures with one another or in the form of pharmaceutical compositions. A subject of the present invention also are the compounds of the formula I and their physiologically acceptable salts and solvates for use as a pharmaceutical, as well as pharmaceutical compositions and medicaments which comprise an efficacious dose of at least one compound of the formula I and/or a physiologically acceptable salt thereof and/or solvate thereof as an active ingredient and a pharmaceutically acceptable carrier, i.e. one or more pharmaceutically innocuous, or non-hazardous, vehicles and/or excipients, and optionally one or more other pharmaceutical active compounds. A subject of the present invention furthermore are the compounds of the formula I and their physiologically acceptable salts and solvates for use in the treatment of the diseases mentioned above or below, including the treatment of any one of the mentioned diseases, for example the treatment of heart failure, myocardial infarction, cardiac hypertrophy, diabetic nephropathy, diabetic cardiomyopathy, cardiac fibrosis, or ischemia and/or reperfusion damage, or for cardioprotection, the use of the compounds of the formula I and their physiologically acceptable salts and solvates for the manufacture of a medicament for the treatment of the diseases mentioned above or below, including the treatment of any one of the mentioned diseases, for example the treatment of heart failure, myocardial infarction, cardiac hypertrophy, diabetic nephropathy, diabetic cardiomyopathy, cardiac fibrosis, or ischemia and/or reperfusion damage, or for cardioprotection, wherein the treatment of diseases comprises their therapy and prophylaxis as mentioned above, as well as their use for the manufacture of a medicament for the inhibition of cathepsin A. A subject of the invention also are methods for the treatment of the diseases mentioned above or below, including the treatment of any one of the mentioned diseases, for example the treatment of heart failure, myocardial infarction, cardiac hypertrophy, diabetic nephropathy, diabetic cardiomyopathy, cardiac fibrosis, or ischemia and/or reperfusion damage, or for cardioprotection, which comprise administering an efficacious amount of at least one compound of the formula I and/or a physiologically acceptable salt thereof and/or solvate thereof to a human or an animal which is in need thereof. The compounds of the formula I and pharmaceutical compositions and medicaments comprising them can be administered enterally, for example by oral, sublingual or rectal administration, parenterally, for example by intravenous, intramuscular, subcutaneous or intraperitoneal injection or infusion, or by another type of administration such as topical, percutaneous, transdermal, intra-articular or intraocular administration.

The compounds of the formula I and their physiologically acceptable salts and solvates can also be used in combination with other pharmaceutical active compounds, wherein in such a combination use the compounds of the formula I and/or their physiologically acceptable salts and/or solvates and one or more other pharmaceutical active compounds can be present in one and the same pharmaceutical composition or in two or more pharmaceutical compositions for separate, simultaneous or sequential administration. Examples of such other pharmaceutical active compounds are diuretics, aquaretics, angiotensin converting enzyme (ACE) inhibitors, angiotensin receptor blockers, renin inhibitors, beta blockers, digoxin, aldosterone antagonists, NO donors, nitrates, hydralazines, ionotropes, vasopressin receptor antagonists, soluble guanylate cyclase activators, statins, peroxisome proliferator-activated receptor-alpha (PPAR-α) activators, peroxisome proliferator-activated receptor-gamma (PPAR-γ) activators, rosiglitazone, pioglitazone, metformin, sulfonylureas, glucagon-like peptide 1 (GLP-1) agonists, dipeptidyl peptidase IV (DPPIV) inhibitors, insulins, anti-arrhythmics, endothelin receptor antagonists, calcium antagonists, phosphodiesterase inhibitors, phosphodiesterase type 5 (PDE5) inhibitors, factor II/factor IIa inhibitors, factor IX/factor IXa inhibitors, factor X/factor Xa inhibitors, factor XIII/factor XIIIa inhibitors, heparins, glycoprotein IIb/IIIa antagonists, P2Y12 receptor antagonists, clopidogrel, coumarins, cyclooxygenase inhibitors, acetylsalicylic acid, RAF kinase inhibitors and p38 mitogen-activated protein kinase inhibitors. A subject of the present invention also is the said combination use of any one or more of the compounds of the formula I disclosed herein and their physiologically acceptable salts and solvates, with any one or more, for example one or two, of the mentioned other pharmaceutical active compounds.

The pharmaceutical compositions and medicaments according to the invention normally contain from about 0.5 to about 90 percent by weight of compounds of the formula I and/or physiologically acceptable salts and/or solvates thereof, and an amount of active ingredient of the formula I and/or its physiologically acceptable salt and/or solvate which in general is from about 0.2 mg to about 1.5 g, particularly from about 0.2 mg to about 1 g, more particularly from about 0.5 mg to about 0.5 g, for example from about 1 mg to about 0.3 g, per unit dose. Depending on the kind of the pharmaceutical composition and other particulars of the specific case, the amount may deviate from the indicated ones. The production of the pharmaceutical compositions and medicaments can be carried out in a manner known per se. For this, the compounds of the formula I and/or their physiologically acceptable salts and/or solvates are mixed together with one or more solid or liquid vehicles and/or excipients, if desired also in combination with one or more other pharmaceutical active compounds such as those mentioned above, and brought into a suitable form for dosage and administration, which can then be used in human medicine or veterinary medicine.

As vehicles, which may also be looked upon as diluents or bulking agents, and excipients suitable organic and inorganic substances can be used which do not react in an undesired manner with the compounds of the formula I. As examples of types of excipients, or additives, which can be contained in the pharmaceutical compositions and medicaments, lubricants, preservatives, thickeners, stabilizers, disintegrants, wetting agents, agents for achieving a depot effect, emulsifiers, salts, for example for influencing the osmotic pressure, buffer substances, colorants, flavorings and aromatic substances may be mentioned. Examples of vehicles and excipients are water, vegetable oils, waxes, alcohols such as ethanol, isopropanol, 1,2-propanediol, benzyl alcohols, glycerol, polyols, polyethylene glycols or polypropylene glycols, glycerol triacetate, polyvinylpyrrolidone, gelatin, cellulose, carbohydrates such as lactose or starch like corn starch, sodium chloride, stearic acid and its salts such as magnesium stearate, talc, lanolin, petroleum jelly, or mixtures thereof, for example saline or mixtures of water with one or more organic solvents such as mixtures of water with alcohols. For oral and rectal use, pharmaceutical forms such as, for example, tablets, film-coated tablets, sugar-coated tablets, granules, hard and soft gelatin capsules, suppositories, solutions, including oily, alcoholic or aqueous solutions, syrups, juices or drops, furthermore suspensions or emulsions, can be used. For parenteral use, for example by injection or infusion, pharmaceutical forms such as solutions, for example aqueous solutions, can be used. For topical use, pharmaceutical forms such as ointments, creams, pastes, lotions, gels, sprays, foams, aerosols, solutions or powders can be used. Further suitable pharmaceutical forms are, for example, implants and patches and forms adapted to inhalation. The compounds of the formula I and their physiologically acceptable salts can also be lyophilized and the obtained lyophilizates used, for example, for the production of injectable compositions. In particular for topical application, also liposomal compositions are suitable. The pharmaceutical compositions and medicaments can also contain one or more other active ingredients and/or, for example, one or more vitamins.

As usual, the dosage of the compounds of the formula I depends on the circumstances of the specific case and is adjusted by the physician according to the customary rules and procedures. It depends, for example, on the compound of the formula I administered and its potency and duration of action, on the nature and severity of the individual syndrome, on the sex, age, weight and the individual responsiveness of the human or animal to be treated, on whether the treatment is acute or chronic or prophylactic, or on whether further pharmaceutical active compounds are administered in addition to a compound of the formula I. Normally, in the case of administration to an adult weighing about 75 kg, a dose from about 0.1 mg to about 100 mg per kg per day, in particular from about 1 mg to about 20 mg per kg per day, for example from about 1 mg to about 10 mg per kg per day (in each case in mg per kg of body weight), is administered. The daily dose can be administered in the form of a single dose or divided into a number of individual doses, for example two, three or four individual doses. The administration can also be carried out continuously, for example by continuous injection or infusion.

Depending on the individual behavior in a specific case, it may be necessary to deviate upward or downward from the indicated dosages.

Besides as a pharmaceutical active compound in human medicine and veterinary medicine, the compounds of the formula I can also be employed as an aid in biochemical investigations or as a scientific tool or for diagnostic purposes, for example in in-vitro diagnoses of biological samples, if an inhibition of cathepsin A is intended. The compounds of the formula I and their salts can also be used as intermediates, for example for the preparation of further pharmaceutical active substances.

The following examples illustrate the invention.

ABBREVIATIONS

ACN acetonitrile
DCM dichloromethane
DMF N,N-dimethylformamide
DMSO dimethyl sulfoxide
EA ethyl acetate
EDIA N-ethyl-diisopropylamine
FA formic acid
MOH methanol
NEM N-ethyl-morpholine
TFA trifluoroacetic acid
THF tetrahydrofuran
TOTU O-(cyano(ethoxycarbonyl)methyleneamino)-N,N,N',N'-tetramethyluronium tetrafluoroborate When example compounds containing a basic group were purified by preparative high pressure liquid chromatography (HPLC) on reversed phase (RP) column material and, as customary, the eluent was a gradient mixture of water and acetonitrile containing trifluoroacetic acid, they were in part obtained in the form of their acid addition salts with trifluoroacetic acid, depending on the details of the work-up such as evaporation or lyophilization conditions. In the names of the example compounds and the structural formulae such contained trifluoroacetic acid is not specified. Likewise are other acid components of example compounds obtained in the form of an acid addition salt in general not specified in the name and the formula.

The prepared compounds were in general characterized by spectroscopic data and chromatographic data, in particular mass spectra (MS) and HPLC retention times (Rt; in min) which were obtained by combined analytical HPLC/MS characterization (LC/MS), and/or nuclear magnetic resonance (NMR) spectra. Unless specified otherwise, $^1$H-NMR spectra were recorded at 500 MHz in $D_6$-DMSO as solvent at 298 K. In the NMR characterization, the chemical shift δ (in ppm), the number of hydrogen atoms (H), and the multiplicity (s: singlet, d: doublet, dd: doublet of doublets, t: triplet, q: quartet, m: multiplet) of the peaks as determined from the graphically depicted spectra are given. In the MS characterization, in general the mass number (m/z) of the peak of the molecular ion [M], for example [M$^+$], or of a related ion such as the ion [M+1], for example [(M+1)$^+$], i.e. the protonated molecular ion [(M+H)$^+$], or the ion [M−1], for example [(M−1)$^-$], i.e. the deprotonated molecular ion [(M−H)$^-$], which was formed depending on the ionization method used, is given. Generally, the ionization method was electrospray ionization (ES). The particulars of the LC/MS methods used are as follows.

Method LC1

Column: Waters UPLC BEH C18, 50×2.1 mm, 1.7 μm; flow: 0.9 ml/min; 55° C.; eluent A: water+0.05% FA; eluent B: ACN+0.035% FA; gradient: from 98% A+2% B to 5% A+95% B within 2.0 min, then 5% A+95% B for 0.6 min, then to 95% A+5% B within 0.1 min, then 95% A+5% B for 0.3 min; MS ionization method: ES$^+$ Method LC2

Column: Waters XBridge C18, 50×4.6 mm, 2.5 μm; flow: 1.7 ml/min; 40° C.; eluent A: water+0.05% TFA; eluent B: ACN+0.05% TFA; gradient: 95% A+5% B for 0.2 min, then to 5% A+95% B within 2.2 min, then 5% A+95% B for 0.8 min, then to 95% A+5% B within 0.1 min, then 95% A+5% B for 0.7 min; MS ionization method: ES$^+$

EXPERIMENTAL

In general the compounds of formula I are synthesized according to one of the general schemes below:

Scheme A

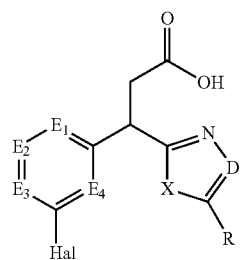

Hal = Cl, Br, I

A

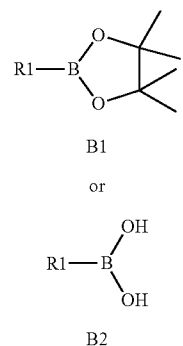

B1 or

R1—B(OH)₂

B2

Suzuki-Coupling →

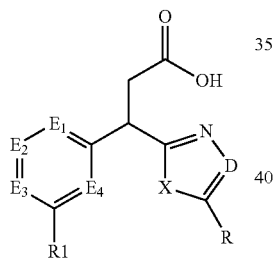

C

Scheme B

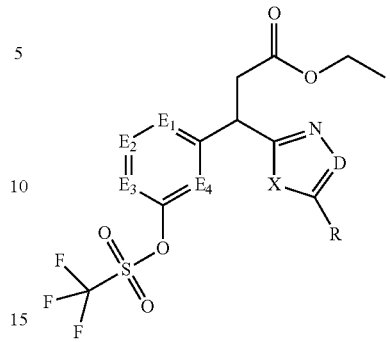

D

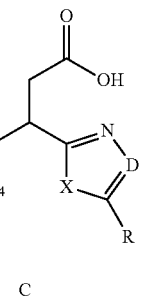

B1 or

R1—B(OH)₂

B2

1) Suzuki-Coupling
2) Ester Hydrolysis →

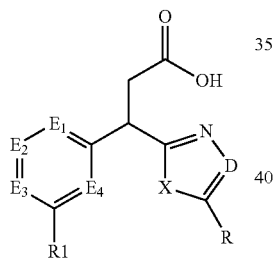

C

And General Procedure A:

0.3 mmol boronic acid is placed in a reaction tube, 0.2 mmol of the intermediate A dissolved in 2 ml of DMF and 0.8 mmol Cs2CO3 dissolved in 1 ml water is added and the reaction tube purged with Ar. After the addition of 0.02 mmol Pd[PPh3]Cl2 is reaction mixture is heated overnight at 95° C.

The reaction mixture is adjusted to pH=5 with 2N HCl, 15 ml EtOAc and 5 ml 5% NaCl solution are added, the organic phase is separated and dried over Na2SO4. The solvent is removed in vacuo and the crude product subjected to HPLC chromatography. Yields are in the range from 10 to 95%.

And General Procedure B 0.3 mmol boronic acid is placed in a reaction tube, 0.2 mmol of the intermediate D dissolved in 2 ml of DMF and 0.8 mmol Cs2CO3 dissolved in 1 ml water is added and the reaction tube purged with Ar. After the addition of 0.02 mmol Pd[PPh3]Cl2 is reaction mixture is heated overnight at 95° C.

The reaction mixture is adjusted to pH=5 with 2N HCl, 15 ml EtOAc and 5 ml 5% NaCl solution are added, the organic phase is separated and dried over Na2SO4. The solvent is removed in vacuo, the crude product is dissolved in 2 ml EtOH and 0.5 ml 1N NaOH is added. After stirring overnight at RT the solvent is removed and the isolated material is subjected to HPLC chromatography. Yields are in the range from 10 to 95%

The Suzuki reactions described above can be carried out by all procedures well known to a person skilled in the art and described for example in M. Mora et. al. Current Organic Chemistry 2012, 1128-1150

Solvents other than DMF like isopropanol, toluene, dioxane, THF, acetonitrile, water or any combinations of them might be used, the reaction is also possible by using ionic liquids. Any combination of a palladium salt and ligand or any preformed palladium catalyst system can be applied for these reactions. Polymer-bound Pd-catalysts or polymer-bound ligands may also be used. As base one might use $Na_2CO_3$, $K_2CO_3$, $AgCO_3$ or CsF instead of $Cs_2CO_3$. The reaction temperatures are in the range from 40° C. to 150° C. and may be reached by thermal heating or by using a microwave reactor for a period from 5 minutes to 48 hours.

In scheme B one can isolate the product of the Suzuki coupling from the first step prior to the formation of the final product by ester hydrolysis or one can run both reactions in a one pot procedure without isolating the ester material. Instead of the ethyl ester in scheme B any other ester known to people skilled in the art may be used. Although instead of the triflate in scheme B one might use any other suitable leaving groups for Suzuki reactions.

Intermediates A are synthesized according to the general scheme C by addition of a metallated five-membered heterocycle F to an aromatic acid derivative E:E can be an aromatic acid ester, an aromatic acid chloride or a Weinreb amide of an aromatic carboxylic acid E. The resulting ketone G is subjected to a Wittig reaction and the Wittig condensation product H is reduced by applying Zn/HOAc and the ester residue is converted into the free acid A.

In the metallation step instead of n-BuLi tert-BuLi or MeLi a Grignard reagent like MeMgBr, iso-propyl-MgBr or iso-propyl-MgCl*LiCl may be used. To facilitate the addition to the intermediate E a transmetallation to another metal ion like copper or zinc might be necessary.

For the Wittig reaction one might use other strong bases instead of NaH like NaOtBu or KOtBu or phosphazene bases. And the reduction might be carried out using Zn in aq. HCl using a concentration of aq. HCl ranging from 0.01M to 12M or in diluted H2SO4.

Intermediates E might be commercially available or might be prepared in one step from the commercially available carboxylic acids Scheme C

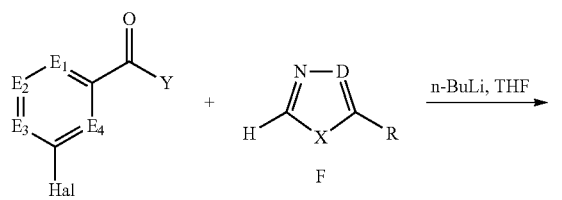

Y = Cl, OMe, NMeOMe
E

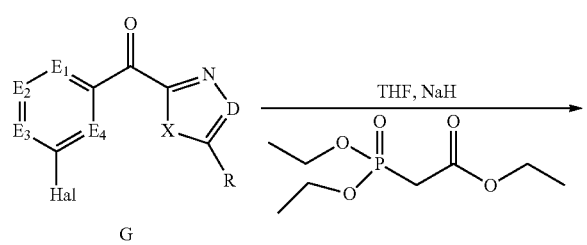

G

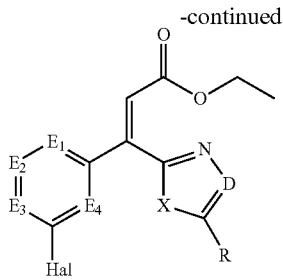

H

1) Zn, HOAc
2) NaOH, EtOH

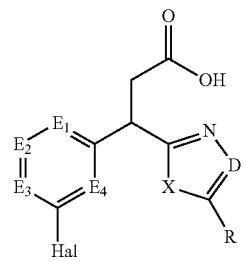

Hal = Cl, Br, I
A

Under certain circumstances the group Y might represent a hydrogen atom forming the aromatic aldehyde intermediate E-H. After the addition of the metallated heterocycle F the corresponding alcohol I can be oxidized to the desired intermediate G by using MnO2 or other oxidants like KMnO4, CrO3, and H2O2.

Scheme D

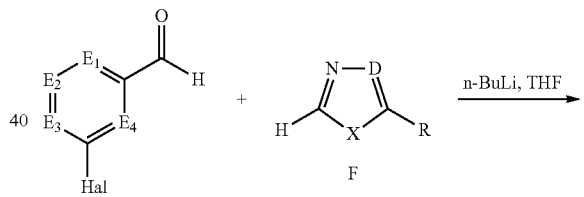

E-H

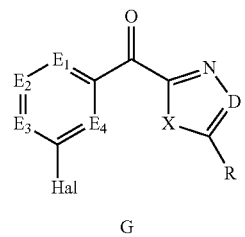

I

G

In an alternative approach to the synthesis described in scheme C, the residue Hal in building block E might be replaced by a benzyloxy-residue leading to building block M. When the reduction of the CC-double bond of the Wittig condensation product O is carried out with Pd/C and H2 the benzyl residue is removed at the same time.

Conversion of the newly formed aromatic hydroxy group into the triflate furnishes intermediate P, a suitable starting material for palladium catalyzed cross-couplings. The starting materials M can be obtained from aromatic carboxylic acid esters having a free hydroxy substituent like J. The hydroxy substituent is alkylated with benzylbromide, benzyl chloride or benzyl iodide or any other benzyl derivative capable of undergoing a nucleophilic substitution reaction with an aromatic hydroxy group. Depending on the reactivity of the intermediate L towards the metallation reaction, L might be converted into the corresponding derivatives M by standard procedures well known to a person skilled in the art.

Scheme E

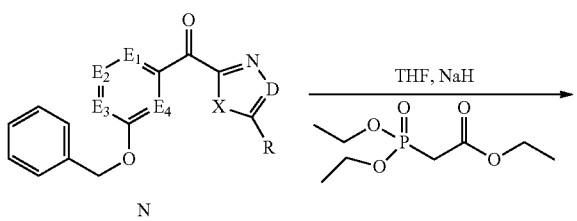

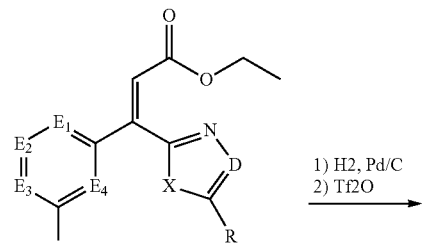

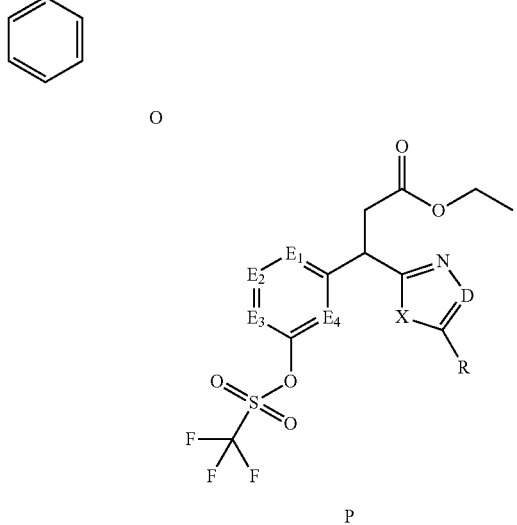

Synthesis of Intermediate P1

3-(5-methylthiazol-2-yl)-3-(6-(trifluoromethyl-sulfonyloxy)pyridin-2-yl)propanoate

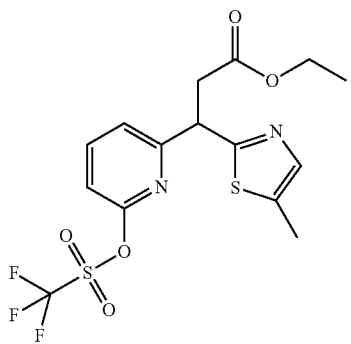 [SMILES: CCOC(=O)CC(c1cccc(OS(=O)(=O)C(F)(F)F)n1)c1ncc(C)s1]

Step 1: Synthesis of methyl 6-hydroxypicolinate

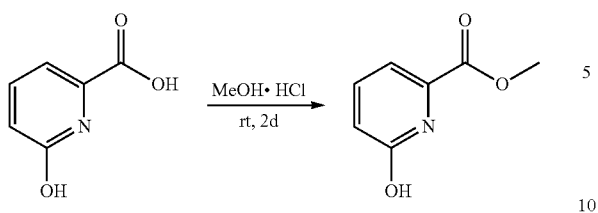

To a solution of 6-hydroxypicolinic acid (13.0 g, 93.5 mmol) in methanol (150 mL) at room temperature was added HCl in dioxane (4N, 10 mL). The resulting mixture was stirred at room temperature for 48 hours. The reaction mixture was concentrated to give methyl 6-hydroxypicolinate (13 g, 90%) as a white solid.

Synthesis of methyl 6-(benzyloxy)picolinate

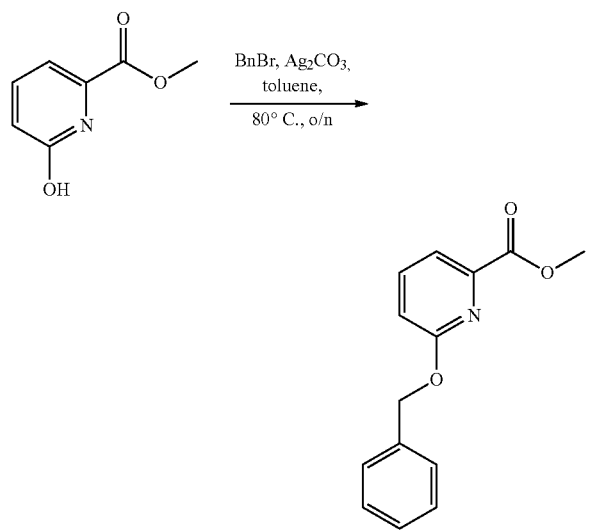

A mixture of methyl 6-hydroxypicolinate (3.06 g, 20.0 mmol), (bromomethyl)benzene (6.84 g, 40.0 mmol), and silver carbonate (11 g, 40 mmol) in toluene (150 mL) was stirred at 80° C. overnight. After cooling and filtration, the filtrate was concentrated under reduced pressure. The residue was purified by silica gel column chromatography eluting with petroleum ether/ethyl acetate (20:1) to give methyl 6-(benzyloxy)picolinate (2.6 g, 53%) as a white solid.

Synthesis of (6-(benzyloxy)pyridin-2-yl)(5-methylthiazol-2-yl)methanone

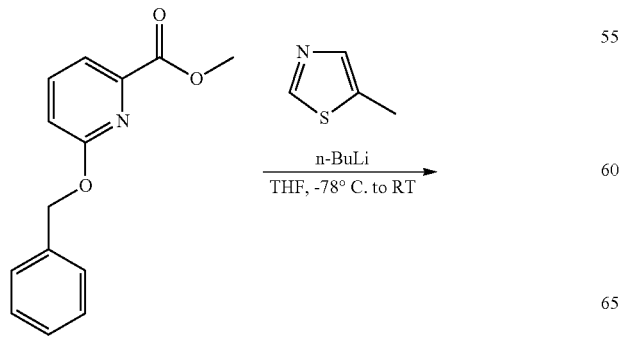

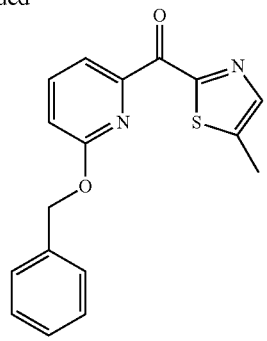

To a solution of n-BuLi (2.5 M in hexane, 16 mL, 40 mmol) in dry THF (120 mL) at −78° C. was added 5-methylthiazole (4.17 g, 40 mmol) drop wise over 20 minutes under nitrogen atmosphere. The mixture was stirred at −78° C. for 2 hrs and a solution of methyl 6-(benzyloxy)picolinate (4.7 g, 20 mmol) in THF (30 mL) was added drop wise over 20 minutes. After being stirred at −78° C. for 1 hr, the mixture was acidified with HCl (1N) to pH around 6 and extracted with ethyl acetate. The organic layer was concentrated and then diluted with MTBE. The white precipitate was collected by filtration to give A030-4. The remaining filtrate was concentrated. The residue was purified by silica gel chromatography eluting with petroleum ether/ethyl acetate (10/1) to afford A030-4. Total 6.2 g of (6-(benzyloxy)pyridin-2-yl)(5-methylthiazol-2-yl)methanone (85% yield) was obtained as a white solid.

$^1$H NMR (400 MHz, CDCl$_3$) δ 8.00 (d, J=7.2 Hz, 1H), 7.89 (s, 1H), 7.82 (t, J=8.0 Hz, 1H), 7.51-7.36 (m, 5H), 7.01 (d, J=8.0 Hz, 1H), 5.56 (s, 2H), 2.60 (s, 3H).

Synthesis of (Z)-ethyl 3-(6-(benzyloxy)pyridin-2-yl)-3-(5-methylthiazol-2-yl)acrylate

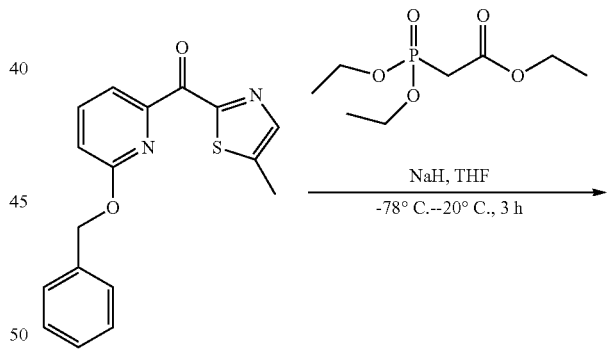

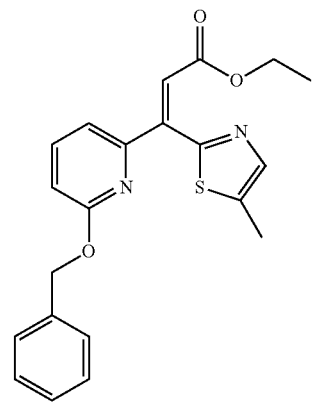

To a suspension of NaH (60%, 1.3 g, 33 mmol) in dry THF (200 mL) at −78° C. was added ethyl 2-(diethoxyphosphoryl)acetate (7.5 g, 33 mmol). After being stirred at −78° C. for 1 hour, a solution of (6-(benzyloxy)pyridin-2-yl)(5-methylthiazol-2-yl)methanone (3.47 g, 11.2 mmol) in THF (30 mL) was added drop wise over 30 minutes. After being stirred at −20 to −30° C. for 2 hours, the mixture was acidified with HCl (0.5 N) and then extracted with ethyl acetate. The organic layer was dried and concentrated. The residue was washed with MTBE and petroleum ether to afford (6-(benzyloxy)pyridin-2-yl)(5-methylthiazol-2-yl)methanone (6.2 g, 85% yield) as a white solid.

$^1$H NMR (400 MHz, CDCl$_3$) δ 7.58-7.25 (m, 8H), 6.80 (d, J=8.4 Hz, 1H), 6.75 (d, J=7.2 Hz, 1H), 5.44 (s, 2H), 4.15 (q, J=3.2 Hz, 2H), 2.54 (s, 3H), 1.21 (t, J=3.2 Hz, 3H).

Synthesis of ethyl 3-(6-hydroxypyridin-2-yl)-3-(5-methylthiazol-2-yl)propanoate

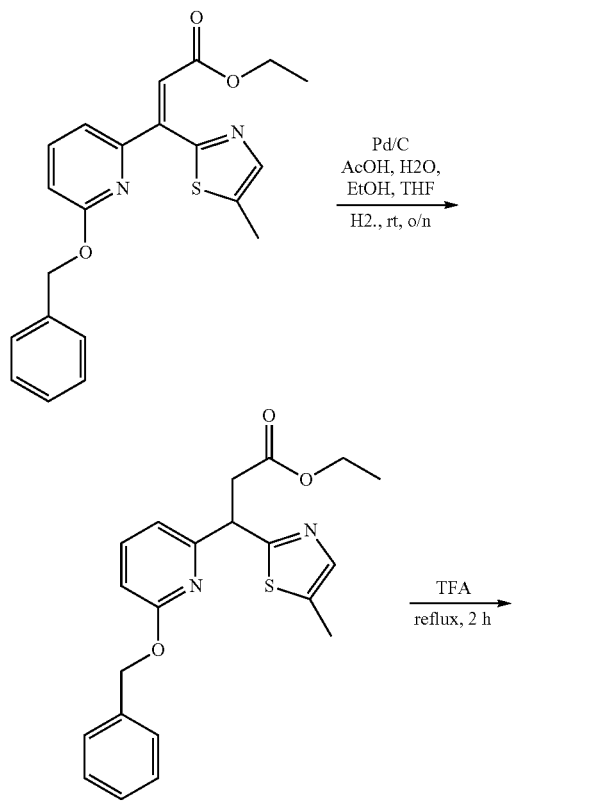

A mixture of (6-(benzyloxy)pyridin-2-yl)(5-methylthiazol-2-yl)methanone (8.0 g, 21 mmol), acetic acid (1.5 mL), H$_2$O (3 mL), and Pd/C (10%, 4 g) in ethanol (90 mL) and THF (60 mL) was stirred under H$_2$ atmosphere at room temperature overnight. After filtration through a pad of Celite and evaporation of the solvent, the residue was washed with MTBE and petroleum ether to afford A030-7 (3 g) as a white solid. The filtration (mixture of A030-6 and A030-7) was mixed with TFA (20 mL) and the resulting mixture was refluxed for 2 h. After cooling down, the mixture was treated with water and extracted with ethyl acetate. The organic layer was dried and concentrated. The residue was washed with MTBE and petroleum ether to afford ethyl 3-(6-hydroxypyridin-2-yl)-3-(5-methylthiazol-2-yl)propanoate (1.4 g, total 71%) as a white solid.

$^1$H NMR (400 MHz, CDCl$_3$) δ 7.40 (s, 1H), 7.34-7.30 (m, 1H), 6.46 (dd, J=9.2, 1.2 Hz, 1H), 6.14 (d, J=6.0 Hz, 1H), 4.63 (t, J=7.2 Hz, 1H), 4.13-4.07 (m, 2H), 3.25-3.19 (m, 1H), 3.05-2.97 (m, 1H), 2.43 (s, 3H), 1.19 (t, J=3.2 Hz, 3H).

Synthesis of ethyl 3-(5-methylthiazol-2-yl)-3-(6-(trifluoromethylsulfonyloxy)pyridin-2-yl)propanoate

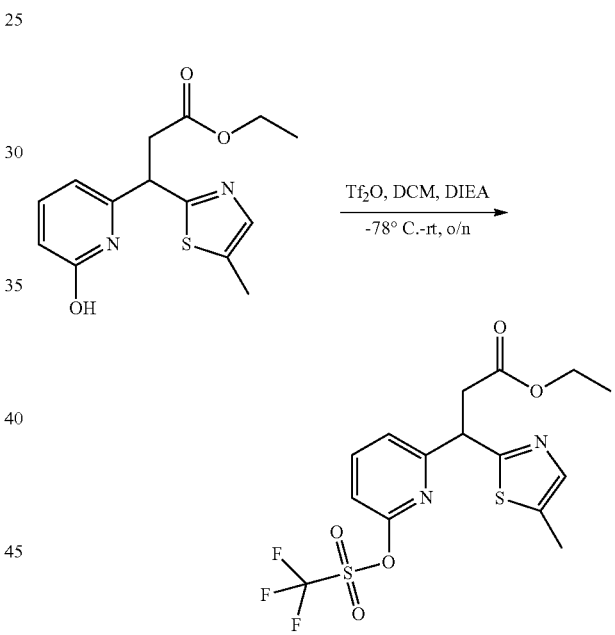

To a solution of ethyl 3-(6-hydroxypyridin-2-yl)-3-(5-methylthiazol-2-yl)propanoate (3.45 g, 11.8 mmol) in DCM (200 mL) at −78° C. was added trifluoromethanesulfonic anhydride (5.00 g, 17.7 mmol) and DIPEA (5.00 mL, 23.6 mmol) drop wise over 30 minutes. The resulting mixture was stirred at −78° C. for 30 minutes and warmed to room temperature overnight. The mixture was cooled to 0° C. and treated with water (100 mL). The organic layer was dried over Na$_2$SO$_4$ and concentrated. The oily residue was treated with ether and the solid was filtered off. The filtrate was concentrated to afford ethyl 3-(5-methylthiazol-2-yl)-3-(6-(trifluoromethylsulfonyloxy)pyridin-2-yl)propanoate (4.6 g, 93%) as brown oil.

$^1$H NMR (400 MHz, CDCl$_3$) δ 7.83 (t, J=7.6 Hz, 1H), 7.42 (d, J=7.6 Hz, 1H), 7.33 (s, 1H), 7.05 (d, J=8.4 Hz, 1H), 5.02-4.99 (m, 1H), 4.08 (q, J=3.2 Hz, 2H), 3.41-3.35 (m, 1H), 3.22-3.16 (m, 1H), 2.41 (s, 3H), 1.18 (t, J=3.2 Hz, 3H).

Synthesis of Intermediate P2

Ethyl 3-(5-methylthiazol-2-yl)-3-(5-(trifluoromethyl-sulfonyloxy)pyridin-3-yl)-propanoate

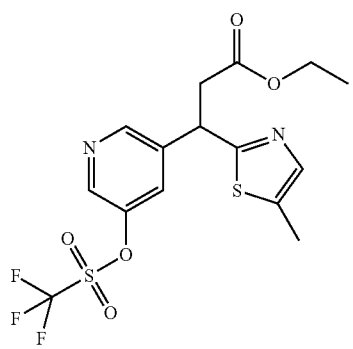 [SMILES: CCOC(=O)CC(c1cncc(OS(=O)(=O)C(F)(F)F)c1)c1ncc(C)s1]

Synthesis of methyl 5-hydroxynicotinate

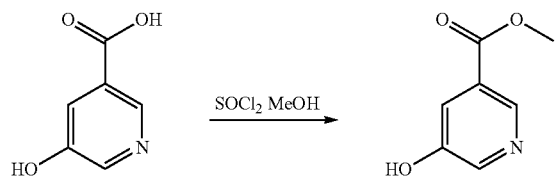

To a stirred solution of 5-hydroxynicotinic acid (10 g, 71.9 mmol) in MeOH (100 mL) was added sulfurous dichloride (1 mL) drop wise over 5 min. The resulting mixture was stirred at room temperature overnight. The resulted solution was added 100 mL of $NaHCO_3$. The precipitate was filtrated and washed with MeOH for several cycles to give 8.5 g of A031-2 (75% yields), which was used for the nest step without further purification.

Synthesis of methyl 5-(benzyloxy)nicotinate

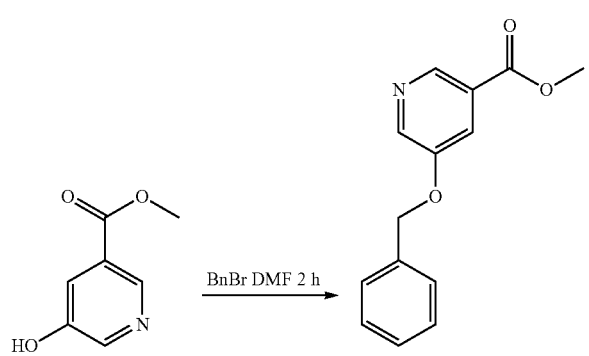 [SMILES: COC(=O)c1cncc(O)c1 ; COC(=O)c1cncc(OCc2ccccc2)c1]

To a stirred solution of methyl 5-hydroxynicotinate (8.5 g, 55.6 mmol) and $K_2CO_3$ (11.5 g, 83.3 mmol) in DMF (20 mL) at 0° C. was added (bromomethyl)benzene (8 mL, 66.7 mmol) drop wise over 5 min. The resulting mixture was stirred at room temperature for 2 hours. The mixture was quenched with water (100 mL) and extracted with EA (100 mL×3). The combined organic layers were washed with brine (100 mL), dried over $Na_2SO_4$. After filtration and evaporation of the solvent, the residue was purified by silica gel column chromatography eluting with petroleum ether/ethyl acetate (4:1) to give methyl 5-(benzyloxy)nicotinate (4 g, 30.7%) as a yellow oil.

Synthesis of (5-(benzyloxy)pyridin-3-yl)(5-methylthiazol-2-yl)methanone

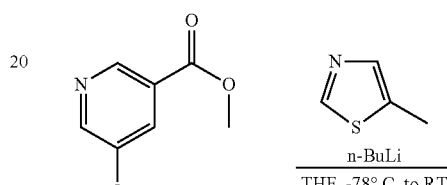

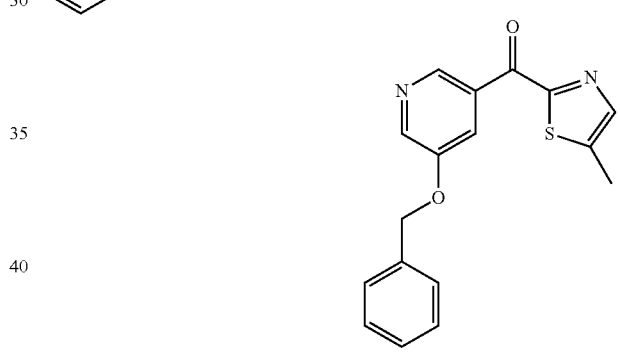

To a stirring mixture of 5-methylthiazole (3.3 g, 33 mmol) in dry THF (20 mL) was added n-BuLi (33 mmol 13.2 mL solution in hexanes,) drop wise over 10 minutes at −78° C. under nitrogen atmosphere. The mixture was stirred between −78° C. and −60° C. for 1.5 h and then cooled to −78° C. A solution of methyl 5-(benzyloxy)nicotinate (4.0 g, 16.5 mmol) in THF (10 mL) was added drop wise over 10 minutes. The resulting mixture was stirred at −78° C. for 30 minutes and warmed to room temperature with stirring overnight. The mixture was cooled to 0° C. and treated with water (50 mL). The resulting mixture was adjusted to pH around 6 with HCl (1N) and extracted with EA (100 mL×3). The combined organic layers were dried over $Na_2SO_4$, filtered, and concentrated under reduced pressure. The residue was purified by silica gel column chromatography eluting with petroleum ether/EtOAc (3:1) to afford (5-(benzyloxy)-2-methoxyphenyl)(thiazol-2-yl)methanone (3.2 g, 42%) as a yellow gel.

Synthesis of (Z)-ethyl 3-(5-(benzyloxy)pyridin-3-yl)-3-(5-methylthiazol-2-yl)acrylate

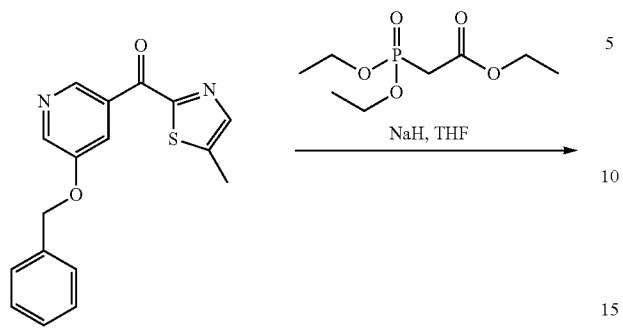

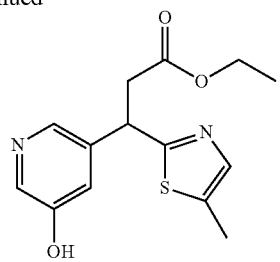

To a suspension of NaH (60%, 1.2 g, 30.9 mmol) in dry THF (20 mL) was added ethyl 2-(diethoxyphosphoryl)acetate (6.9 g, 30.9 mmol) at −78° C. After being stirred at −78° C. for 1 hour, a solution of (5-(benzyloxy)pyridin-3-yl)(5-methylthiazol-2-yl)methanone (3.2 g, 10.3 mmol) in THF (5 mL) was added drop wise over 30 min. The mixture was stirred at −78° C. for 30 min and then warmed to room temperature with stirring overnight. The mixture was cooled to 0° C. and treated with water (50 mL), pH value was adjusted to 6 with HCl (0.5 N) and extracted with EA (50 mL×3). The combined organic layers were dried over Na$_2$SO$_4$, filtered, and concentrated under reduced pressure. The residue was purified by silica gel chromatography eluting with petroleum ether/EtOAc (3:1) to afford (Z)-ethyl 3-(5-(benzyloxy)-2-methoxyphenyl)-3-(thiazol-2-yl)acrylate (3.1 g, 80.0%) as yellow gel.

Synthesis of ethyl 3-(5-hydroxypyridin-3-yl)-3-(5-methylthiazol-2-yl)propanoate

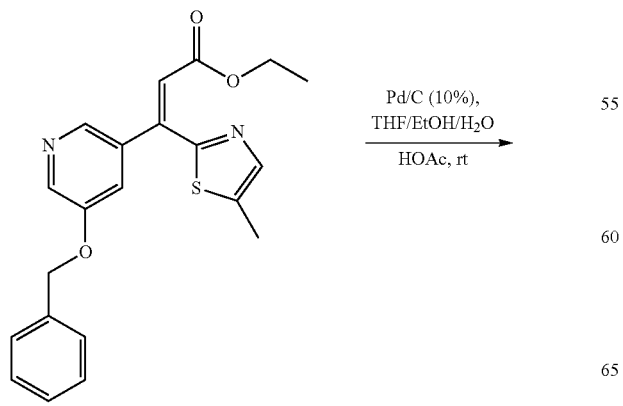

To a mixture of (Z)-ethyl 3-(5-(benzyloxy)pyridin-3-yl)-3-(5-methylthiazol-2-yl)acrylate (3.1 g, 8.2 mmol), HOAc (1.0 mL), and H$_2$O (2.0 mL) in EtOH (20 mL) and THF (10 mL) was added Pd/C (10%, dry, 820 mg) under H2 atmosphere. The mixture was stirred at room temperature under H$_2$ atmosphere for 48 hrs. After filtration through a pad of Celite and evaporation of the solvent, the residue was purified by silica gel chromatography eluting with petroleum ether/EtOAc (3:1) to afford 3-(5-hydroxypyridin-3-yl)-3-(5-methylthiazol-2-yl)propanoate (2.2 g, 92%) as a yellow-green gel.

Synthesis of ethyl 3-(5-methylthiazol-2-yl)-3-(5-(trifluoromethylsulfonyloxy)pyridin-3-yl)propanoate

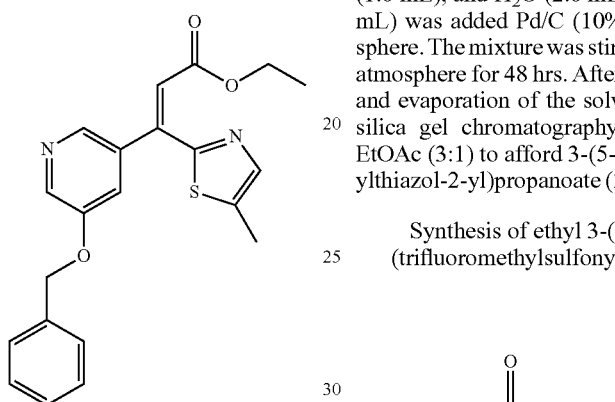

To a stirred solution of ethyl 3-(5-hydroxypyridin-3-yl)-3-(5-methylthiazol-2-yl)propanoate (2.2 g, 7.5 mmol) and Et$_3$N (1.52 g, 15.1 mmol) in DCM (20 mL) at −78° C. was added trifluoromethanesulfonic anhydride (2.3 g, 15.1 mmol) drop wise over 5 min. The resulting mixture was stirred at −78° C. for 30 minutes and warmed to room temperature with stirring overnight. The mixture was cooled to 0° C., treated with water (50 mL) and extracted with DCM (50 mL×3). The combined organic layers were washed with brine (50 mL), dried over Na$_2$SO$_4$, and concentrated. The residue was purified by silica gel column chromatography eluting with petroleum ether/ethyl acetate (4:1) to give ethyl 3-(2-methoxy-5-(trifluoromethylsulfonyloxy)phenyl)-3-(thiazol-2-yl)propanoate (900 mg, 28.0%) as yellow oil.

$^1$H NMR (400 MHz, MeOD) δ 8.71 (d, J=1.2 Hz, 1H), 8.58 (d, J=2.4 Hz, 1H), 7.96 (s, 1H), 7.43 (s, 1H), 5.02 (t, 1H), 4.10-4.05 (m, 2H), 3.43-3.37 (m, 1H), 3.22-3.15 (m, 1H), 2.45 (s, 3H), 1.18-1.14 (m, 3H).

Synthesis of Intermediate P3

3-(2-Methoxy-5-trifluoromethanesulfonyloxy-phenyl)-3-(5-methyl-thiazol-2-yl)-propionic acid ethyl ester

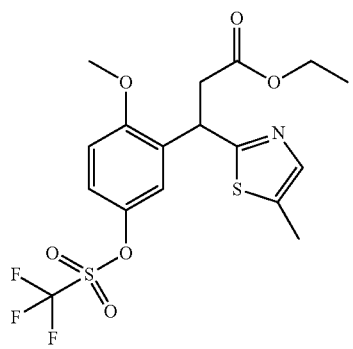 [SMILES: CCOC(=O)CC(c1ncc(C)s1)c1cc(OS(=O)(=O)C(F)(F)F)ccc1OC]

Methyl 5-(benzyloxy)-2-hydroxybenzoate

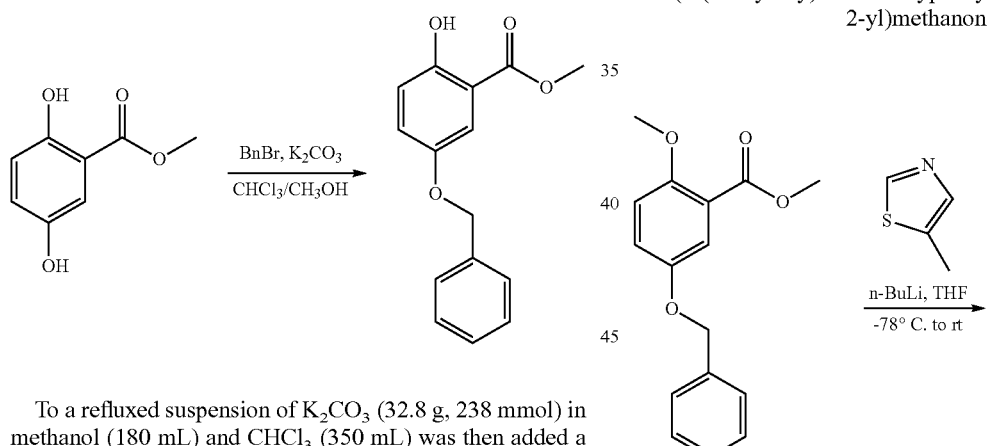

To a refluxed suspension of K$_2$CO$_3$ (32.8 g, 238 mmol) in methanol (180 mL) and CHCl$_3$ (350 mL) was then added a mixture of methyl 2,5-dihydroxybenzoate (10.0 g, 59.5 mmol) and bromomethylbenzene (7.10 mL, 59.5 mmol) in methanol/CHCl$_3$ (50 mL/25 mL) drop wise over 30 minutes. The resulting mixture was stirred at reflux for another 4 hours. After cooling down and filtration, the filter cake was washed with CHCl$_3$ (20 mL). The combined filtrate was concentrated under reduced pressure. The residue was redissolved in CHCl$_3$ (200 mL), washed with HCl (1N) (100 mL×2). The organic was then washed with brine (100 mL), dried over Na$_2$SO$_4$, filtered, and concentrated. The residue was purified by silica gel column chromatography eluting with petroleum ether/EtOAc (8:1) to give methyl 5-(benzyloxy)-2-hydroxybenzoate (10.6 g, 69.0%) as a white solid.

$^1$H NMR (500 MHz, DMSO-d$_6$) δ 10.09 (s, 1H), 7.43 (d, J=7.2 Hz, 2H), 7.40-7.36 (m, 2H), 7.34-7.32 (2H, m), 7.23 (dd, J=9.2, 3.2 Hz, 1H), 6.93 (d, J=9.2 Hz, 1H), 5.06 (s, 2H), 3.88 (s, 3H). NOESY showed the desired product as well.

Methyl 5-(benzyloxy)-2-methoxybenzoate

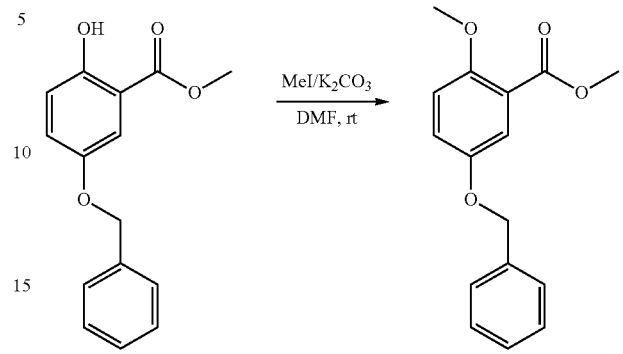

To a mixture of methyl 5-(benzyloxy)-2-hydroxybenzoate (10.6 g, 41.1 mmol) and K$_2$CO$_3$ (11.3 g, 82.2 mmol) in DMF (100 mL) was added iodomethane (2.60 mL, 49.3 mmol) drop wise over 5 minutes. The resulting mixture was stirred at room temperature overnight. The reaction mixture was poured into water (400 mL), filtered, and collected the solid. The solid was dissolved in EtOAc (300 mL), washed with water (50 mL) and brine (100 mL), dried over Na$_2$SO$_4$, filtered, and concentrated under reduced pressure to give methyl 5-(benzyloxy)-2-methoxybenzoate (10.4 g, 98%) as a yellow solid.

(5-(benzyloxy)-2-methoxyphenyl)(5-methylthiazol-2-yl)methanone

To a stirring mixture of 5-methylthiazole (3.80 g, 38.2 mmol) in dry THF (200 mL) was added n-BuLi (2.5 M in hexane, 15.3 mL, 38.2 mmol) drop wise over 20 minutes at −78° C. under nitrogen atmosphere. The mixture was stirred between −78° C. and −60° C. for 1.5 h and then cooled to −78° C. A solution of methyl 5-(benzyloxy)-2-methoxybenzoate (10.4 g, 38.2 mmol) in THF (50 mL) was added drop wise over 30 minutes. The resulting mixture was stirred at −78° C. for 30 minutes and warmed to room temperature with stirring overnight. The mixture was cooled to 0° C. and treated with water (50 mL). The resulting mixture was adjusted to pH around 6 with HCl (1N). The organic layer was dried over Na₂SO₄, filtered, and concentrated under reduced pressure. The residue was purified by silica gel column chromatography eluting with petroleum ether/EtOAc (3:1) to afford (5-(benzyloxy)-2-methoxyphenyl)(5-methylthiazol-2-yl) methanone (2.5 g, 19%) as a yellow gel. 3.0 g of starting material methyl 5-(benzyloxy)-2-methoxybenzoate was recovered.

Synthesis of (Z)-ethyl 3-(5-(benzyloxy)-2-methoxyphenyl)-3-(5-methylthiazol-2-yl)acrylate

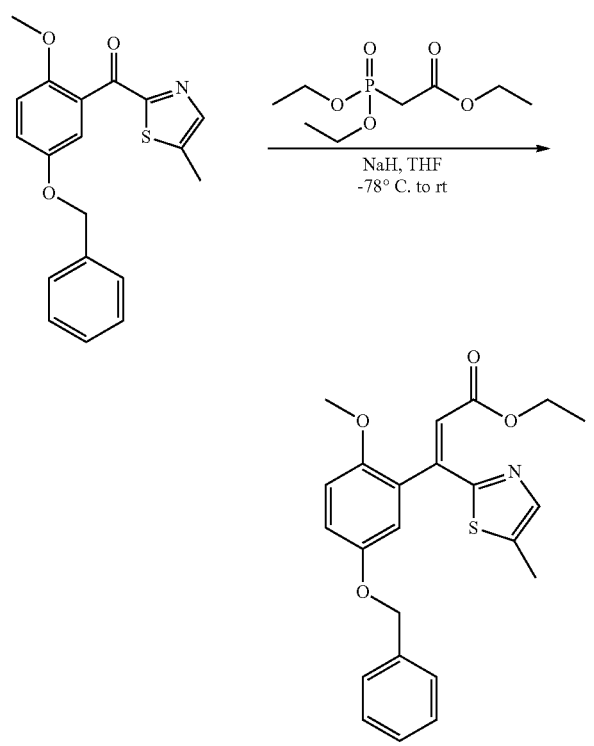

To a suspension of NaH (60%, 884 mg, 22.1 mmol) in dry THF (120 mL) was added ethyl 2-(diethoxyphosphoryl)acetate (4.96 g, 22.1 mmol) at −78° C. After being stirred at −78° C. for 1 hour, a solution of (5-(benzyloxy)-2-methoxyphenyl)(5-methylthiazol-2-yl)methanone (2.50 g, 7.37 mmol) in THF (30 mL) was added drop wise over 30 min. The mixture was stirred at −78° C. for 30 min and then warmed to room temperature with stirring overnight. The mixture was cooled to 0° C. and treated with water (50 mL), pH value was adjusted to 6 with HCl (0.5N). The organic layer was dried over Na₂SO₄, filtered, and concentrated under reduced pressure. The residue was purified by silica gel chromatography eluting with petroleum ether/EtOAc (3:1) to afford (Z)-ethyl 3-(5-(benzyloxy)-2-methoxyphenyl)-3-(5-methylthiazol-2-yl)acrylate (1.75 g, 58.0%) as yellow gel.

Synthesis of ethyl 3-(5-hydroxy-2-methoxyphenyl)-3-(5-methylthiazol-2-yl)-propanoate

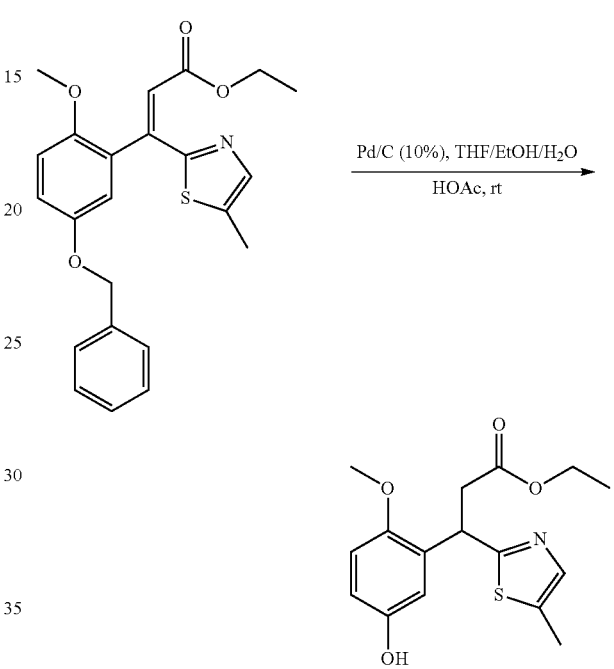

To a mixture of (Z)-ethyl 3-(5-(benzyloxy)-2-methoxyphenyl)-3-(5-methylthiazol-2-yl)acrylate (4.0 g, 9.8 mmol), HOAc (2.0 mL), and H₂O (5.0 mL) in EtOH (100 mL) and THF (60 mL) was added Pd/C (10%, dry, 5.0 g) under nitrogen atmosphere. The mixture was stirred at room temperature under H₂ atmosphere for 48 hrs. After filtration through a pad of Celite and evaporation of the solvent, the residue was purified by silica gel chromatography eluting with petroleum ether/EtOAc (3:1) to afford ethyl 3-(5-hydroxy-2-methoxyphenyl)-3-(5-methylthiazol-2-yl)propanoate (1.9 g, 60%) as a yellow-green gel.

Ethyl-3-(2-methoxy-5-(trifluoromethylsulfonyloxy) phenyl)-3-(5-methylthiazol-2-yl)propanoate

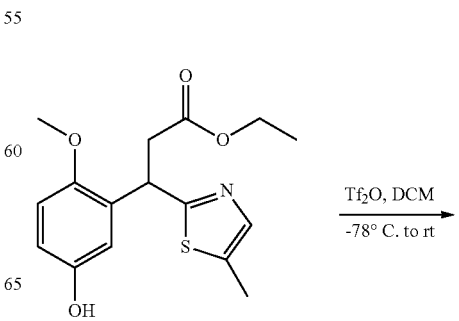

41
-continued

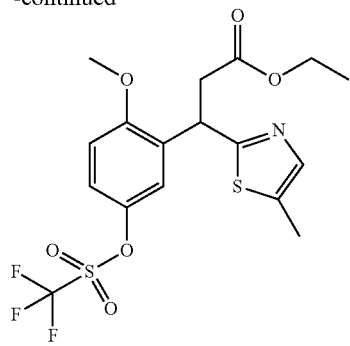

To a stirred solution of ethyl 3-(5-hydroxy-2-methoxyphenyl)-3-(5-methylthiazol-2-yl)propanoate (4.50 g, 14.0 mmol) and DIPEA (4.8 mL, 28 mmol) in DCM (150 mL) at −78° C. was added trifluoromethanesulfonic anhydride (4.74 g, 16.8 mmol) drop wise over 30 min. The resulting mixture was stirred at −78° C. for 30 minutes and warmed to room temperature with stirring overnight. The mixture was cooled to 0° C. and treated with water (50 mL). The organic layer was washed with brine (50 mL), dried over $Na_2SO_4$, and concentrated. The residue was purified by silica gel column chromatography eluting with petroleum ether/ethyl acetate (4:1) to give ethyl 3-(2-methoxy-5-(trifluoromethylsulfonyloxy)phenyl)-3-(5-methylthiazol-2-yl)propanoate (4.63 g, 73.0%) as yellow oil.

$^1$H NMR (400 MHz, DMSO-$d_6$) δ 7.41 (dd, J=9.1, 3.1 Hz, 1H), 7.37 (d, J=1.2 Hz, 1H), 7.35 (d, J=3.1 Hz, 1H), 7.18 (d, J=9.2 Hz, 1H), 5.07 (dd, J=8.3, 7.1 Hz, 1H), 3.99 (q, J=7.1 Hz, 2H), 3.86 (s, 3H), 3.32 (dd, J=16.3, 6.9 Hz, 1H), 3.02 (dd, J=16.3, 6.9 Hz, 1H), 2.35 (d, J=1.0 Hz, 3H), 1.08 (dd, J=9.2, 5.1 Hz, 3H).

Synthesis of Intermediate P4

3-(2-Methoxy-5-trifluoromethanesulfonyloxy-phenyl)-3-thiazol-2-yl-propionic acid ethyl ester The synthesis is carried out as described for the synthesis of intermediate P3 using 1,3-thiazole instead of 5-methyl-1,3-thiazole as starting material.

Synthesis of Intermediate A1

3-(3-Bromo-5-chloro-phenyl)-3-(5-methyl-thiazol-2-yl)-propionic acid

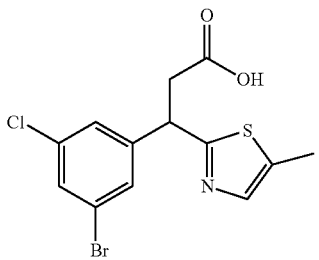 [SMILES: Cc1cnc(C(CC(=O)O)c2cc(Cl)cc(Br)c2)s1]

42
(3-Bromo-5-chloro-phenyl)-(5-methyl-thiazol-2-yl)-methanone

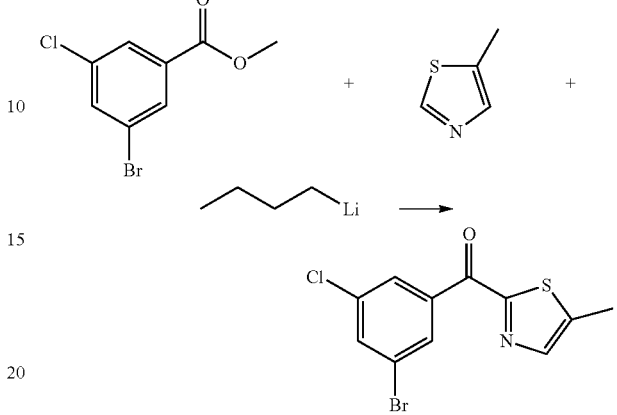

To a stirring mixture of 5-methylthiazole (4.37 g, 44.1 mmol) in dry THF (30 L) under was added n-BuLi (44.1 mmol, 17.64 ml solution in hexanes) drop wise over 10 minutes at −78° C. under nitrogen atmosphere. The mixture was stirred between −78° C. and −60° C. for 30 minutes and then cooled to −78° C. A solution of 3-Bromo-5-chloro-benzoic acid methyl ester (11.0 g, 44.1 mmol) in THF (20 mL) was added drop wise over 10 minutes. The resulting mixture was stirred at −78° C. for 30 minutes and warmed to room temperature with stirring overnight. The mixture was cooled to 0° C. and treated with water (50 mL). The resulting mixture was adjusted to pH around 6 with HCl (1N) and extracted with EtOAc (100 mL×3). The combined organic layers were dried over $Na_2SO_4$, filtered, and concentrated under reduced pressure. The residue was purified by silica gel column chromatography eluting with petroleum ether/EtOAc mixtures to afford (3-Bromo-5-chloro-phenyl)-(5-methyl-thiazol-2-yl)-methanone (14 g, yield=100%) as a solid.

(Z)-3-(3-Bromo-5-chloro-phenyl)-3-(5-methyl-thiazol-2-yl)-acrylic acid ethyl ester

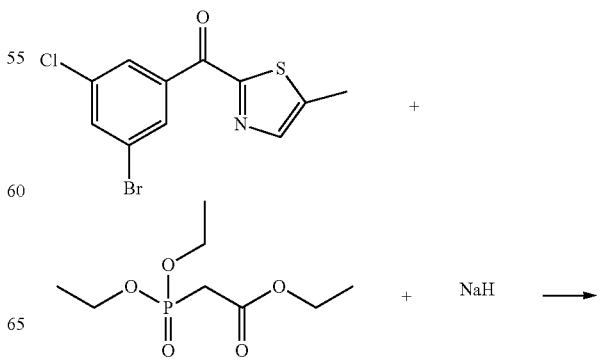

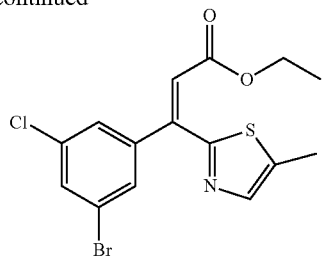

To a suspension of NaH (60%, 1.77 g, 44.2 mmol) in dry THF (30 mL) was added ethyl 2-(diethoxyphosphoryl)acetate (10.12 g, 44.2 mmol) at −78° C. After being stirred at −78° C. for 1 hour, a solution of 14 g (44.2 mmol) (3-Bromo-5-chloro-phenyl)-(5-methyl-thiazol-2-yl)-methanone in THF (10 mL) was added drop wise over 30 min. The mixture was stirred at −78° C. for 30 min and then warmed to room temperature with stirring overnight. The mixture was cooled to 0° C. and treated with water (50 mL), pH value was adjusted to 6 with HCl (0.5N) and extracted with EA (50 mL×3). The combined organic layers were dried over Na₂SO₄, filtered, and concentrated under reduced pressure. The residue was purified by silica gel chromatography eluting with petroleum ether/EtOAc mixtures to afford (Z)-3-(3-Bromo-5-chloro-phenyl)-3-(5-methyl-thiazol-2-yl)-acrylic acid ethyl ester as an gel (18 g, yield=106%) The material is used without further purification in the next step.

3-(3-Bromo-5-chloro-phenyl)-3-(5-methyl-thiazol-2-yl)-propionic acid ethyl ester

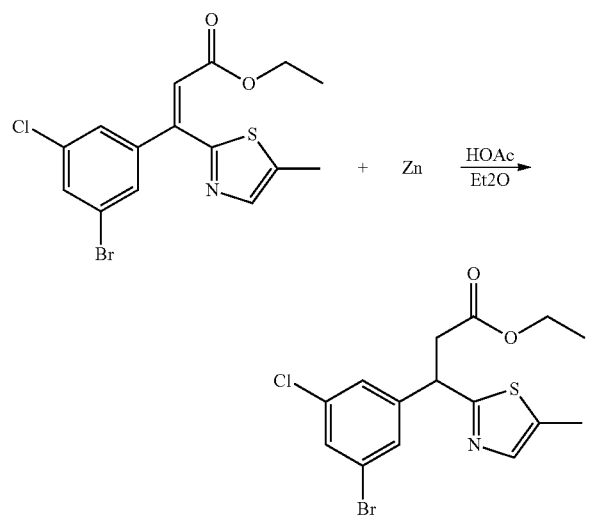

18 g (46.55 mmol) of (Z)-3-(3-Bromo-5-chloro-phenyl)-3-(5-methyl-thiazol-2-yl)-acrylic acid ethyl ester are dissolved in 250 ml Diethylether and 80 ml AcOH. 3 Eq (140 mmol) of zinc dust are added over a period of 60 minutes. The resulting mixture is allowed to stir overnight, diluted with 100 ml EtOAc and filtrated over a pad of Celite. The solvent is removed in vacuo, the residue taken up in EtOAc, washed with brine and dried over MgSO4. After evaporation of the solvent 17 g (Yield=99%) of crude product are obtained, which are used in the last step.

3-(3-Bromo-5-chloro-phenyl)-3-(5-methyl-thiazol-2-yl)-propionic acid

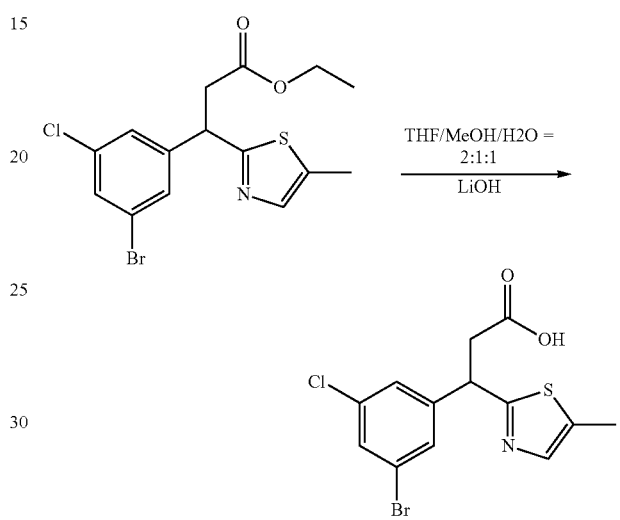

17 g (43.73 mmol) of 3-(3-Bromo-5-chloro-phenyl)-3-(5-methyl-thiazol-2-yl)-propionic acid ethyl ester are dissolved in 30 ml of a THF/MeOH/H2O=2:1:1 mixture and LiOH (2Eq) is added. After stirring overnight at RT, the solvent is removed in vacuo and the crude material is treated with 30 ml of EtOAc and 30 ml of water with pH=4. The organic phase is separated, dried over Na2SO4 and the solvent removed in vacuo. The crude material is recrystallized from heptane/EtOAc mixtures delivering 9.2 g (Yield=58%) of 3-(3-Bromo-5-chloro-phenyl)-3-(5-methyl-thiazol-2-yl)-propionic acid.

According to the procedures described above the following additional intermediates can be prepared:

A4: 3-(3-Bromo-5-fluoro-phenyl)-3-(5-methyl-thiazol-2-yl)-propionic acid

Using methyl-3-bromo-5-fluoro-benzoate as starting material.

A6: 3-(3-Bromo-phenyl)-3-(5-methyl-thiazol-2-yl)-propionic acid

Using methyl-benzoate as starting material

A7: 3-(3-Bromo-phenyl)-3-(4,5-dimethyl-thiazol-2-yl)-propionic acid

Using methyl-benzoate and 4,5-dimethyl-1,3-thiazole as starting materials

C2: 3-(3-Bromo-phenyl)-3-thiazol-2-yl-propionic acid

This material is commercially available from ZereneX (CAS-Number: 1082829-38-6), but can be prepared accordingly starting from methyl-benzoate and 1,3-thaizole as starting materials.

Synthesis of Intermediate A2

3-(3-Bromo-5-trifluoromethyl-phenyl)-3-(5-methyl-[1,3,4]oxadiazol-2-yl)-propionic acid

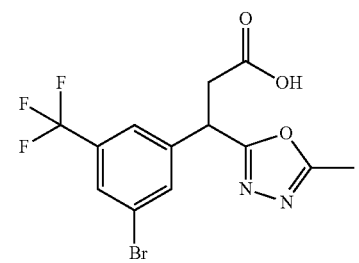 [SMILES: Cc1nnc(C(CC(=O)O)c2cc(Br)cc(C(F)(F)F)c2)o1]

(3-Bromo-5-trifluoromethyl-phenyl)-(5-methyl-[1,3,4]oxadiazol-2-yl)-methanol

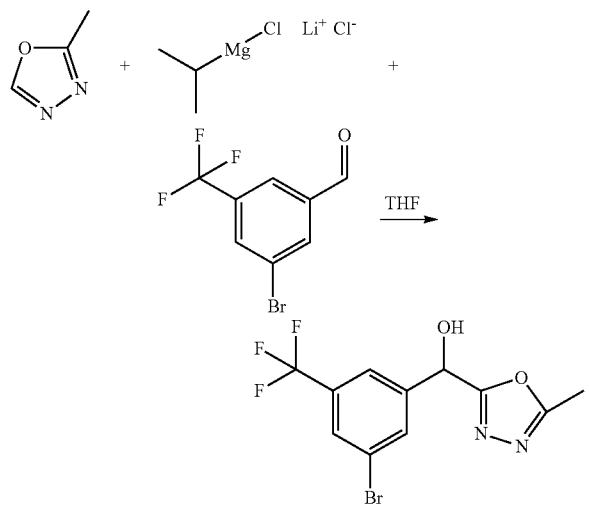

2.79 g (33.2 mmol) of 2-methyl-1,3,4-oxadiazole are dissolved in 45 ml THF at −5° C., 33.2 mmol (25.54 ml) of isopropyl magnesium chloride-lithium chloride complex are added during 20 minutes while the temperature is kept <0° C. The mixture is kept at 0° C. for 30 minutes, then 0.8 Eq (6.7 g) of 3-Bromo-5-trifluoromethyl-benzaldehyde are added and the resulting mixture is allowed to reach RT and stirred for additional 60 minutes. The reaction is then stopped by the addition of 10 ml saturated NH4Cl solution. 50 ml MTBE are added, the organic phase is separated, washed with brine and dried over MgSO4. The solvent is removed in vacuo and the crude material (9 g) is used without further purification in the next step:

(3-Bromo-5-trifluoromethyl-phenyl)-(5-methyl-[1,3,4]oxadiazol-2-yl)-methanone

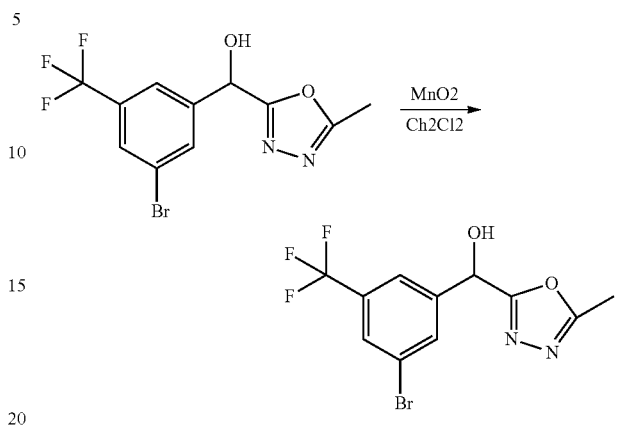

The crude material from the first step is dissolved in 100 ml CH2Cl2 and 20 g MnO2 are added. The resulting mixture is stirred for 60 minutes at RT and filtrated. After evaporation of the solvent 9.06 g (98%) of crude material is obtained, which is used without further purification in the next step.

(Z)-3-(3-Bromo-5-trifluoromethyl-phenyl)-3-(5-methyl-[1,3,4]oxadiazol-2-yl)-acrylic acid ethyl ester

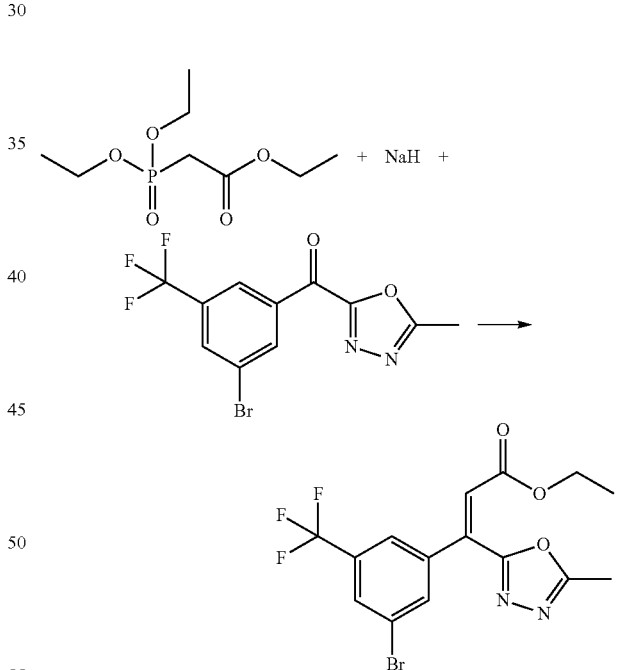

To a suspension of NaH (60%, 1.13 g, 28.35 mmol) in dry THF (20 mL) was added ethyl 2-(diethoxyphosphoryl)acetate (6.49 g, 28.35 mmol) at −78° C. After being stirred at −78° C. for 1 hour, a solution of (3-Bromo-5-trifluoromethyl-phenyl)-(5-methyl-[1,3,4]oxadiazol-2-yl)-methanone (9.047 g, 27 mmol) in 20 ml THF was added drop wise over 30 min. The mixture was stirred at −78° C. for 30 min and then warmed to room temperature followed by stirring overnight. The mixture was cooled to 0° C. and treated with water (50 mL), pH value was adjusted to 6 with HCl (0.5N) and extracted with EtOAc (50 mL×3). The combined organic layers were dried over Na$_2$SO$_4$, filtered, and concentrated under reduced pressure. The residue was purified by silica gel chromatography eluting with a petroleum ether/EtOAc mixture to afford 9 g of the desired product (Yield: 90%).

Synthesis of 3-(3-Bromo-5-trifluoromethyl-phenyl)-3-(5-methyl-[1,3,4]oxadiazol-2-yl)-propionic acid ethyl ester

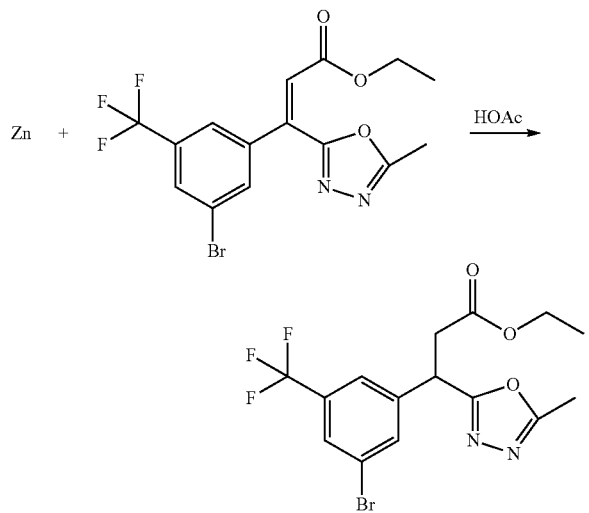

11.2 g (27.64 mmol) (Z)-3-(3-Bromo-5-trifluoromethyl-phenyl)-3-(5-methyl-[1,3,4]oxadiazol-2-yl)-acrylic acid ethyl ester is dissolved in 200 ml acetic acid and 14.1 g Zinc dust (215.6 mmol, 7.8 mmol) is added slowly over a period of 30 minutes. The temperature of the reaction mixture is not allowed to reach >30° C. during the addition of the zinc dust. The resulting mixture is allowed to stir overnight. After filtration 200 ml EtOAc and 200 ml water are added and the organic phase is separated and washed with brine. After removal of the solvent the crude material is purified by column chromatography on silica gel using heptane/EtOAc=3:1 as eluent. 3.97 g of 3-(3-Bromo-5-trifluoromethyl-phenyl)-3-(5-methyl-[1,3,4]oxadiazol-2-yl)-propionic acid ethyl ester (yield=35%) are isolated.

Synthesis of 3-(3-Bromo-5-trifluoromethyl-phenyl)-3-(5-methyl-[1,3,4]oxadiazol-2-yl)-propionic acid

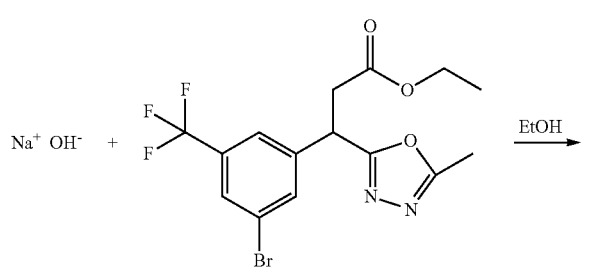

-continued

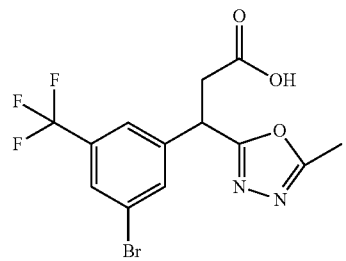

3.97 g (9.75 mmol) of 3-(3-Bromo-5-trifluoromethyl-phenyl)-3-(5-methyl-[1,3,4]oxadiazol-2-yl)-propionic acid ethyl ester are dissolved in 10 ml ethanol and 6.34 ml of a 2N NaOH solution are added. The mixture is allowed to stir for 4 hours at RT, the ethanol is removed and the residue taken up in 30 ml EtOAc and 20 ml water.

After phase separation the organic phase is dried over Mg2SO4 and the solvent removed in vacuo to deliver 3.3 g (Yield=89%) of the desired product 3-(3-Bromo-5-trifluoromethyl-phenyl)-3-(5-methyl-[1,3,4]oxadiazol-2-yl)-propionic acid.

According to the procedure described above the following additional intermediates are prepared:

A8: 3-(3-Bromo-5-chloro-phenyl)-3-(5-methyl-[1,3,4]oxadiazol-2-yl)-propionic acid Using 3-bromo-5-chloro-benzaldehyde as starting material A9: 3-(3-Bromo-5-fluoro-phenyl)-3-(5-methyl-[1,3,4]oxadiazol-2-yl)-propionic acid Using 3-Bromo-5-fluoro-benzaldehyde as starting material A10: 3-(5-Bromo-pyridin-3-yl)-3-(5-methyl-[1,3,4]oxadiazol-2-yl)-propionic acid Using 5-bromo-nicotinaldehyde as starting material C1: 3-(3-Bromo-phenyl)-3-(5-methyl-[1,3,4]oxadiazol-2-yl)-propionic acid This intermediate is commercially available from Aurora Building Blocks (CAS-Number: 1082916-80-0), but can be obtained using 3-bromo-benzaldehyde Synthesis of Intermediate A3

3-(3-Bromo-5-fluoro-phenyl)-3-oxazol-2-yl-propionic acid

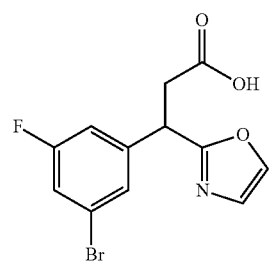 [SMILES: O=C(O)CC(c1cc(F)cc(Br)c1)c1ncco1]

Synthesis of 3-Bromo-5-fluoro-benzoyl chloride

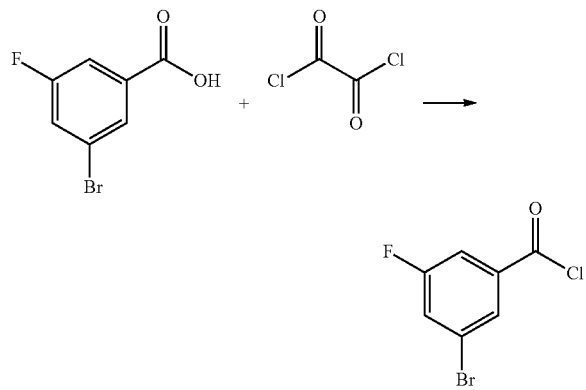

10 g of 3-bromo-5-fluoro-benzoic acid are suspended in 100 ml of DCM, 0.5 ml DMF and 4.5 ml oxalyl chloride (1.15 Eq) are added and the resulting mixture is stirred for 100 minutes at RT. The solvent is removed by vacuo and the benzoic acid chloride is isolated by distillation.

Synthesis of (3-Bromo-5-fluoro-phenyl)-oxazol-2-yl-methanone

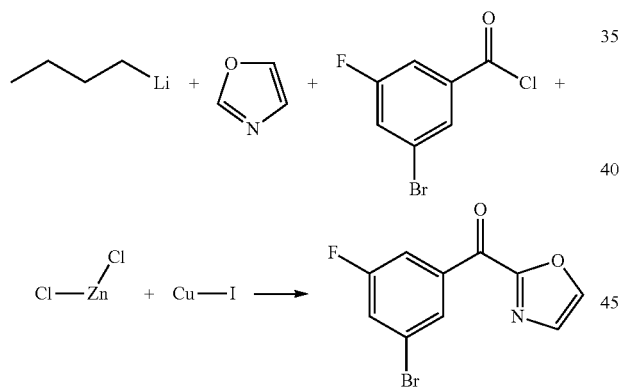

To a stirring mixture of 1,3-oxazole (3.46 g, 50 mmol) in dry THF (50 mL) was added n-BuLi (1.1 Eq, 20.01 ml solution in hexanes) drop wise over 10 minutes at −78° C. under nitrogen atmosphere. After stirring for 30 minutes at −78° C. zinc chloride (0.1 mmol, 2.2 Eq) as a 2M solution in 5-methyl-tetrahydrofurane was added within 30 minutes and the mixture was allowed to reach −20° C. during the addition. Then the mixture was stirred at 0° C. for 40 minutes, CuI (8.66 g, 45.5 mmol) was added and stirring continued for additional 10 minutes. 3-Bromo-5-fluoro-benzoyl chloride (45.5 mmol, 8.66 g) was dissolved in 50 ml of THF and added to the metallated 1,3-oxazole. Stirring was continued until complete conversion was observed by LCMS and 50 ml water and 50 ml of a 0.5 M citric acid solution were added. The solid material from the reaction mixture was filtered off and washed with 5-methyl-thf. The organic phase was separated, washed with brine and dried over MgSO4. 10.8 g of crude material (yield=88%) were obtained and used directly in the next step.

The mixture was stirred between −78° C. and −60° C. for 30 minutes and then cooled to −78° C. A solution of 3-Bromo-5-chloro-benzoic acid methyl ester (11.0 g, 44.1 mmol) in THF (20 mL) was added drop wise over 10 minutes. The resulting mixture was stirred at −78° C. for 30 minutes and warmed to room temperature with stirring overnight. The mixture was cooled to 0° C. and treated with water (50 mL). The resulting mixture was adjusted to pH around 6 with HCl (1N) and extracted with EtOAc (100 mL×3). The combined organic layers were dried over $Na_2SO_4$, filtered, and concentrated under reduced pressure. The residue was purified by silica gel column chromatography eluting with petroleum ether/EtOAc mixtures to afford (3-Bromo-5-chloro-phenyl)-(5-methyl-thiazol-2-yl)-methanone (14 g, yield=100%) as a solid.

Synthesis of (Z)-3-(3-Bromo-5-fluoro-phenyl)-3-oxazol-2-yl-acrylic acid ethyl ester

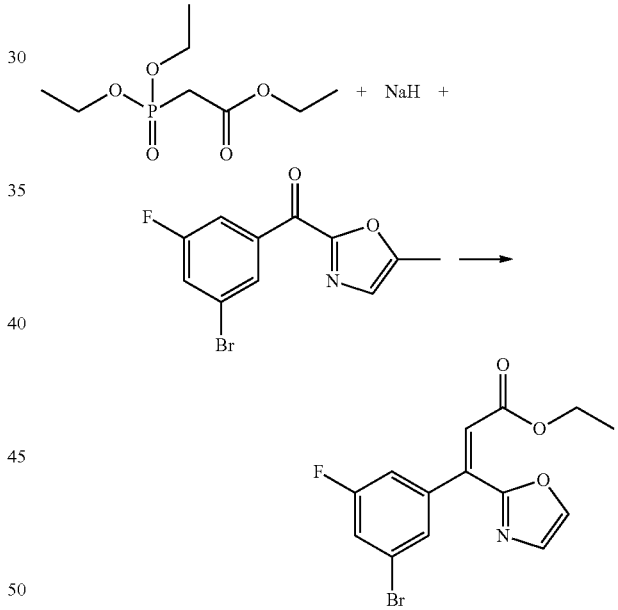

To a suspension of NaH (60%, 1.6 g, 40 mmol) in dry THF (30 mL) was added ethyl 2-(diethoxyphosphoryl)acetate (9.15 g, 40 mmol) at −78° C. After being stirred at −78° C. for 1 hour, a solution of (3-Bromo-5-fluoro-phenyl)-oxazol-2-yl-methanone (10.8 g, 40 mmol) in 20 ml THF was added drop wise over 30 min. The mixture was stirred at −78° C. for 30 min and then warmed to room temperature followed by stirring overnight. The mixture was cooled to 0° C. and treated with water (50 mL), pH value was adjusted to 6 with HCl (0.5N) and extracted with EtOAc (50 mL×3). The combined organic layers were dried over $Na_2SO_4$, filtered, and concentrated under reduced pressure. The residue was purified by silica gel chromatography eluting with a petroleum ether/EtOAc mixture to afford 9.5 g of the desired product (Yield: 61%)

Synthesis of 3-(3-Bromo-5-fluoro-phenyl)-3-oxazol-2-yl-propionic acid ethyl ester

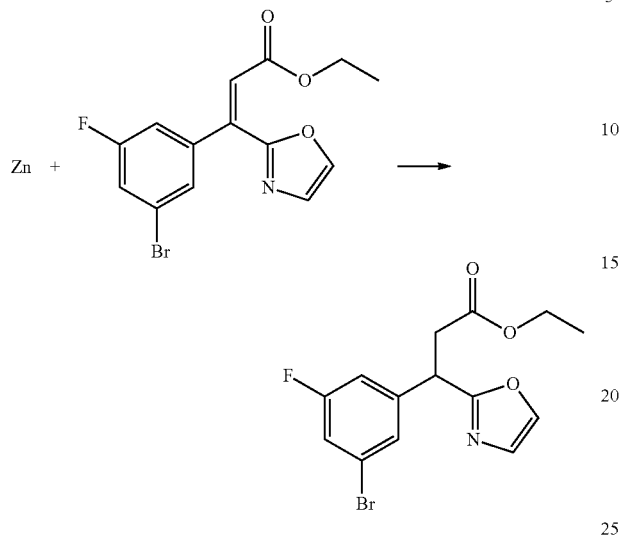

9.5 g (27.93 mmol) (Z)-3-(3-Bromo-5-fluoro-phenyl)-3-oxazol-2-yl-acrylic acid ethyl ester is dissolved in 200 ml acetic acid and 9.5 g Zinc dust (11 Ea)) is added slowly over a period of 30 minutes. The temperature of the reaction mixture is not allowed to reach >30° C. during the addition of the zinc dust. The resulting mixture is allowed to stir overnight. After filtration 200 ml EtOAc and 200 ml water are added and the organic phase is separated and washed with brine. After removal of the solvent the crude material is purified by column chromatography on silica gel using heptane/EtOAc=3:1 as eluent. 9.50 g of 3-(3-Bromo-5-fluoro-phenyl)-3-oxazol-2-yl-propionic acid ethyl ester are isolated (yield=615)

Synthesis of 3-(3-Bromo-5-fluoro-phenyl)-3-oxazol-2-yl-propionic acid

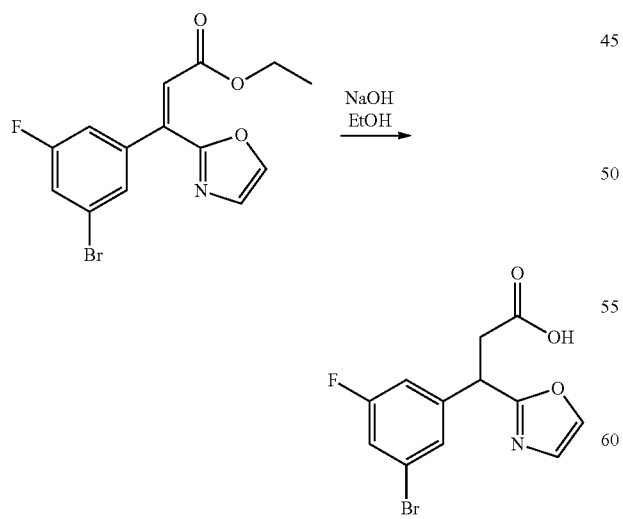

9.50 g (27.76 mmol) of 3-(3-Bromo-5-fluoro-phenyl)-3-oxazol-2-yl-propionic acid ethyl ester are dissolved in 30 ml ethanol and 20.82 ml of a 2N NaOH solution are added. The mixture is allowed to stir for 4 hours at RT, the ethanol is removed and the residue taken up in 30 ml EtOAc and 20 ml water. After phase separation the organic phase is dried over Mg2SO4 and the solvent removed in vacuo to deliver 8.35 g (Yield=58%) of the desired product 3-(3-Bromo-5-fluoro-phenyl)-3-oxazol-2-yl-propionic acid.

According to this procedure the following additional intermediates are prepared:

A5: 3-(3-Bromo-5-fluoro-phenyl)-3-oxazol-2-yl-propionic acid

Using 3-bromo benzoyl-chloride as starting material

Synthesis of Novel Boronic Acids 6-methoxy-2,2-dimethyl-2,3-dihydrobenzofuran-7-ylboronic acid

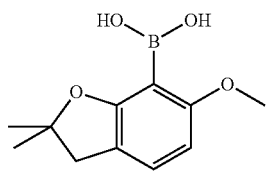

Methyl 2-(3-methoxyphenoxy)acetate

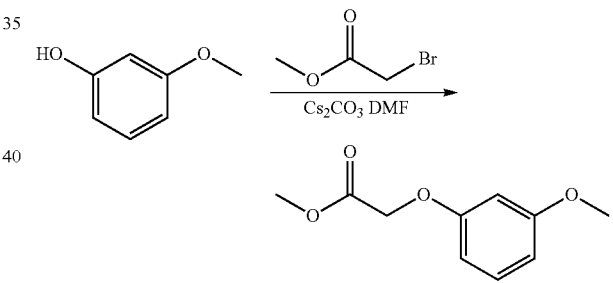

To a mixture of 3-methoxyphenol (20 g, 161.3 mmol) and Cs$_2$CO$_3$ (52.4 g, 161.3 mmol) in DMF (200 mL), methyl bromoacetate (24.5 g, 161.3 mmol) was added. The reaction mixture was stirred at room temperature under argon overnight. The inorganic precipitate was filtered off, and the filtrate was concentrated under reduced pressure. The residue was partitioned between water (200 mL) and CH$_2$Cl$_2$ (200 mL×3). The combined organic solution was dried over Na$_2$SO$_4$ and evaporated to give (28 g, 90%) product.

1-(3-methoxyphenoxy)-2-methylpropan-2-ol

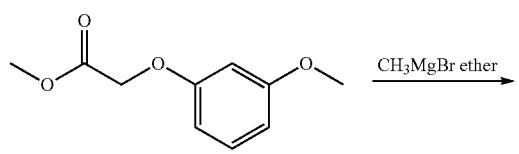

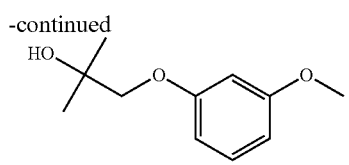

To a solution of methyl 2-(3-methoxyphenoxy)acetate (28 g, 143 mmol) in ether (200 mL) cooled in an ice water bath was added drop wise a solution of methyl magnesium bromide (143 mmol, 3M in ether) in ether. After 1 h the reaction mixture was poured into 500 mL of 2N HCl. The mixture was extracted with EA (200 mL×3). The combined organic layers were dried over Na$_2$SO$_4$. After filtration and evaporation of the solvent, the intermediate (25 g 90%) was obtained.

6-methoxy-2,2-dimethyl-2,3-dihydrobenzofuran

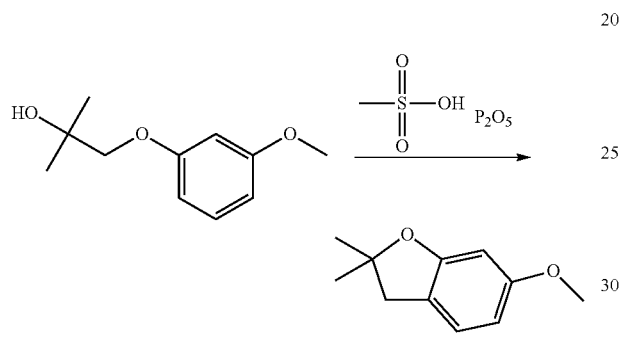

To a solution of phosphorous pentoxide (55.1 g, 383 mmol) in methanesulfonic acid (100 mL) was added drop wise 1-(3-methoxyphenoxy)-2-methylpropan-2-ol (25 g, 127.6 mmol) over a 30 min period. The reaction mixture was stirred for 3 h at r.t. The reaction mixture was poured into 500 mL of ice water and extracted with ether (200 mL×3). The combined extracts were dried and evaporated. The residue was purified by silica gel column chromatography eluting with petroleum ether/ether (9:1) to afford 6-methoxy-2,2-dimethyl-2,3-dihydrobenzofuran (5.5 g, 25%) as a yellow oil.

6-methoxy-2,2-dimethyl-2,3-dihydrobenzofuran-7-ylboronic acid

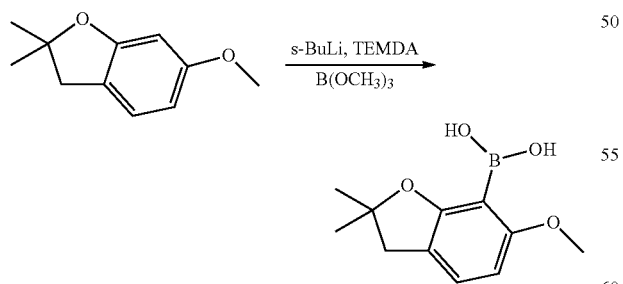

s-BuLi (35 mL, 1.3M in cyclohexane) was added to TMEDA (6.6 mL) at −78° C. drop wise within 30 min, 20 mL of THF was added to keep stirring. After 20 min, 6-methoxy-2,2-dimethyl-2,3-dihydrobenzofuran (5.4 g, 30.3 mmol) in THF (30 mL) was added into the lithium solution slowly. The solution was stirred at −78° C. for 1.5 h and trimethyl borate (18 mL) was added. The mixture was warmed to room temperature and stirred at room temperature overnight. The solution was acidified to pH=5-6 and extracted with ethyl acetate. The organic layer was concentrated and the resulted residue was purified on column chromatography (silica gel, dichloromethane/petroleum ether=3/1) to give the crude product, which was sonicated with petroleum ether. The white precipitate was filtered and dried to give 6-methoxy-2,2-dimethyl-2,3-dihydrobenzofuran-7-ylboronic acid (3.55 g, 53%) as a white solid.

$^1$H NMR (400 MHz, DMSO-d$_6$) δ 7.58 (brs, 2H), 7.07 (d, J=8.0 Hz, 1H), 6.36 (d, J=8.4 Hz, 1H), 3.68 (s, 3H), 2.87 (s, 2H), 1.38 (s, 6H).

2-(2-methoxy-5-(methylsulfonyl)phenyl)-4,4,5,5-tetramethyl-1,3,2-dioxaborolane

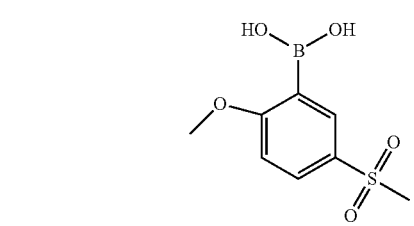

2-bromo-4-(methylsulfonyl)phenol

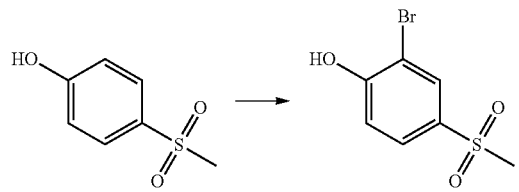

To a solution of 4-(methylsulfonyl)phenol (5 g, 29.1 mmol) in ether (100 mL) at −15° C. was slowly added acetic acid (5 mL). To this cold solution was slowly added Br$_2$ (5.1 g, 32.0 mmol) and the reaction was stirred at −10° C. for 1 h and then warmed to r.t. and stirred for further 10 h. After the reaction was completed, 100 mL of sat. NaHCO$_3$ aq. was added and the mixture was extracted with EA (50 mL×3). The combined organic layers were washed with brine and dried over Na$_2$SO$_4$. After filtration and evaporation of the solvent, 2-bromo-4-(methylsulfonyl)phenol (3.2 g, 43.6%) was obtained as a white solid.

2-bromo-1-methoxy-4-(methylsulfonyl)benzene

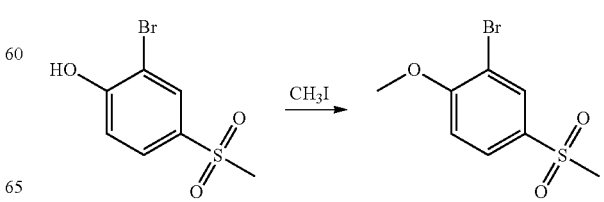

To a solution of 2-bromo-4-(methylsulfonyl)phenol (3.2 g, 12.7 mmol) in DMF (35 mL) at 0° C. was added K₂CO₃ (5.3 g, 38.1 mmol). The reaction was stirred at 0° C. for 0.5 h and to this cold solution was slowly added CH₃I (2.7 g, 19.1 mmol) drop wise. The reaction was stirred at r.t. overnight. After the reaction was completed, 80 mL of ice-water was added. The mixture was extracted with EA (60 mL×3). The combined organic layers were washed with brine and dried over Na₂SO₄. After filtration and evaporation of the solvent, the obtained residue was purified on column chromatography (silica gel, ethyl acetate/petroleum ether=1:4) to give 2-bromo-1-methoxy-4-(methylsulfonyl)benzene (2.12 g, 63.0%) as yellow solid.

2-(2-methoxy-5-(methylsulfonyl)phenyl)-4,4,5,5-tetramethyl-1,3,2-dioxaborolane

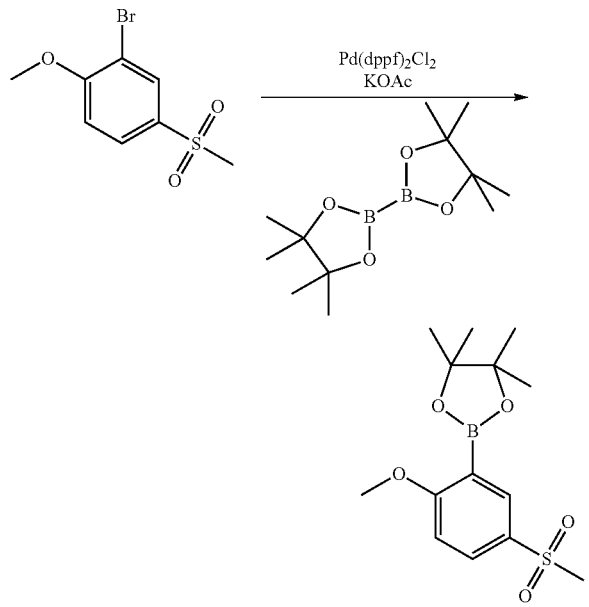

A mixture of 2-bromo-1-methoxy-4-(methylsulfonyl)benzene (2.12 g, 8 mmol), 4,4,4',4',5,5,5',5'-octamethyl-2,2'-bi(1,3,2-dioxaborolane) (2.65 g, 10.4 mmol), potassium acetate (2.4 g, 24 mmol) and [1,1'-Bis(diphenylphosphino)ferrocene]dichloropalladium(II) (600 mg) in 1,4-dioxane (50 mL) were heated to 80° C. overnight. After cooling, the mixture was filtered. The filtrate was concentrated and the resulted residue was purified on column chromatography (silica gel, dichloromethane/petroleum ether=3/1) to give 2-(2-methoxy-5-(methylsulfonyl)phenyl)-4,4,5,5-tetramethyl-1,3,2-dioxaborolane (200 mg, 8%) as a white solid.

¹H NMR (400 MHz, DMSO-d₆) δ 8.01-7.98 (m, 2H), 7.21 (d, J=8.8 Hz, 1H), 3.85 (s, 3H), 3.15 (s, 3H), 1.32 (s, 12H).

2-methoxy-6-(pyrrolidine-1-carbonyl)phenylboronic acid

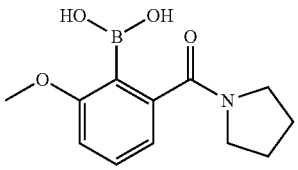 [SMILES: COc1cccc(C(=O)N2CCCC2)c1B(O)O]

(3-methoxyphenyl)(pyrrolidin-1-yl)methanone

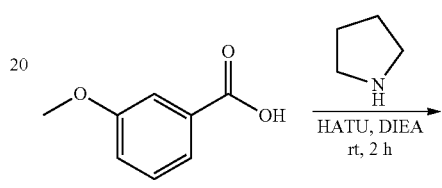

A solution of 3-methoxybenzoic acid (13.5 g, 88.8 mmol), pyrrolidine (9 mL, 133 mmol), HATU (33 g, 88.8 mmol) and DIEA (30 mL, 172 mmol) in DMF (100 mL) was stirred at room temperature for 2 h. The solution was added water and extracted with ethyl acetate (200 mL×3). The organic layer was dried and concentrated. The residue was purified by silica gel chromatography (eluted with petroleum ether:ethyl acetate=2:1 to 1:1) to give (3-methoxyphenyl)(pyrrolidin-1-yl)methanone (23 g, 100%) as a yellow oil.

1H NMR (400 MHz, CDCl3) δ 7.30-7.26 (m, 1H), 7.05 (m, 2H), 6.94-6.92 (m, 1H), 3.80 (s, 3H), 3.59 (t, J=6.8 Hz, 2H), 3.40 (t, J=6.8 Hz, 2H), 1.94-1.83 (m, 4H).

2-methoxy-6-(pyrrolidine-1-carbonyl)phenylboronic acid

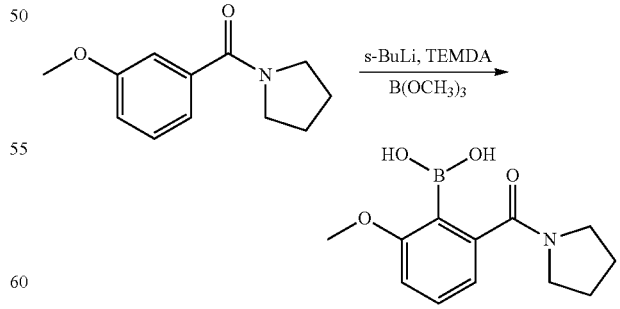

s-BuLi (70 mL, 1.3M in cyclohexane) was added to TMEDA (15.3 g, 131.9 mmol) at −78° C. dropwise within 30 min. After stirring for 20 min, (3-methoxyphenyl)(pyrrolidin-1-yl)methanone (16 g, 78 mmol) in THF (40 mL) was added into the lithium solution slowly. The solution was stirred at −78° C. for 1.5 h and trimethyl borate (36 mL, 322.6 mmol) was added. The mixture was warmed to room temperature and stirred at rt overnight. The solution was acidified to pH=5-6 and the precipitate were filtered. The filter cake was washed with water and ethyl acetate to give 2-methoxy-6-(pyrrolidine-1-carbonyl)phenylboronic acid (5.5 g, 28%) as a white solid.

1H NMR (400 MHz, DMSO-d6) δ 7.49 (d, J=8.0 Hz, 1H), 7.38 (t, J=8.0 Hz, 1H), 7.12 (d, J=8.0 Hz, 1H0, 7.01 (brs, 2H), 4.08 (t, J=6.0 Hz, 2H), 3.84-3.74 (m, 5H), 2.11-2.07 (m, 2H), 1.94-1.91 (m, 2H).

Synthesis of 2-[4-Methoxy-3-(4,4,5,5-tetramethyl-[1,3,2]dioxaborolan-2-yl)-phenyl]-2-methyl-propionitrile

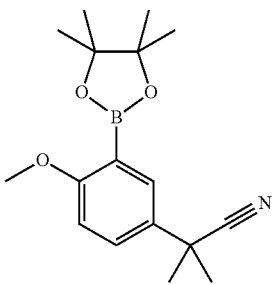 [SMILES: COc1ccc(C(C)(C)C#N)cc1B1OC(C)(C)C(C)(C)O1]

Synthesis of 2-(3-Bromo-4-methoxy-phenyl)-2-methyl-propionitrile

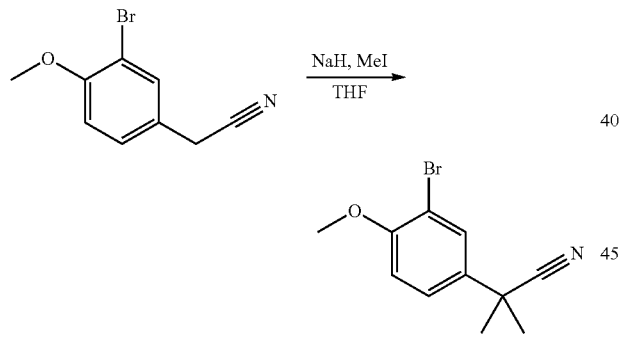

NaH (3.7 g, 93 mmol) was added into THF (100 mL) slowly at 0° C., followed by (3-Bromo-4-methoxy-phenyl)-acetonitrile (7 g, 31 mmol). The solution was stirred at 0° C. for 1 hour and then MeI (26.4 g, 186 mmol) was added. This reaction mixture was stirred at rt for overnight. Water (10 mL) was added and the mixture was extracted with EA. The organic layer was washed with brine, dried over EA and concentrated to give 2-(3-Bromo-4-methoxy-phenyl)-2-methyl-propionitrile as a colourless oil (9 g, 85%).

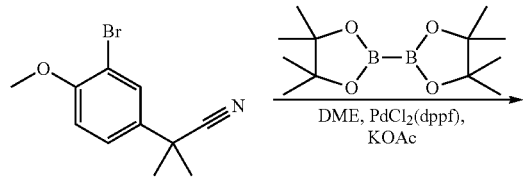

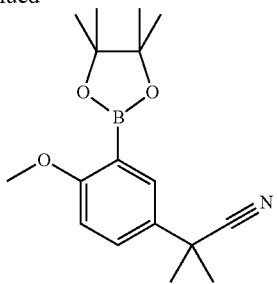

To a solution of 2-(3-Bromo-4-methoxy-phenyl)-2-methyl-propionitrile (7.8 g, 31 mmol) in DME (100 mL, degassed by sparing with N₂), 4,4,5,5,4',4',5',5'-Octamethyl-[2,2']bi[[1,3,2]dioxaborolanyl] (9.4 g, 37.2 mmol), KOAc (9.1 g, 93 mmol) and PdCl₂(dppf) (2.6 g, 3.1 mmol) was added. The mixture was stirred at 110° C. under N₂ atmosphere for 2 hours. The mixture was filtered, concentrated and purified by silica gel chromatography to afford 2-[4-Methoxy-3-(4,4,5,5-tetramethyl-1,3,2]dioxaborolan-2-yl)-phenyl]-2-methyl-propionitrile as a white solid (4.1 g, 44%).

Synthesis of (S)-3-(5'-Isopropyl-2'-methoxy-biphenyl-3-yl)-3-(5-methyl-[1,3,4]oxadiazol-2-yl)-propionic acid and (R)-3-(5'-Isopropyl-2'-methoxy-biphenyl-3-yl)-3-(5-methyl-[1,3,4]oxadiazol-2-yl)-propionic acid

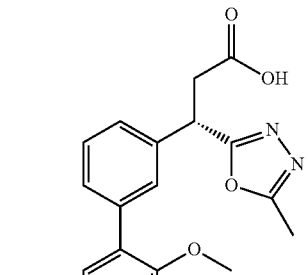

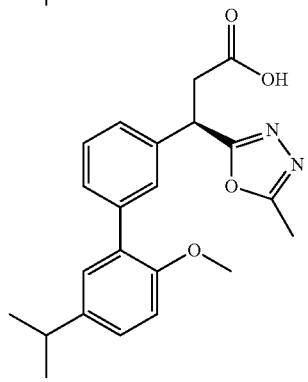

12.83 g (66.11 mmol) of 5-isopropyl-2-methoxybenzeneboronic acid, 48.97 g (150.3 mmol) and 18.7 g (60.1 mmol) of 3-(3-Bromo-phenyl)-3-(5-methyl-[1,3,4]oxadiazol-2-yl)-propionic acid are heated together with 3 mmol of bis(triphenylphosphine)palladium (II)dichloride in 200 ml of DMF and 30 ml of water for 10 hours at 100° C. The reaction mixture is diluted with conc. NH4Cl solution (200 ml) and extracted with methyl-tetrahydrofurane. The organic phase is filtrated over Celite and 100 g of SiO2 and the solvent is removed in vacuo. The obtained crude 3-(5'-Isopropyl-2'-methoxy-biphenyl-3-yl)-3-(5-methyl-[1,3,4]oxadiazol-2-yl)-propionic acid is used directly in the next step. (Yield=57%, 28 g)

The racemic 3-(5'-Isopropyl-2'-methoxy-biphenyl-3-yl)-3-(5-methyl-[1,3,4]oxadiazol-2-yl)-propionic acid is subjected to chromatography on a chiral column using a heptane-methanol gradient to isolate the pure enantiomers (S)-3-(5'-Isopropyl-2'-methoxy-biphenyl-3-yl)-3-(5-methyl-[1,3,4] oxadiazol-2-yl)-propionic acid and (R)-3-(5'-Isopropyl-2'-methoxy-biphenyl-3-yl)-3-(5-methyl-[1,3,4]oxadiazol-2-yl)-propionic acid. The configuration on the chiral carbon atom is arbitrarily assigned (S) to the enantiomer with the shortest retention time on the applied chiral column and (R) to the enantiomer with the longest retention time on the applied chiral column.

Analogously as described in the synthesis examples, the example compounds of the formula I listed in Table 1 were prepared.

TABLE 1

Example compounds of the formula I

| No | CHEMICAL_NAME | Starting material | Suzuki reaction | CATH A IC50 [µM] | Observed Mass | Retention Time [min] | LC-MS Method |
|---|---|---|---|---|---|---|---|
| 1 | 3-(5'-Chloro-2'-methoxy-biphenyl-3-yl)-3-thiazol-2-yl-propionic acid | C2 | A | 0.160 | 374.14 | 1.83 | LC1 |
| 2 | 3-(5'-Isopropyl-2'-methoxy-biphenyl-3-yl)-3-thiazol-2-yl-propionic acid | C2 | A | 0.132 | 382.25 | 1.93 | LC1 |
| 3 | 3-(5'-Fluoro-2'-methoxy-biphenyl-3-yl)-3-thiazol-2-yl-propionic acid | C2 | A | 0.160 | 358.16 | 1.75 | LC1 |
| 4 | 3-(5'-tert-Butyl-2'-methoxy-biphenyl-3-yl)-3-thiazol-2-yl-propionic acid | C2 | A | 0.119 | 394.25 | 1.96 | LC3 |
| 5 | (S)-3-(5'-tert-Butyl-2'-methoxy-biphenyl-3-yl)-3-thiazol-2-yl-propionic acid | C2 | A | 0.035 | 395.93 | 1.97 | LC1 |
| 6 | (R)-3-(5'-tert-Butyl-2'-methoxy-biphenyl-3-yl)-3-thiazol-2-yl-propionic acid | C2 | A | 3.383 | 396.27 | 4.86 | LC2 |
| 7 | 3-(5-Fluoro-2',6'-dimethoxy-biphenyl-3-yl)-3-(5-methyl-thiazol-2-yl)-propionic acid | A4 | A | 0.005 | 402.2 | 1.78 | LC1 |
| 8 | 3-(5,5'-Dichloro-2'-methoxy-biphenyl-3-yl)-3-(5-methyl-thiazol-2-yl)-propionic acid | A1 | A | 0.034 | 422.17 | 1.96 | LC1 |
| 9 | 3-(5'-tert-Butyl-2'-methoxy-biphenyl-3-yl)-3-(5-methyl-[1,3,4]oxadiazol-2-yl)-propionic acid | C1 | A | 0.061 | 395.29 | 1.88 | LC1 |
| 10 | 3-(5-Chloro-2',6'-dimethoxy-biphenyl-3-yl)-3-(5-methyl-thiazol-2-yl)-propionic acid | A1 | A | 0.007 | 418.13 | 1.84 | LC1 |
| 11 | (R)-3-(5'-tert-Butyl-2'-methoxy-biphenyl-3-yl)-3-oxazol-2-yl-propionic acid | A5 | A | 0.051 | 379.9 | 1.91 | LC1 |
| 12 | (S)-3-(5'-tert-Butyl-2'-methoxy-biphenyl-3-yl)-3-oxazol-2-yl-propionic acid | C3 | A | | 380.32 | 4.8 | LC2 |
| 13 | 3-(5'-tert-Butyl-2'-methoxy-biphenyl-3-yl)-3-oxazol-2-yl-propionic acid | A5 | A | 0.103 | 380.19 | 4.8 | LC2 |
| 14 | 3-(2',6'-Dimethoxy-4'-methyl-biphenyl-3-yl)-3-thiazol-2-yl-propionic acid | C2 | A | 0.066 | 384.2 | 1.77 | LC1 |
| 15 | 3-(2',6'-Dimethoxy-4'-methyl-biphenyl-3-yl)-3-(5-methyl-thiazol-2-yl)-propionic acid | A6 | A | 0.044 | 398.28 | 1.81 | LC1 |
| 16 | 3-(2',6'-Dimethoxy-4'-methyl-biphenyl-3-yl)-3-oxazol-2-yl-propionic acid | A5 | A | 0.049 | 368.33 | 1.71 | LC1 |
| 17 | 3-(2'-Methoxy-biphenyl-3-yl)-3-thiazol-2-yl-propionic acid | C2 | A | 0.154 | 340.15 | 1.86 | LC1 |
| 18 | 3-(5'-tert-Butyl-2'-methoxy-biphenyl-3-yl)-3-(4,5-dimethyl-thiazol-2-yl)-propionic acid | A7 | A | 0.530 | 424.25 | 2.16 | LC1 |
| 19 | 3-(5'-Chloro-2'-methoxy-biphenyl-3-yl)-3-(4,5-dimethyl-thiazol-2-yl)-propionic acid | A7 | A | 0.657 | 402.16 | 2.06 | LC1 |
| 20 | 3-(2',6'-Dimethoxy-biphenyl-3-yl)-3-thiazol-2-yl-propionic acid | C2 | A | 0.030 | 370.19 | 1.7 | LC1 |

TABLE 1-continued

Example compounds of the formula I

| No | CHEMICAL_NAME | Starting material | Suzuki reaction | CATH A IC50 [µM] | Observed Mass | Retention Time [min] | LC-MS Method |
|---|---|---|---|---|---|---|---|
| 21 | 3-(2',5'-Dimethoxy-biphenyl-3-yl)-3-thiazol-2-yl-propionic acid | C2 | A | 0.129 | 370.18 | 1.72 | LC1 |
| 22 | 3-(2'-Methoxy-5'-trifluoromethyl-biphenyl-3-yl)-3-thiazol-2-yl-propionic acid | C2 | A | 0.134 | 408.17 | 1.85 | LC1 |
| 23 | 3'-(2-Carboxy-1-thiazol-2-yl-ethyl)-6-methoxy-biphenyl-3-carboxylic acid methyl ester | C2 | A | 0.140 | 398.21 | 1.7 | LC1 |
| 24 | 3-(2'-Methoxy-5'-methyl-biphenyl-3-yl)-3-thiazol-2-yl-propionic acid | C2 | A | 0.147 | 354.2 | 1.81 | LC1 |
| 25 | 3-(2'-Ethoxy-5'-methyl-biphenyl-3-yl)-3-thiazol-2-yl-propionic acid | C2 | A | 0.147 | 368.21 | 1.87 | LC1 |
| 26 | 3-(2'-Fluoro-6'-methoxy-biphenyl-3-yl)-3-thiazol-2-yl-propionic acid | C2 | A | 0.148 | 358.16 | 1.72 | LC1 |
| 27 | 3-(2',3'-Difluoro-6'-methoxy-biphenyl-3-yl)-3-thiazol-2-yl-propionic acid | C2 | A | 0.156 | 376.15 | 1.74 | LC1 |
| 28 | 3-(2'-Isopropoxy-6'-methoxy-biphenyl-3-yl)-3-thiazol-2-yl-propionic acid | C2 | A | 0.165 | 398.22 | 1.82 | LC1 |
| 29 | 3-(2',4'-Dimethoxy-biphenyl-3-yl)-3-thiazol-2-yl-propionic acid | C2 | A | 0.185 | 370.19 | 1.73 | LC1 |
| 30 | 3-(4'-Hydroxymethyl-2'-methoxy-biphenyl-3-yl)-3-thiazol-2-yl-propionic acid | C2 | A | 0.201 | 370.19 | 1.5 | LC1 |
| 31 | 3-(2'-Chloro-6'-methoxy-biphenyl-3-yl)-3-thiazol-2-yl-propionic acid | C2 | A | 0.292 | 374.14 | 1.77 | LC1 |
| 32 | 3-(5'-Hydroxy-2'-methoxy-biphenyl-3-yl)-3-thiazol-2-yl-propionic acid | C2 | A | 0.307 | 356.17 | 1.51 | LC1 |
| 33 | 3-(5'-Hydroxymethyl-2'-methoxy-biphenyl-3-yl)-3-thiazol-2-yl-propionic acid | C2 | A | 0.333 | 370.2 | 1.5 | LC1 |
| 34 | 3-(2'-Methoxy-5'-trifluoromethoxy-biphenyl-3-yl)-3-thiazol-2-yl-propionic acid | C2 | A | 0.389 | 424.17 | 1.88 | LC1 |
| 35 | 3-(2'-Isopropoxy-biphenyl-3-yl)-3-thiazol-2-yl-propionic acid | C2 | A | 0.409 | 368.23 | 1.85 | LC1 |
| 36 | 3-(3',5'-Difluoro-2'-methoxy-biphenyl-3-yl)-3-thiazol-2-yl-propionic acid | C2 | A | 0.467 | 376.14 | 1.79 | LC1 |
| 37 | 3-(4'-Fluoro-2'-methoxy-biphenyl-3-yl)-3-thiazol-2-yl-propionic acid | C2 | A | 0.503 | 358.17 | 1.76 | LC1 |
| 38 | 3-(4'-Chloro-2'-methoxy-biphenyl-3-yl)-3-thiazol-2-yl-propionic acid | C2 | A | 0.590 | 374.14 | 1.84 | LC1 |
| 39 | 3-(5'-Cyano-2'-methoxy-biphenyl-3-yl)-3-thiazol-2-yl-propionic acid | C2 | A | 0.618 | 365.18 | 1.65 | LC1 |
| 40 | 3-(2'-Methoxy-3'-methyl-biphenyl-3-yl)-3-thiazol-2-yl-propionic acid | C2 | A | 0.844 | 354.2 | 1.81 | LC1 |
| 41 | 3-(2',3'-Dimethoxy-biphenyl-3-yl)-3-thiazol-2-yl-propionic acid | C2 | A | 0.950 | 370.19 | 1.71 | LC1 |
| 42 | 3-(3'-Fluoro-2'-methoxy-biphenyl-3-yl)-3-thiazol-2-yl-propionic acid | C2 | A | 1.040 | 358.17 | 1.76 | LC1 |
| 43 | 3-Thiazol-2-yl-3-(2'-trifluoromethoxy-biphenyl-3-yl)-propionic acid | C2 | A | 1.230 | 394.14 | 1.84 | LC1 |
| 44 | 3-(3'-Chloro-2'-methoxy-biphenyl-3-yl)-3-thiazol-2-yl-propionic acid | C2 | A | 1.280 | 374.14 | 1.83 | LC1 |
| 45 | 3-(4'-Carbamoyl-2'-methoxy-biphenyl-3-yl)-3-thiazol-2-yl-propionic acid | C2 | A | 1.380 | 383.16 | 1.4 | LC1 |
| 46 | 3-(2'-Methoxy-4'-trifluoromethoxy-biphenyl-3-yl)-3-thiazol-2-yl-propionic acid | C2 | A | 1.530 | 424.18 | 1.89 | LC1 |

TABLE 1-continued

Example compounds of the formula I

| No | CHEMICAL_NAME | Starting material | Suzuki reaction | CATH A IC50 [µM] | Observed Mass | Retention Time [min] | LC-MS Method |
|---|---|---|---|---|---|---|---|
| 47 | 3-(2'-Cyano-6'-methoxy-biphenyl-3-yl)-3-thiazol-2-yl-propionic acid | C2 | A | 1.750 | 365.14 | 3.93 | LC2 |
| 48 | 3-(2'-Methoxy-4'-trifluoromethyl-biphenyl-3-yl)-3-thiazol-2-yl-propionic acid | C2 | A | 2.280 | 408.18 | 1.87 | LC1 |
| 49 | 3-(2'-Methoxy-3'-trifluoromethyl-biphenyl-3-yl)-3-thiazol-2-yl-propionic acid | C2 | A | 7.000 | 408.16 | 1.87 | LC1 |
| 50 | 3-(5'-Chloro-2'-methoxy-biphenyl-3-yl)-3-(5-methyl-[1,3,4]oxadiazol-2-yl)-propionic acid | C1 | A | 0.108 | 373.17 | 1.71 | LC1 |
| 51 | 3-(2',6'-Dimethoxy-biphenyl-3-yl)-3-(5-methyl-thiazol-2-yl)-propionic acid | A6 | A | 0.011 | 382.17 | 1.75 | LC3 |
| 52 | 3-(5-Methyl-thiazol-2-yl)-3-(2',3',6'-trimethoxy-biphenyl-3-yl)-propionic acid | A6 | A | 0.056 | 414.27 | 1.73 | LC1 |
| 53 | 3-(2'-Methoxy-5'-methyl-biphenyl-3-yl)-3-(5-methyl-thiazol-2-yl)-propionic acid | A6 | A | 0.085 | 368.28 | 1.85 | LC1 |
| 54 | 3-(2',5'-Dimethoxy-biphenyl-3-yl)-3-(5-methyl-thiazol-2-yl)-propionic acid | A6 | A | 0.094 | 384.25 | 1.77 | LC1 |
| 55 | 3-(5'-Fluoro-2'-methoxy-biphenyl-3-yl)-3-(5-methyl-thiazol-2-yl)-propionic acid | A6 | A | 0.096 | 372.23 | 1.8 | LC1 |
| 56 | 3-(5'-Isopropyl-2'-methoxy-biphenyl-3-yl)-3-(5-methyl-thiazol-2-yl)-propionic acid | A6 | A | 0.097 | 396.33 | 1.96 | LC1 |
| 57 | 3-(5'-Hydroxymethyl-2'-methoxy-biphenyl-3-yl)-3-(5-methyl-thiazol-2-yl)-propionic acid | A6 | A | 0.131 | 384.25 | 1.56 | LC1 |
| 58 | 3-(2'-Chloro-6'-methoxy-biphenyl-3-yl)-3-(5-methyl-thiazol-2-yl)-propionic acid | A6 | A | 0.155 | 388.2 | 1.81 | LC1 |
| 59 | 3-(2'-Fluoro-6'-methoxy-biphenyl-3-yl)-3-(5-methyl-thiazol-2-yl)-propionic acid | A6 | A | 0.171 | 372.21 | 1.77 | LC1 |
| 60 | 3-(2'-Methoxy-5'-trifluoromethoxy-biphenyl-3-yl)-3-(5-methyl-thiazol-2-yl)-propionic acid | A6 | A | 0.269 | 438.13 | 4.79 | LC2 |
| 61 | 3-(3',5'-Difluoro-2'-methoxy-biphenyl-3-yl)-3-(5-methyl-thiazol-2-yl)-propionic acid | A6 | A | 0.367 | 390.25 | 1.84 | LC1 |
| 62 | 3-(5'-Chloro-2'-methoxy-biphenyl-3-yl)-3-(5-methyl-thiazol-2-yl)-propionic acid | A6 | A | 0.262 | 388.12 | 4.74 | LC2 |
| 63 | 3-(5'-Fluoro-4,2'-dimethoxy-biphenyl-3-yl)-3-(5-methyl-thiazol-2-yl)-propionic acid | P3 | B | 1.170 | 402.15 | 1.8 | LC1 |
| 64 | 3-(5'-Isopropyl-2'-methoxy-biphenyl-3-yl)-3-(5-methyl-[1,3,4]oxadiazol-2-yl)-propionic acid | C1 | A | 0.049 | 381.3 | 1.82 | LC1 |
| 65 | 3-(5'-Chloro-4,2'-dimethoxy-biphenyl-3-yl)-3-(5-methyl-thiazol-2-yl)-propionic acid | P3 | B | 3.050 | 418.11 | 1.87 | LC1 |
| 66 | 3-(4,2'-Dimethoxy-biphenyl-3-yl)-3-(5-methyl-thiazol-2-yl)-propionic acid | P3 | B | 4.410 | 384.16 | 1.78 | LC1 |
| 67 | 3-(4,2'-Dimethoxy-5'-methyl-biphenyl-3-yl)-3-(5-methyl-thiazol-2-yl)-propionic acid | P3 | B | 9.690 | 398.2 | 1.85 | LC1 |
| 68 | 3-(4-Methoxy-2'-trifluoromethoxy-biphenyl-3-yl)-3-(5-methyl-thiazol-2-yl)-propionic acid | P3 | B | ##### | 438.16 | 1.88 | LC1 |
| 69 | 3-(5-Methyl-thiazol-2-yl)-3-(4,2',5'-trimethoxy-biphenyl-3-yl)-propionic acid | P3 | B | ##### | 414.2 | 1.76 | LC1 |

TABLE 1-continued

Example compounds of the formula I

| No | CHEMICAL_NAME | Starting material | Suzuki reaction | CATH A IC50 [μM] | Observed Mass | Retention Time [min] | LC-MS Method |
|----|---------------|-------------------|-----------------|------------------|---------------|----------------------|--------------|
| 70 | 3-(5'-tert-Butyl-4,2'-dimethoxy-biphenyl-3-yl)-3-(5-methyl-thiazol-2-yl)-propionic acid | P3 | B | ##### | 440.25 | 1.99 | LC1 |
| 71 | 3-(5-Chloro-2'-fluoro-6'-methoxy-biphenyl-3-yl)-3-(5-methyl-thiazol-2-yl)-propionic acid | A1 | A | 0.016 | 406.17 | 1.87 | LC1 |
| 72 | 3-(5-Chloro-2',3',6'-trimethoxy-biphenyl-3-yl)-3-(5-methyl-thiazol-2-yl)-propionic acid | A1 | A | 0.018 | 448.24 | 1.83 | LC1 |
| 73 | 3-(5-Chloro-5'-hydroxy-2'-methoxy-biphenyl-3-yl)-3-(5-methyl-thiazol-2-yl)-propionic acid | A1 | A | 0.018 | 404.18 | 1.7 | LC1 |
| 74 | 3-(5-Chloro-2',6'-dimethoxy-4'-methyl-biphenyl-3-yl)-3-(5-methyl-thiazol-2-yl)-propionic acid | A1 | A | 0.019 | 432.2 | 1.9 | LC1 |
| 75 | 3-(5-Chloro-2'-methoxy-biphenyl-3-yl)-3-(5-methyl-thiazol-2-yl)-propionic acid | A1 | A | 0.021 | 388.16 | 1.89 | LC1 |
| 76 | 3-(5-Chloro-2',5'-dimethoxy-biphenyl-3-yl)-3-(5-methyl-thiazol-2-yl)-propionic acid | A1 | A | 0.028 | 418.18 | 1.87 | LC1 |
| 77 | 3-(5-Chloro-5'-hydroxymethyl-2'-methoxy-biphenyl-3-yl)-3-(5-methyl-thiazol-2-yl)-propionic acid | A1 | A | 0.029 | 418.2 | 1.68 | LC1 |
| 78 | 3-(5-Chloro-2',3'-difluoro-6'-methoxy-biphenyl-3-yl)-3-(5-methyl-thiazol-2-yl)-propionic acid | A1 | A | 0.037 | 424.16 | 1.88 | LC1 |
| 79 | 3-(5-Chloro-5'-fluoro-2'-methoxy-biphenyl-3-yl)-3-(5-methyl-thiazol-2-yl)-propionic acid | A1 | A | 0.038 | 406.15 | 1.9 | LC1 |
| 80 | 3-(5-Chloro-2'-ethoxy-biphenyl-3-yl)-3-(5-methyl-thiazol-2-yl)-propionic acid | A1 | A | 0.047 | 402.2 | 1.94 | LC1 |
| 81 | 3-(5-Chloro-2'-methoxy-5'-methyl-biphenyl-3-yl)-3-(5-methyl-thiazol-2-yl)-propionic acid | A1 | A | 0.052 | 402.12 | 1.97 | LC1 |
| 82 | 3-(5-Chloro-2'-hydroxymethyl-6'-methoxy-biphenyl-3-yl)-3-(5-methyl-thiazol-2-yl)-propionic acid | A1 | A | 0.052 | 418.2 | 1.68 | LC1 |
| 83 | 3-(5-Chloro-2',4'-dimethoxy-biphenyl-3-yl)-3-(5-methyl-thiazol-2-yl)-propionic acid | A1 | A | 0.053 | 418.16 | 1.89 | LC1 |
| 84 | 3-(5,2'-Dichloro-6'-methoxy-biphenyl-3-yl)-3-(5-methyl-thiazol-2-yl)-propionic acid | A1 | A | 0.053 | 422.16 | 1.91 | LC1 |
| 85 | 3-(5'-tert-Butyl-5-chloro-2'-methoxy-biphenyl-3-yl)-3-(5-methyl-thiazol-2-yl)-propionic acid | A1 | A | 0.055 | 444.26 | 2.07 | LC1 |
| 86 | 3-(5-Chloro-2'-ethoxy-5'-methyl-biphenyl-3-yl)-3-(5-methyl-thiazol-2-yl)-propionic acid | A1 | A | 0.065 | 416.21 | 2 | LC1 |
| 87 | 3-(5-Chloro-5'-isopropyl-2'-methoxy-biphenyl-3-yl)-3-(5-methyl-thiazol-2-yl)-propionic acid | A1 | A | 0.093 | 430.23 | 2.04 | LC1 |
| 88 | 3-(5-Chloro-2'-cyano-6'-methoxy-biphenyl-3-yl)-3-(5-methyl-thiazol-2-yl)-propionic acid | A1 | A | 0.103 | 413.16 | 1.77 | LC1 |
| 89 | 3-(4'-Carbamoyl-5-chloro-2'-methoxy-biphenyl-3-yl)-3-(5-methyl-thiazol-2-yl)-propionic acid | A1 | A | 0.118 | 431.19 | 1.6 | LC1 |

TABLE 1-continued

Example compounds of the formula I

| No | CHEMICAL_NAME | Starting material | Suzuki reaction | CATH A IC50 [µM] | Observed Mass | Retention Time [min] | LC-MS Method |
|---|---|---|---|---|---|---|---|
| 90 | 3-(5-Chloro-4'-fluoro-2'-methoxy-biphenyl-3-yl)-3-(5-methyl-thiazol-2-yl)-propionic acid | A1 | A | 0.119 | 406.15 | 1.9 | LC1 |
| 91 | 3-(5-Chloro-3',5'-difluoro-2'-methoxy-biphenyl-3-yl)-3-(5-methyl-thiazol-2-yl)-propionic acid | A1 | A | 0.131 | 424.17 | 1.93 | LC1 |
| 92 | 3-(5,3'-Dichloro-2'-methoxy-biphenyl-3-yl)-3-(5-methyl-thiazol-2-yl)-propionic acid | A1 | A | 0.134 | 422.14 | 1.96 | LC1 |
| 93 | 3-(5-Chloro-2'-methoxy-3'-methyl-biphenyl-3-yl)-3-(5-methyl-thiazol-2-yl)-propionic acid | A1 | A | 0.164 | 402.2 | 1.96 | LC1 |
| 94 | 3-(5-Chloro-2'-methoxy-5'-trifluoromethoxy-biphenyl-3-yl)-3-(5-methyl-thiazol-2-yl)-propionic acid | A1 | A | 0.165 | 472.18 | 1.99 | LC1 |
| 95 | 3-(5-Chloro-2'-trifluoromethoxy-biphenyl-3-yl)-3-(5-methyl-thiazol-2-yl)-propionic acid | A1 | A | 0.221 | 442.15 | 1.96 | LC1 |
| 96 | 3-(5-Fluoro-4'-hydroxymethyl-2',6'-dimethoxy-biphenyl-3-yl)-3-oxazol-2-yl-propionic acid | A3 | A | 0.014 | 402.24 | 1.47 | LC1 |
| 97 | 3-(5-Fluoro-2',6'-dimethoxy-4'-methyl-biphenyl-3-yl)-3-oxazol-2-yl-propionic acid | A3 | A | 0.016 | 386.19 | 1.75 | LC1 |
| 98 | 3-(5-Fluoro-2',6'-dimethoxy-biphenyl-3-yl)-3-oxazol-2-yl-propionic acid | A3 | A | 0.018 | 372.14 | 1.68 | LC1 |
| 99 | 3-(5-Fluoro-2',6'-dimethoxy-4'-methyl-biphenyl-3-yl)-3-(5-methyl-thiazol-2-yl)-propionic acid | A3 | A | 0.028 | 416.25 | 1.85 | LC1 |
| 100 | 3-(5-Fluoro-2'-methoxy-5'-methyl-biphenyl-3-yl)-3-(5-methyl-thiazol-2-yl)-propionic acid | A3 | A | 0.052 | 386.21 | 1.89 | LC1 |
| 101 | 3-(5,2'-Difluoro-6'-methoxy-biphenyl-3-yl)-3-(5-methyl-thiazol-2-yl)-propionic acid | A3 | A | 0.056 | 390.18 | 1.81 | LC1 |
| 102 | 3-(5'-tert-Butyl-5-fluoro-2'-methoxy-biphenyl-3-yl)-3-oxazol-2-yl-propionic acid | A3 | A | 0.059 | 398.23 | 1.94 | LC1 |
| 103 | 3-(5-Fluoro-5'-isopropyl-2'-methoxy-biphenyl-3-yl)-3-oxazol-2-yl-propionic acid | A3 | A | 0.085 | 384.23 | 1.9 | LC1 |
| 104 | 3-(5-Fluoro-2'-methoxy-5'-methyl-biphenyl-3-yl)-3-oxazol-2-yl-propionic acid | A3 | A | 0.086 | 356.19 | 1.79 | LC1 |
| 105 | 3-(2'-Chloro-5-fluoro-6'-methoxy-biphenyl-3-yl)-3-(5-methyl-thiazol-2-yl)-propionic acid | A3 | A | 0.096 | 406.15 | 1.85 | LC1 |
| 106 | 3-(2'-Chloro-5-fluoro-6'-methoxy-biphenyl-3-yl)-3-oxazol-2-yl-propionic acid | A3 | A | 0.106 | 376.12 | 1.74 | LC1 |
| 107 | 3-Oxazol-2-yl-3-(5,2',3'-trifluoro-6'-methoxy-biphenyl-3-yl)-propionic acid | A3 | A | 0.107 | 378.14 | 1.72 | LC1 |
| 108 | (S)-3-(5'-Isopropyl-2'-methoxy-biphenyl-3-yl)-3-(5-methyl-[1,3,4]oxadiazol-2-yl)-propionic acid | C1 | A | 6.259 | 381.29 | 1.82 | LC1 |
| 109 | 3-(5,2'-Difluoro-6'-methoxy-biphenyl-3-yl)-3-oxazol-2-yl-propionic acid | A3 | A | 0.108 | 360.14 | 1.7 | LC1 |
| 110 | 3-(5-Fluoro-2'-methoxy-biphenyl-3-yl)-3-(5-methyl-thiazol-2-yl)-propionic acid | A3 | A | 0.116 | 372.17 | 1.82 | LC1 |

TABLE 1-continued

Example compounds of the formula I

| No | CHEMICAL_NAME | Starting material | Suzuki reaction | CATH A IC50 [μM] | Observed Mass | Retention Time [min] | LC-MS Method |
|---|---|---|---|---|---|---|---|
| 111 | 3-(5'-Chloro-5-fluoro-2'-methoxy-biphenyl-3-yl)-3-oxazol-2-yl-propionic acid | A3 | A | 0.118 | 376.1 | 1.8 | LC1 |
| 112 | 3-(5-Fluoro-2',5'-dimethoxy-biphenyl-3-yl)-3-(5-methyl-thiazol-2-yl)-propionic acid | A3 | A | 0.122 | 402.18 | 1.81 | LC1 |
| 113 | 3-(5'-tert-Butyl-5-fluoro-2'-methoxy-biphenyl-3-yl)-3-(5-methyl-thiazol-2-yl)-propionic acid | A3 | A | 0.124 | 428.3 | 2.02 | LC1 |
| 114 | 3-(5-Fluoro-2'-methoxy-biphenyl-3-yl)-3-oxazol-2-yl-propionic acid | A3 | A | 0.137 | 342.16 | 1.71 | LC1 |
| 115 | 3-(5-Fluoro-2',5'-dimethoxy-biphenyl-3-yl)-3-oxazol-2-yl-propionic acid | A3 | A | 0.142 | 372.13 | 1.7 | LC1 |
| 116 | 3-(5-Fluoro-5'-hydroxy-2'-methoxy-biphenyl-3-yl)-3-oxazol-2-yl-propionic acid | A3 | A | 0.147 | 358.13 | 1.5 | LC1 |
| 117 | 3-(2'-Ethoxy-5-fluoro-5'-methyl-biphenyl-3-yl)-3-oxazol-2-yl-propionic acid | A3 | A | 0.155 | 370.22 | 1.85 | LC1 |
| 118 | 3-(5,5'-Difluoro-2'-methoxy-biphenyl-3-yl)-3-oxazol-2-yl-propionic acid | A3 | A | 0.174 | 360.16 | 1.73 | LC1 |
| 119 | 3-(5-Fluoro-5'-isopropyl-2'-methoxy-biphenyl-3-yl)-3-(5-methyl-thiazol-2-yl)-propionic acid | A3 | A | 0.195 | 414.26 | 1.99 | LC1 |
| 120 | 3-(5-Fluoro-2',4'-dimethoxy-biphenyl-3-yl)-3-(5-methyl-thiazol-2-yl)-propionic acid | A3 | A | 0.199 | 402.2 | 1.82 | LC1 |
| 121 | 3-(2'-Ethoxy-5-fluoro-biphenyl-3-yl)-3-oxazol-2-yl-propionic acid | A3 | A | 0.209 | 356.18 | 1.78 | LC1 |
| 122 | 3-(5-Fluoro-2'-methoxy-5'-trifluoromethoxy-biphenyl-3-yl)-3-oxazol-2-yl-propionic acid | A3 | A | 0.222 | 426.16 | 1.85 | LC1 |
| 123 | 3-(5,4'-Difluoro-2'-methoxy-biphenyl-3-yl)-3-(5-methyl-thiazol-2-yl)-propionic acid | A3 | A | 0.246 | 390.18 | 1.84 | LC1 |
| 124 | 3-(5-Fluoro-2'-methoxy-5'-trifluoromethoxy-biphenyl-3-yl)-3-(5-methyl-thiazol-2-yl)-propionic acid | A3 | A | 0.275 | 456.23 | 1.94 | LC1 |
| 125 | 3-(5-Fluoro-5'-hydroxymethyl-2'-methoxy-biphenyl-3-yl)-3-oxazol-2-yl-propionic acid | A3 | A | 0.284 | 372.2 | 1.49 | LC1 |
| 126 | 3-(5-Fluoro-2',4'-dimethoxy-biphenyl-3-yl)-3-oxazol-2-yl-propionic acid | A3 | A | 0.328 | 372.2 | 1.71 | LC1 |
| 127 | 3-(5,4'-Difluoro-2'-methoxy-biphenyl-3-yl)-3-oxazol-2-yl-propionic acid | A3 | A | 0.337 | 360.12 | 1.74 | LC1 |
| 128 | 3-(5-Fluoro-2'-methoxy-3'-methyl-biphenyl-3-yl)-3-(5-methyl-thiazol-2-yl)-propionic acid | A3 | A | 0.410 | 386.21 | 1.9 | LC1 |
| 129 | 3-Oxazol-2-yl-3-(5,3',5'-trifluoro-2'-methoxy-biphenyl-3-yl)-propionic acid | A3 | A | 0.457 | 378.15 | 1.77 | LC1 |
| 130 | 3-(5-Fluoro-2'-trifluoromethoxy-biphenyl-3-yl)-3-oxazol-2-yl-propionic acid | A3 | A | 0.466 | 396.16 | 1.81 | LC1 |
| 131 | 3-(5-Fluoro-2'-methoxy-3'-methyl-biphenyl-3-yl)-3-oxazol-2-yl-propionic acid | A3 | A | 0.474 | 356.18 | 1.79 | LC1 |
| 132 | 3-(5-Fluoro-6'-hydroxymethyl-2'-methoxy-biphenyl-3-yl)-3-oxazol-2-yl-propionic acid | A3 | A | 0.514 | 372.15 | 1.49 | LC1 |
| 133 | 3-(3'-Chloro-5-fluoro-2'-methoxy-biphenyl-3-yl)-3-oxazol-2-yl-propionic acid | A3 | A | 0.815 | 376.13 | 1.8 | LC1 |

TABLE 1-continued

Example compounds of the formula I

| No | CHEMICAL_NAME | Starting material | Suzuki reaction | CATH A IC50 [μM] | Observed Mass | Retention Time [min] | LC-MS Method |
|---|---|---|---|---|---|---|---|
| 134 | 3-(4'-Carbamoyl-5-fluoro-2'-methoxy-biphenyl-3-yl)-3-oxazol-2-yl-propionic acid | A3 | A | 0.960 | 385.21 | 1.4 | LC1 |
| 135 | 3-(2',6'-Dimethoxy-biphenyl-3-yl)-3-(5-methyl-[1,3,4]oxadiazol-2-yl)-propionic acid | C1 | A | 0.017 | 369.22 | 1.58 | LC1 |
| 136 | 3-(2'-Methoxy-5'-methyl-biphenyl-3-yl)-3-(5-methyl-[1,3,4]oxadiazol-2-yl)-propionic acid | C1 | A | 0.024 | 353.22 | 1.69 | LC1 |
| 137 | 3-(2',6'-Dimethoxy-4'-methyl-biphenyl-3-yl)-3-(5-methyl-[1,3,4]oxadiazol-2-yl)-propionic acid | C1 | A | 0.024 | 383.24 | 1.66 | LC1 |
| 138 | 3-(2',5'-Dimethoxy-biphenyl-3-yl)-3-(5-methyl-[1,3,4]oxadiazol-2-yl)-propionic acid | C1 | A | 0.041 | 369.2 | 1.59 | LC1 |
| 139 | 3-(5'-Fluoro-2'-methoxy-biphenyl-3-yl)-3-(5-methyl-[1,3,4]oxadiazol-2-yl)-propionic acid | C1 | A | 0.060 | 357.19 | 1.63 | LC1 |
| 140 | 3-(2'-Methoxy-biphenyl-3-yl)-3-(5-methyl-[1,3,4]oxadiazol-2-yl)-propionic acid | C1 | A | 0.061 | 339.21 | 1.61 | LC1 |
| 141 | 3-(5'-Hydroxymethyl-2'-methoxy-biphenyl-3-yl)-3-(5-methyl-[1,3,4]oxadiazol-2-yl)-propionic acid | C1 | A | 0.072 | 369.2 | 1.38 | LC1 |
| 142 | 3-(2'-Chloro-6'-methoxy-biphenyl-3-yl)-3-(5-methyl-[1,3,4]oxadiazol-2-yl)-propionic acid | C1 | A | 0.080 | 373.18 | 1.65 | LC1 |
| 143 | 3-(2'-Methoxy-5'-trifluoromethoxy-biphenyl-3-yl)-3-(5-methyl-[1,3,4]oxadiazol-2-yl)-propionic acid | C1 | A | 0.085 | 423.21 | 1.77 | LC1 |
| 144 | 3-(2'-Ethoxy-biphenyl-3-yl)-3-(5-methyl-[1,3,4]oxadiazol-2-yl)-propionic acid | C1 | A | 0.091 | 353.23 | 1.69 | LC1 |
| 145 | 3-(2'-Fluoro-6'-methoxy-biphenyl-3-yl)-3-(5-methyl-[1,3,4]oxadiazol-2-yl)-propionic acid | C1 | A | 0.116 | 357.19 | 1.6 | LC1 |
| 146 | 3-(4'-Fluoro-2'-methoxy-biphenyl-3-yl)-3-(5-methyl-[1,3,4]oxadiazol-2-yl)-propionic acid | C1 | A | 0.129 | 357.19 | 1.64 | LC1 |
| 147 | 3-(2',4'-Dimethoxy-biphenyl-3-yl)-3-(5-methyl-[1,3,4]oxadiazol-2-yl)-propionic acid | C1 | A | 0.137 | 369.22 | 1.61 | LC1 |
| 148 | 3-(5-Methyl-[1,3,4]oxadiazol-2-yl)-3-(2'-trifluoromethoxy-biphenyl-3-yl)-propionic acid | C1 | A | 0.243 | 393.18 | 1.73 | LC1 |
| 149 | 3-(5'-Methanesulfonyl-2'-methoxy-biphenyl-3-yl)-3-(5-methyl-[1,3,4]oxadiazol-2-yl)-propionic acid | C1 | A | 0.265 | 417.19 | 1.39 | LC1 |
| 150 | 3-(6'-Hydroxymethyl-2'-methoxy-biphenyl-3-yl)-3-(5-methyl-[1,3,4]oxadiazol-2-yl)-propionic acid | C1 | A | 0.325 | 369.21 | 1.37 | LC1 |
| 151 | 3-(2'-Methoxy-3'-methyl-biphenyl-3-yl)-3-(5-methyl-[1,3,4]oxadiazol-2-yl)-propionic acid | C1 | A | 0.571 | 353.23 | 1.69 | LC1 |
| 152 | 3-(2'-Cyano-6'-methoxy-biphenyl-3-yl)-3-(5-methyl-[1,3,4]oxadiazol-2-yl)-propionic acid | C1 | A | 0.652 | 364.16 | 1.51 | LC1 |
| 153 | 3-(5-Chloro-5'-isopropyl-2'-methoxy-biphenyl-3-yl)-3-(5- | A8 | A | 0.025 | 415.22 | 4.79 | LC2 |

TABLE 1-continued

Example compounds of the formula I

| No | CHEMICAL_NAME | Starting material | Suzuki reaction | CATH A IC50 [μM] | Observed Mass | Retention Time [min] | LC-MS Method |
|---|---|---|---|---|---|---|---|
|  | methyl-[1,3,4]oxadiazol-2-yl)-propionic acid |  |  |  |  |  |  |
| 154 | 3-(5-Chloro-2',6'-dimethoxy-biphenyl-3-yl)-3-(5-methyl-[1,3,4]oxadiazol-2-yl)-propionic acid | A8 | A | 0.005 | 403.2 | 4.18 | LC2 |
| 155 | 3-(5-Chloro-2',6'-dimethoxy-4'-methyl-biphenyl-3-yl)-3-(5-methyl-[1,3,4]oxadiazol-2-yl)-propionic acid | A8 | A | 0.008 | 417.23 | 4.42 | LC2 |
| 156 | 3-(5-Chloro-2'-cyano-6'-methoxy-biphenyl-3-yl)-3-(5-methyl-[1,3,4]oxadiazol-2-yl)-propionic acid | A8 | A | 0.104 | 398.19 | 3.95 | LC2 |
| 157 | 3-[3-Chloro-5-(6-methoxy-2,2-dimethyl-2,3-dihydro-benzofuran-7-yl)-phenyl]-3-(5-methyl-[1,3,4]oxadiazol-2-yl)-propionic acid | A8 | A | 0.017 | 443.23 | 4.63 | LC2 |
| 158 | 3-(5-Chloro-2'-trifluoromethoxy-biphenyl-3-yl)-3-(5-methyl-[1,3,4]oxadiazol-2-yl)-propionic acid | A8 | A | 0.089 | 427.18 | 4.59 | LC2 |
| 159 | 3-(5'-tert-Butyl-5-fluoro-2'-methoxy-biphenyl-3-yl)-3-(5-methyl-[1,3,4]oxadiazol-2-yl)-propionic acid | A9 | A |  | 413.27 | 4.76 | LC2 |
| 160 | 3-(5-Fluoro-5'-isopropyl-2'-methoxy-biphenyl-3-yl)-3-(5-methyl-[1,3,4]oxadiazol-2-yl)-propionic acid | A9 | A | 0.044 | 399.3 | 4.68 | LC2 |
| 161 | 3-(5-Fluoro-2',6'-dimethoxy-biphenyl-3-yl)-3-(5-methyl-[1,3,4]oxadiazol-2-yl)-propionic acid | A9 | A |  | 387.21 | 3.97 | LC2 |
| 162 | 3-(5-Fluoro-2',6'-dimethoxy-4'-methyl-biphenyl-3-yl)-3-(5-methyl-[1,3,4]oxadiazol-2-yl)-propionic acid | A9 | A |  | 401.25 | 4.21 | LC2 |
| 163 | 3-(2'-Cyano-5-fluoro-6'-methoxy-biphenyl-3-yl)-3-(5-methyl-[1,3,4]oxadiazol-2-yl)-propionic acid | A9 | A | 0.446 | 382.21 | 3.75 | LC2 |
| 164 | 3-[3-Fluoro-5-(6-methoxy-2,2-dimethyl-2,3-dihydro-benzofuran-7-yl)-phenyl]-3-(5-methyl-[1,3,4]oxadiazol-2-yl)-propionic acid | A9 | A |  | 427.31 | 4.47 | LC2 |
| 165 | 3-(5-Fluoro-2'-trifluoromethoxy-biphenyl-3-yl)-3-(5-methyl-[1,3,4]oxadiazol-2-yl)-propionic acid | A9 | A | 0.231 | 411.19 | 4.43 | LC2 |
| 166 | 3-(5'-Chloro-5-fluoro-2'-methoxy-biphenyl-3-yl)-3-(5-methyl-[1,3,4]oxadiazol-2-yl)-propionic acid | A9 | A | 0.089 | 391.18 | 4.37 | LC2 |
| 167 | 3-(5-Fluoro-6'-hydroxymethyl-2'-methoxy-biphenyl-3-yl)-3-(5-methyl-[1,3,4]oxadiazol-2-yl)-propionic acid | A9 | A | 0.400 | 387.21 | 3.35 | LC2 |
| 168 | 3-(5-Fluoro-2'-methoxy-5'-trifluoromethoxy-biphenyl-3-yl)-3-(5-methyl-[1,3,4]oxadiazol-2-yl)-propionic acid | A9 | A | 0.165 | 441.21 | 4.55 | LC2 |
| 169 | 3-(5-Chloro-2'-methoxy-5'-methyl-biphenyl-3-yl)-3-(5-methyl-[1,3,4]oxadiazol-2-yl)-propionic acid | A8 | A | 0.017 | 387.21 | 4.55 | LC2 |
| 170 | 3-(5-Chloro-5'-methanesulfonyl-2'-methoxy-biphenyl-3-yl)-3-(5-methyl-[1,3,4]oxadiazol-2-yl)-propionic acid | A8 | A | 0.109 | 451.22 | 3.61 | LC2 |

TABLE 1-continued

Example compounds of the formula I

| No | CHEMICAL_NAME | Starting material | Suzuki reaction | CATH A IC50 [µM] | Observed Mass | Retention Time [min] | LC-MS Method |
|---|---|---|---|---|---|---|---|
| 171 | 3-[5-Chloro-6'-methoxy-2'-(pyrrolidine-1-carbonyl)-biphenyl-3-yl]-3-(5-methyl-[1,3,4]oxadiazol-2-yl)-propionic acid | A8 | A | 4.21 | 470.26 | 3.66 | LC2 |
| 172 | 3-(5-Chloro-2',4'-dimethoxy-biphenyl-3-yl)-3-(5-methyl-[1,3,4]oxadiazol-2-yl)-propionic acid | A8 | A | 0.033 | 403.2 | 4.28 | LC2 |
| 173 | 3-(5-Fluoro-2'-methoxy-5'-methyl-biphenyl-3-yl)-3-(5-methyl-[1,3,4]oxadiazol-2-yl)-propionic acid | A9 | A |  | 371.22 | 4.32 | LC2 |
| 174 | 3-[5-Fluoro-6'-methoxy-2'-(pyrrolidine-1-carbonyl)-biphenyl-3-yl]-3-(5-methyl-[1,3,4]oxadiazol-2-yl)-propionic acid | A9 | A | 5.26 | 454.27 | 3.44 | LC2 |
| 175 | 3-(2'-Ethoxy-5-fluoro-biphenyl-3-yl)-3-(5-methyl-[1,3,4]oxadiazol-2-yl)-propionic acid | A9 | A | 0.104 | 371.22 | 4.3 | LC2 |
| 176 | 3-(5-Chloro-2'-methoxy-biphenyl-3-yl)-3-(5-methyl-[1,3,4]oxadiazol-2-yl)-propionic acid | A8 | A | 0.010 | 373.17 | 4.27 | LC2 |
| 177 | 3-(5-Chloro-2'-ethoxy-biphenyl-3-yl)-3-(5-methyl-[1,3,4]oxadiazol-2-yl)-propionic acid | A8 | A | 0.024 | 387.21 | 4.53 | LC2 |
| 178 | 3-(5-Fluoro-5'-methanesulfonyl-2'-methoxy-biphenyl-3-yl)-3-(5-methyl-[1,3,4]oxadiazol-2-yl)-propionic acid | A9 | A | 0.588 | 435.23 | 3.42 | LC2 |
| 179 | 3-(5,2'-Difluoro-6'-methoxy-biphenyl-3-yl)-3-(5-methyl-[1,3,4]oxadiazol-2-yl)-propionic acid | A9 | A | 0.067 | 375.19 | 4.03 | LC2 |
| 180 | 3-[5-(2,5-Dimethoxy-phenyl)-pyridin-3-yl]-3-(5-methyl-[1,3,4]oxadiazol-2-yl)-propionic acid | A10 | A | 3.52 | 370.19 | 1.27 | LC1 |
| 181 | 3-[5-(2-Methoxy-5-methyl-phenyl)-pyridin-3-yl]-3-(5-methyl-[1,3,4]oxadiazol-2-yl)-propionic acid | A10 | A | 2.22 | 354.17 | 1.37 | LC1 |
| 182 | 3-[5-(5-tert-Butyl-2-methoxy-phenyl)-pyridin-3-yl]-3-(5-methyl-[1,3,4]oxadiazol-2-yl)-propionic acid | A10 | A | 0.452 | 396.27 | 1.62 | LC1 |
| 183 | 3-[5-(5-Isopropyl-2-methoxy-phenyl)-pyridin-3-yl]-3-(5-methyl-[1,3,4]oxadiazol-2-yl)-propionic acid | A10 | A | 1.03 | 382.23 | 1.56 | LC1 |
| 184 | 3-[5-(2,6-Dimethoxy-phenyl)-pyridin-3-yl]-3-(5-methyl-[1,3,4]oxadiazol-2-yl)-propionic acid | A10 | A | 0.160 | 370.19 | 1.21 | LC1 |
| 185 | (R)-3-(5'-Isopropyl-2'-methoxy-biphenyl-3-yl)-3-(5-methyl-[1,3,4]oxadiazol-2-yl)-propionic acid | C1 | A | 0.027 | 381.28 | 1.82 | LC1 |
| 186 | 3-[5-(2,6-Dimethoxy-4-methyl-phenyl)-pyridin-3-yl]-3-(5-methyl-[1,3,4]oxadiazol-2-yl)-propionic acid | A10 | A | 0.343 | 384.22 | 1.32 | LC1 |
| 187 | 3-[5-(6-Methoxy-32,2-dimethyl-2,3-dihydro-benzofuran-7-yl)-pyridin-3-yl]-3-(5-methyl-[1,3,4]oxadiazol-2-yl)-propionic acid | A10 | A |  | 410.26 | 1.45 | LC1 |
| 188 | 3-[5-(5-Methanesulfonyl-2-methoxy-phenyl)-pyridin-3-yl]- | A10 | A |  | 418.16 | 1.04 | LC1 |

TABLE 1-continued

Example compounds of the formula I

| No | CHEMICAL_NAME | Starting material | Suzuki reaction | CATH A IC50 [μM] | Observed Mass | Retention Time [min] | LC-MS Method |
|---|---|---|---|---|---|---|---|
|  | 3-(5-methyl-[1,3,4]oxadiazol-2-yl)-propionic acid | | | | | | |
| 189 | 3-{5-[2-Methoxy-6-(pyrrolidine-1-carbonyl)-phenyl]-pyridin-3-yl}-3-(5-methyl-[1,3,4]oxadiazol-2-yl)-propionic acid | A10 | A | | 437.27 | 1.2 | LC1 |
| 190 | 3-[5-(2-Methoxy-phenyl)-pyridin-3-yl]-3-(5-methyl-[1,3,4]oxadiazol-2-yl)-propionic acid | A10 | A | 5.8 | 340.12 | 1.23 | LC1 |
| 191 | 3-[5-(5-Chloro-2-methoxy-phenyl)-pyridin-3-yl]-3-(5-methyl-[1,3,4]oxadiazol-2-yl)-propionic acid | A10 | A | 3.91 | 374.11 | 1.44 | LC1 |
| 192 | 3-[5-(5-Fluoro-2-methoxy-phenyl)-pyridin-3-yl]-3-(5-methyl-[1,3,4]oxadiazol-2-yl)-propionic acid | A10 | A | 7.07 | 358.13 | 1.32 | LC1 |
| 193 | 3-[5-(2-Ethoxy-phenyl)-pyridin-3-yl]-3-(5-methyl-[1,3,4]oxadiazol-2-yl)-propionic acid | A10 | A | 4.27 | 354.17 | 1.34 | LC1 |
| 194 | 3-[5-(2,4-Dimethoxy-phenyl)-pyridin-3-yl]-3-(5-methyl-[1,3,4]oxadiazol-2-yl)-propionic acid | A10 | A | 7.14 | 370.18 | 1.22 | LC1 |
| 195 | 3-[5-(2-Fluoro-6-methoxy-phenyl)-pyridin-3-yl]-3-(5-methyl-[1,3,4]oxadiazol-2-yl)-propionic acid | A10 | A | 3.90 | 358.17 | 1.3 | LC1 |
| 196 | 3-[5-(2-Hydroxymethyl-6-methoxy-phenyl)-pyridin-3-yl]-3-(5-methyl-[1,3,4]oxadiazol-2-yl)-propionic acid | A10 | A | | 370.18 | 0.91 | LC1 |
| 197 | 3-[5-(2-Methoxy-5-trifluoromethoxy-phenyl)-pyridin-3-yl]-3-(5-methyl-[1,3,4]oxadiazol-2-yl)-propionic acid | A10 | A | 4.76 | 424.16 | 1.54 | LC1 |
| 198 | 3-[5-(2-Methoxy-3-methyl-phenyl)-pyridin-3-yl]-3-(5-methyl-[1,3,4]oxadiazol-2-yl)-propionic acid | A10 | A | | 354.21 | 1.36 | LC1 |
| 199 | 3-[5-(2-Chloro-6-methoxy-phenyl)-pyridin-3-yl]-3-(5-methyl-[1,3,4]oxadiazol-2-yl)-propionic acid | A10 | A | 3.56 | 374.14 | 1.37 | LC1 |
| 200 | 3-(4'-Fluoro-2'-methoxy-5-trifluoromethyl-biphenyl-3-yl)-3-(5-methyl-[1,3,4]oxadiazol-2-yl)-propionic acid | A1 | A | 0.035 | 425.16 | 1.76 | LC1 |
| 201 | 3-(2',5'-Dimethoxy-5-trifluoromethyl-biphenyl-3-yl)-3-(5-methyl-[1,3,4]oxadiazol-2-yl)-propionic acid | A1 | A | 0.014 | 437.19 | 1.73 | LC1 |
| 202 | 3-(2'-Methoxy-5'-methyl-5-trifluoromethyl-biphenyl-3-yl)-3-(5-methyl-[1,3,4]oxadiazol-2-yl)-propionic acid | A1 | A | 0.017 | 421.19 | 1.82 | LC1 |
| 203 | 3-(5'-tert-Butyl-2'-methoxy-5-trifluoromethyl-biphenyl-3-yl)-3-(5-methyl-[1,3,4]oxadiazol-2-yl)-propionic acid | A1 | A | 0.017 | 463.25 | 1.95 | LC1 |
| 204 | 3-(5'-Isopropyl-2'-methoxy-5-trifluoromethyl-biphenyl-3-yl)-3-(5-methyl-[1,3,4]oxadiazol-2-yl)-propionic acid | A1 | A | 0.031 | 449.22 | 1.92 | LC1 |
| 205 | 3-(2',6'-Dimethoxy-5-trifluoromethyl-biphenyl-3-yl)-3-(5-methyl-[1,3,4]oxadiazol-2-yl)-propionic acid | A1 | A | 0.002 | 437.21 | 1.72 | LC1 |
| 206 | 3-(2',6'-Dimethoxy-4'-methyl-5-trifluoromethyl-biphenyl-3-yl)-3- | A1 | A | 0.006 | 451.21 | 1.79 | LC1 |

TABLE 1-continued

Example compounds of the formula I

| No | CHEMICAL_NAME | Starting material | Suzuki reaction | CATH A IC50 [µM] | Observed Mass | Retention Time [min] | LC-MS Method |
|---|---|---|---|---|---|---|---|
|  | (5-methyl-[1,3,4]oxadiazol-2-yl)-propionic acid |  |  |  |  |  |  |
| 207 | 3-[3-(6-Methoxy-2,2-dimethyl-2,3-dihydro-benzofuran-7-yl)-5-trifluoromethyl-phenyl]-3-(5-methyl-[1,3,4]oxadiazol-2-yl)-propionic acid | A1 | A | 0.010 | 477.23 | 1.85 | LC1 |
| 208 | 3-(5-Methyl-[1,3,4]oxadiazol-2-yl)-3-(2'-trifluoromethoxy-5-trifluoromethyl-biphenyl-3-yl)-propionic acid | A1 | A | 0.065 | 461.15 | 1.82 | LC1 |
| 209 | 3-(5'-Chloro-2'-methoxy-5-trifluoromethyl-biphenyl-3-yl)-3-(5-methyl-[1,3,4]oxadiazol-2-yl)-propionic acid | A1 | A | 0.017 | 441.14 | 1.82 | LC1 |
| 210 | 3-(2'-Ethoxy-5-trifluoromethyl-biphenyl-3-yl)-3-(5-methyl-[1,3,4]oxadiazol-2-yl)-propionic acid | A1 | A | 0.014 | 421.19 | 1.81 | LC1 |
| 211 | 3-(2',4'-Dimethoxy-5-trifluoromethyl-biphenyl-3-yl)-3-(5-methyl-[1,3,4]oxadiazol-2-yl)-propionic acid | A1 | A | 0.023 | 437.18 | 1.74 | LC1 |
| 212 | 3-(2'-Fluoro-6'-methoxy-5-trifluoromethyl-biphenyl-3-yl)-3-(5-methyl-[1,3,4]oxadiazol-2-yl)-propionic acid | A1 | A | 0.008 | 425.16 | 1.73 | LC1 |
| 213 | 3-(2'-Methoxy-5'-trifluoromethoxy-5-trifluoromethyl-biphenyl-3-yl)-3-(5-methyl-[1,3,4]oxadiazol-2-yl)-propionic acid | A1 | A | 0.051 | 491.15 | 1.86 | LC1 |
| 214 | 3-(2'-Chloro-6'-methoxy-5-trifluoromethyl-biphenyl-3-yl)-3-(5-methyl-[1,3,4]oxadiazol-2-yl)-propionic acid | A1 | A | 0.017 | 441.15 | 1.77 | LC1 |
| 215 | 3-(5'-Methanesulfonyl-2'-methoxy-5-trifluoromethyl-biphenyl-3-yl)-3-(5-methyl-[1,3,4]oxadiazol-2-yl)-propionic acid | A1 | A | 0.13 | 485.14 | 1.55 | LC1 |
| 216 | 3-[6'-Methoxy-2'-(pyrrolidine-1-carbonyl)-5-trifluoromethyl-biphenyl-3-yl]-3-(5-methyl-[1,3,4]oxadiazol-2-yl)-propionic acid | A1 | A | 1.46 | 504.24 | 1.6 | LC1 |
| 217 | 3-(2'-Methoxy-5-trifluoromethyl-biphenyl-3-yl)-3-(5-methyl-[1,3,4]oxadiazol-2-yl)-propionic acid | A1 | A | 0.013 | 407.17 | 1.74 | LC1 |
| 218 | 3-(5'-Fluoro-2'-methoxy-5-trifluoromethyl-biphenyl-3-yl)-3-(5-methyl-[1,3,4]oxadiazol-2-yl)-propionic acid | A1 | A | 0.012 | 425.15 | 1.75 | LC1 |
| 219 | 3-(6'-Hydroxymethyl-2'-methoxy-5-trifluoromethyl-biphenyl-3-yl)-3-(5-methyl-[1,3,4]oxadiazol-2-yl)-propionic acid | A1 | A | 0.073 | 437.19 | 1.55 | LC1 |
| 220 | 3-(2'-Methoxy-3'-methyl-5-trifluoromethyl-biphenyl-3-yl)-3-(5-methyl-[1,3,4]oxadiazol-2-yl)-propionic acid | A1 | A | 0.053 | 421.2 | 1.81 | LC1 |
| 221 | 3-(5'-Hydroxymethyl-2'-methoxy-5-trifluoromethyl-biphenyl-3-yl)-3-(5-methyl-[1,3,4]oxadiazol-2-yl)-propionic acid | A1 | A | 0.022 | 437.13 | 1.54 | LC1 |
| 222 | 3-[5'-(Cyano-dimethyl-methyl)-5-fluoro-2'-methoxy-biphenyl-3-yl]-3-(5-methyl- | A9 | A | 0.004 | 424.11 | 1.68 | LC1 |

TABLE 1-continued

Example compounds of the formula I

| No | CHEMICAL_NAME | Starting material | Suzuki reaction | CATH A IC50 [μM] | Observed Mass | Retention Time [min] | LC-MS Method |
|---|---|---|---|---|---|---|---|
| | [1,3,4]oxadiazol-2-yl)-propionic acid | | | | | | |

(1) Mass spectroscopic characterization; observed mass number of the ion [(M + H)⁺], unless specified otherwise
(2) Cathepsin A inhibitory activity determined in the pharmacological test "Cathepsin A inhibitory activity" described below. "A" means an IC$_{50}$ value of less than 0.1 μM, "B" means an IC$_{50}$ value between 0.1 μM and 1 μM, "C" means an IC$_{50}$ value between 1 μM and 30 μM.

Pharmacological Tests
a) Cathepsin a Inhibitory Activity

Recombinant human cathepsin A (residues 29-480, with a C-terminal 10-His tag; R&D Systems, #1049-SE) was proteolytically activated with recombinant human cathepsin L (R&D Systems, #952-CY). Briefly, cathepsin A was incubated at 10 μg/ml with cathepsin L at 1 μg/ml in activation buffer (25 mM 2-(morpholin-4-yl)-ethanesulfonic acid (MES), pH 6.0, containing 5 mM dithiothreitol (DTT)) for 15 min at 37° C. Cathepsin L activity was then stopped by the addition of the cysteine protease inhibitor E-64 (N-(trans-epoxysuccinyl)-L-leucine-4-guanidinobutylamide; Sigma-Aldrich, # E3132; dissolved in activation buffer/DMSO) to a final concentration of 10 μM.

The activated cathepsin A was diluted in assay buffer (25 mM MES, pH 5.5, containing 5 mM DTT) and mixed with the test compound (dissolved in assay buffer containing (v/v) 3% DMSO) or, in the control experiments, with the vehicle in a multiple assay plate. After incubation for 15 min at room temperature, as substrate then bradykinin carrying an N-terminal ®Bodipy FL (4,4-difluoro-5,7-dimethyl-4-bora-3a,4a-diaza-s-indacene-3-propionyl) label (JPT Peptide Technologies GmbH; dissolved in assay buffer) was added to the mixture. The final concentration of cathepsin A was 833 ng/ml and the final concentration of labeled bradykinin 2 μM. After incubation for 15 min at room temperature the reaction was stopped by the addition of stop buffer (130 mM 2-(4-(2-hydroxy-ethyl)-piperazin-1-yl)-ethanesulfonic acid, pH 7.4, containing (v/v) 0.013% ®Triton X-100, 0.13% Coating Reagent 3 (Caliper Life Sciences), 6.5% DMSO and 20 μM ebelactone B (Sigma, # E0886)).

Uncleaved substrate and product were then separated by a microfluidic capillary electrophoresis on a LabChip® 3000 Drug Discovery System (12-Sipper-Chip; Caliper Life Sciences) and quantified by determination of the respective peak areas. Substrate turnover was calculated by dividing product peak area by the sum of substrate and product peak areas, and the enzyme activity and the inhibitory effect of the test compound thus quantified. From the percentage of inhibition of cathepsin A activity observed with the test compound at several concentrations, the inhibitory concentration IC$_{50}$, i.e. the concentration which effects 50% inhibition of enzyme activity was, calculated. IC$_{50}$ values of various example compounds are given in Table 1, wherein "A" means an IC$_{50}$ value of less than 0.1 μM, "B" means an IC$_{50}$ value between 0.1 μM and 1 μM, and "C" means an IC$_{50}$ value between 1 μM and 30 μM.

B) In Vivo Antihypertrophic and Renoprotective Activity

The in vivo pharmacological activity of the compounds of the invention can be investigated, for example, in the model of DOCA-salt sensitive rats with unilateral nephrectomy. Briefly, in this model unilateral nephrectomy of the left kidney (UNX) is performed on Sprague Dawley rats of 150 g to 200 g of body weight. After the operation as well as at the beginning of each of the following weeks 30 mg/kg of body weight of DOCA (desoxycorticosterone acetate) are administered to the rats by subcutaneous injection. The nephrectomized rats treated with DOCA are supplied with drinking water containing 1% of sodium chloride (UNX/DOCA rats). The UNX/DOCA rats develop high blood pressure, endothelial dysfunction, myocardial hypertrophy and fibrosis as well as renal dysfunction. In the test group (UNX/DOCA Test) and the placebo group (UNX/DOCA Placebo), which consist of randomized UNX/DOCA rats, the rats are treated orally by gavage in two part administrations at 6 a.m. and 6 p.m. with the daily dose of the test compound (for example 10 mg/kg of body weight dissolved in vehicle) or with vehicle only, respectively. In a control group (control), which consists of animals which have not been subjected to UNX and DOCA administration, the animals receive normal drinking water and are treated with vehicle only. After five weeks of treatment, systolic blood pressure (SBP) and heart rate (HR) are measured non-invasively via the tail cuff method. For determination of albuminuria and creatinine, 24 h urine is collected on metabolic cages. Endothelial function is assessed in excised rings of the thoracic aorta as described previously (W. Linz et al., JRAAS (Journal of the renin-angiotensin-aldosterone system) 7 (2006), 155-161). As a measure of myocardial hypertrophy and fibrosis, heart weight, left ventricular weight and the relation of hydroxyproline and proline are determined in excised hearts.

The invention claimed is:
1. A compound of the formula I, in any of its stereoisomeric forms or a mixture of stereoisomeric forms in any ratio, or a physiologically acceptable salt thereof, or a physiologically acceptable solvate of any of them,

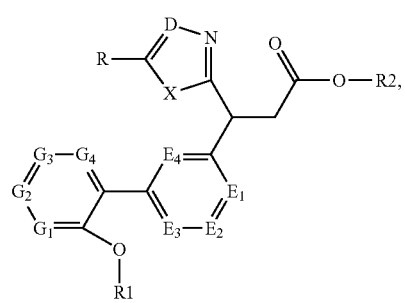

I wherein
X is S or O;
D is N or —C(R3)=;
R is H, (C$_1$-C$_6$)-alkyl or (C$_3$-C$_8$)-cycloalkyl;
R1 is H, (C$_1$-C$_6$)-alkyl, (C$_3$-C$_8$)-cycloalkyl or (C$_1$-C$_6$)-alkylen-(C$_3$-C$_8$)-cycloalkyl;

wherein alkyl is optionally substituted by one or more F-atoms;
R3 is H, methyl or ethyl;
R2 is H or ($C_1$-$C_6$-)-alkyl;
$E_1$ is N or —C(R4)=;
$E_2$ is N or —C(R5)=;
$E_3$ is N or —C(R6)=;
$E_4$ is N or —C(R7)=;
wherein none or one of $E_1$, $E_2$, $E_3$ or $E_4$ is N;
R4 is H or O—($C_1$-$C_6$)-alkyl;
R5 is H F, Cl, $CF_3$, ($C_1$-$C_6$)-alkyl or ($C_1$-$C_6$)-cycloalkyl;
R6 is H;
R7 is H;
$G_1$ is N or —C(R8)=;
$G_2$ is N or —C(R9)=;
$G_3$ is N or —C(R10)=;
$G_4$ is N or —C(R11)=; wherein
none or one of $G_1$, $G_2$, $G_3$ or $G_4$ is N; or $G_3$ and $G_4$ are —C(R10)= and —C(R11)=,
wherein R10 and R11 form a 4 to 7 membered saturated carbocycle or heterocycle with one or two oxygen atoms;
wherein the carbocycle or heterocycle is optionally mono- or disubstituted by halogen and or ($C_1$-$C_3$)-alkyl;
R8 is H, F, Cl, ($C_1$-$C_6$)-alkyl, O—($C_1$-$C_6$)-alkyl, $CF_3$ or $OCF_3$;
R9 is H, F, Cl, OH, O—($C_1$-$C_6$)-alkyl, $CH_2OH$, CO—$NH_2$, ($C_1$-$C_6$)-alkyl, O—($C_1$-$C_6$)-alkyl, $CF_3$ or $OCF_3$;
R10 is H, F, Cl, OH, ($C_1$-$C_6$)-alkyl, $CH_2OH$, CO—O—($C_1$-$C_6$)-alkyl, $SO_2$—($C_1$-$C_6$)-alkyl, CN, O—($C_1$-$C_6$)-alkyl, $CF_3$ or $OCF_3$;
R11 is H, F, Cl, OH, O—($C_1$-$C_6$)-alkyl, $CH_2OH$, CO—($C_1$-$C_6$)-alkyl, CO—N(R20R21), CO—O—($C_1$-$C_6$)-alkyl, CN, ($C_1$-$C_6$)-alkyl, O—($C_1$-$C_6$)-alkyl or $OCF_3$;
wherein R20 and R21 are independently from each other H or ($C_1$-$C_3$)-alkyl or form together with the nitrogen to which they are attached a 5 or 6 membered saturated ring.

2. The compound claim 1, in any of its stereoisomeric forms or a mixture of stereoisomeric forms in any ratio, or a physiologically acceptable salt thereof, or a physiologically acceptable solvate of any of them, wherein R2 is H.

3. The compound of the claim 1, in any of its stereoisomeric forms or a mixture of stereoisomeric forms in any ratio, or a physiologically acceptable salt thereof, or a physiologically acceptable solvate of any of them,
wherein
R is H, methyl or ethyl;
R1 is H, methyl, ethyl, $CF_3$, —$CH_2$-cyclopropyl or —$CH_2$—C($CH_3$)$_3$;
R2 is H;
R4 is H or O-methyl;
R5 is H F, Cl, $CF_3$, ($C_1$-$C_6$)-alkyl, cyclopropyl;
R8 is H, F, Cl, methyl, O-methyl, $CF_3$ or $OCF_3$;
R9 is H, F, Cl, OH, O-propyl, $CH_2OH$, CO—$NH_2$, methyl, O-methyl, $CF_3$ or $OCF_3$;
R10 is H, F, Cl, OH, i-propyl, t-butyl, $CH_2OH$, CO—O-methyl, $SO_2$-methyl, CN, methyl, O-methyl, $CF_3$ or $OCF_3$;
R11 is H, F, Cl, OH, O-methyl, O-i-propyl, $CH_2OH$, CO-methyl, CO—N(methyl)$_2$, CO-pyrrolidin-1-yl, CO—O-methyl, CN, methyl or $OCF_3$.

4. The compound of the claim 1, in any of its stereoisomeric forms or a mixture of stereoisomeric forms in any ratio, or a physiologically acceptable salt thereof, or a physiologically acceptable solvate of any of them,
wherein
$G_3$ and $G_4$ are —C(R10)= and —C(R11)=,
wherein R10 and R11 form a 5 or 6 membered saturated carbocycle or heterocycle with one or two oxygen atoms,
wherein the carbocycle or heterocycle is optionally mono- or disubstituted by halogen and or ($C_1$-$C_3$)-alkyl.

5. The compound of claim 1, having the formula I-1 or I-11

I-1

I-11 in any of its stereoisomeric forms or a mixture of stereoisomeric forms in any ratio, or a physiologically acceptable salt thereof, or a physiologically acceptable solvate of any of them,
wherein
$G_1$ is —C(R8)=;
$G_2$ is —C(R9)=;
$G_3$ is —C(R10)=; and
$G_4$ is —C(R11)=.

6. A compound that is:
(S)-3-(5'-tert-Butyl-2'-methoxy-biphenyl-3-yl)-3-thiazol-2-yl-propionic acid;
3-(5-Fluoro-2',6'-dimethoxy-biphenyl-3-yl)-3-(5-methyl-thiazol-2-yl)-propionic acid;
3-(5-Chloro-2',6'-dimethoxy-biphenyl-3-yl)-3-(5-methyl-thiazol-2-yl)-propionic acid;
3-(2',6'-Dimethoxy-biphenyl-3-yl)-3-(5-methyl-thiazol-2-yl)-propionic acid;
3-(5-Chloro-2'-fluoro-6'-methoxy-biphenyl-3-yl)-3-(5-methyl-thiazol-2-yl)-propionic acid;
3-(5-Chloro-2',3',6'-trimethoxy-biphenyl-3-yl)-3-(5-methyl-thiazol-2-yl)-propionic acid;
3-(5-Chloro-5'-hydroxy-2'-methoxy-biphenyl-3-yl)-3-(5-methyl-thiazol-2-yl)-propionic acid;
3-(5-Fluoro-4'-hydroxymethyl-2',6'-dimethoxy-biphenyl-3-yl)-3-oxazol-2-yl-propionic acid;
3-(5-Chloro-2',6'-dimethoxy-biphenyl-3-yl)-3-(5-methyl-[1,3,4]oxadiazol-2-yl)-propionic acid;
3-(5-Chloro-2',6'-dimethoxy-4'-methyl-biphenyl-3-yl)-3-(5-methyl-[1,3,4]oxadiazol-2-yl)-propionic acid;

3-[3-Chloro-5-(6-methoxy-2,2-dimethyl-2,3-dihydro-benzofuran-7-yl)-phenyl]-3-(5-methyl-[1,3,4]oxadiazol-2-yl)-propionic acid;

(R)-3-(5'-Isopropyl-2'-methoxy-biphenyl-3-yl)-3-(5-methyl-[1,3,4]oxadiazol-2-yl)-propionic acid;

3-(2'-Methoxy-5'-methyl-5-trifluoromethyl-biphenyl-3-yl)-3-(5-methyl-[1,3,4]oxadiazol-2-yl)-propionic acid;

3-(5'-tert-Butyl-2'-methoxy-5-trifluoromethyl-biphenyl-3-yl)-3-(5-methyl-[1,3,4]oxadiazol-2-yl)-propionic acid;

3-(2',6'-Dimethoxy-5-trifluoromethyl-biphenyl-3-yl)-3-(5-methyl-[1,3,4]oxadiazol-2-yl)-propionic acid;

3-(2',6'-Dimethoxy-4'-methyl-5-trifluoromethyl-biphenyl-3-yl)-3-(5-methyl-[1,3,4]oxadiazol-2-yl)-propionic acid;

3-[3-(6-Methoxy-2,2-dimethyl-2,3-dihydro-benzofuran-7-yl)-5-trifluoromethyl-phenyl]-3-(5-methyl-[1,3,4]oxadiazol-2-yl)-propionic acid;

3-(2'-Fluoro-6'-methoxy-5-trifluoromethyl-biphenyl-3-yl)-3-(5-methyl-[1,3,4]oxadiazol-2-yl)-propionic acid;

3-(5'-Fluoro-2'-methoxy-5-trifluoromethyl-biphenyl-3-yl)-3-(5-methyl-[1,3,4]oxadiazol-2-yl)-propionic acid;

3-[5'-(Cyano-dimethyl-methyl)-5-fluoro-2'-methoxy-biphenyl-3-yl]-3-(5-methyl-[1,3,4]oxadiazol-2-yl)-propionic acid;

3-(5-Chloro-2'-trifluoromethoxy-biphenyl-3-yl)-3-(5-methyl-thiazol-2-yl)-propionic acid;

3-[5-(2,6-Dimethoxy-phenyl)-pyridin-3-yl]-3-(5-methyl-[1,3,4]oxadiazol-2-yl)-propionic acid;

3-[5-(5-Chloro-2-methoxy-phenyl)-pyridin-3-yl]-3-(5-methyl-[1,3,4]oxadiazol-2-yl)-propionic acid; or 3-[5-(5-Fluoro-2-methoxy-phenyl)-pyridin-3-yl]-3-(5-methyl-[1,3,4]oxadiazol-2-yl)-propionic acid;

in any of its stereoisomeric forms or a mixture of stereoisomeric forms in any ratio, or a physiologically acceptable salt thereof, or a physiologically acceptable solvate of any of them.

7. A pharmaceutical composition, comprising at least one compound of claim 1 or a physiologically acceptable salt thereof or a physiologically acceptable solvate of any of them, and a pharmaceutically acceptable carrier.

8. A method of treating a disease selected from heart failure, congestive heart failure, cardiomyopathy, myocardial infarction, left ventricular dysfunction, cardiac hypertrophy, valvular heart diseases, hypertension, atherosclerosis, peripheral arterial occlusive disease, restenosis, vascular permeability disorders, edema, thrombosis, rheumatoid arthritis, osteoarthritis, renal failure, cystic fibrosis, chronic bronchitis, chronic obstructive pulmonary disease, asthma, diabetic complications, fibrotic diseases, pain, ischemia and reperfusion damage in a patient having said disease, the method comprising administering to said patient a compound of the formula I as claimed in claim 1 or a physiologically acceptable salt thereof or a physiologically acceptable solvate of any of them.

9. A method for treating atrial fibrillation in a patient having atrial fibrillation, the method comprising administering to said patient a compound of the formula I as claimed in claim 1 or a physiologically acceptable salt thereof or a physiologically acceptable solvate of any of them.

10. The compound of the claim 2, in any of its stereoisomeric forms or a mixture of stereoisomeric forms in any ratio, or a physiologically acceptable salt thereof, or a physiologically acceptable solvate of any of them, wherein $G_3$ and $G_4$ are —C(R10)= and —C(R11)=, wherein R10 and R11 form a 5 or 6 membered saturated carbocycle or heterocycle with one or two oxygen atoms, wherein the carbocycle or heterocycle is optionally mono- or disubstituted by halogen and or $(C_1-C_3)$-alkyl.

11. The compound of claim 2, having the formula I-1 or I-11

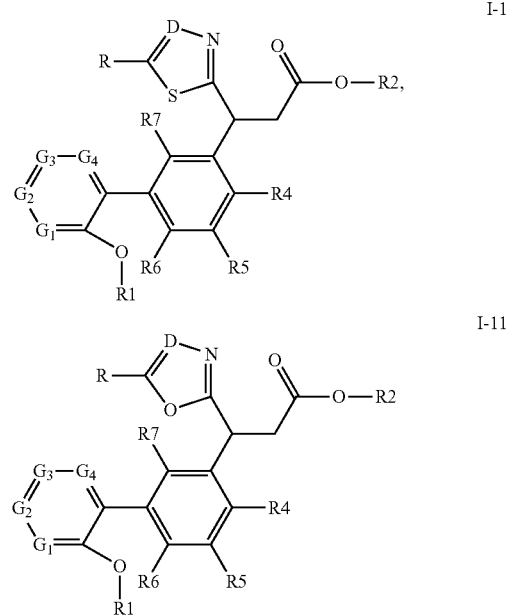

in any of its stereoisomeric forms or a mixture of stereoisomeric forms in any ratio, or a physiologically acceptable salt thereof, or a physiologically acceptable solvate of any of them, wherein $G_1$ is —C(R8)=;

$G_2$ is —C(R9)=;

$G_3$ is —C(R10)=; and $G_4$ is —C(R11)=.

12. The compound of claim 3, having the formula I-1 or I-11

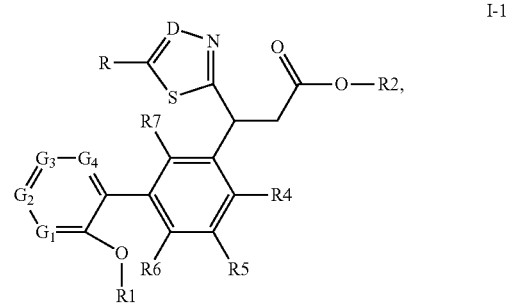

-continued

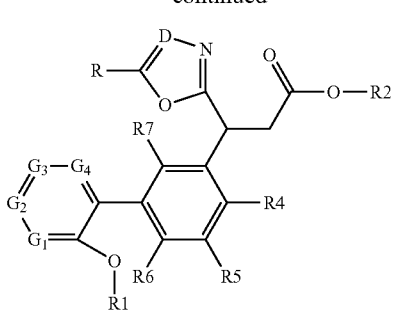
I-11 in any of its stereoisomeric forms or a mixture of stereoisomeric forms in any ratio, or a physiologically acceptable salt thereof, or a physiologically acceptable solvate of any of them,
wherein
$G_1$ is —C(R8)=;
$G_2$ is —C(R9)=;
$G_3$ is —C(R10)=; and
$G_4$ is —C(R11)=.

13. A method for treating a disease selected from heart failure, myocardial infarction, left ventricular dysfunction, cardiac hypertrophy, hypertension and atherosclerosis, the method comprising administering to a patient having said disease a compound of the formula I as claimed in claim 1 or a physiologically acceptable salt thereof or a physiologically acceptable solvate of any of them.

14. A method for treating a disease selected from cystic fibrosis, chronic bronchitis, chronic obstructive pulmonary disease and asthma, the method comprising administering to a patient having said disease a compound of the formula I as claimed in claim 1 or a physiologically acceptable salt thereof or a physiologically acceptable solvate of any of them.

15. A method for treating renal failure, the method comprising administering to a patient experiencing renal failure a compound of the formula I as claimed in claim 1 or a physiologically acceptable salt thereof or a physiologically acceptable solvate of any of them.

16. A method for treating neuropathic pain, the method comprising administering to a patient a compound of the formula I as claimed in claim 1 or a physiologically acceptable salt thereof or a physiologically acceptable solvate of any of them.

17. A method for diuresis, the method comprising administering to a patient in need of diuresis a compound of the formula I as claimed in claim 1 or a physiologically acceptable salt thereof or a physiologically acceptable solvate of any of them as a stand-alone treatment or in combination with established diuretics.

* * * * *